(12) United States Patent
Bonutti

(10) Patent No.: US 8,808,329 B2
(45) Date of Patent: Aug. 19, 2014

(54) APPARATUS AND METHOD FOR SECURING A PORTION OF A BODY

(75) Inventor: Peter M. Bonutti, Effingham, IL (US)

(73) Assignee: Bonutti Skeletal Innovations LLC, Plano, TX (US)

( * ) Notice: Subject to any disclaimer, the term of this patent is extended or adjusted under 35 U.S.C. 154(b) by 0 days.

(21) Appl. No.: 13/438,720

(22) Filed: Apr. 3, 2012

(65) Prior Publication Data

US 2012/0191140 A1 Jul. 26, 2012

Related U.S. Application Data

(63) Continuation of application No. 12/359,364, filed on Jan. 26, 2009, now Pat. No. 8,147,514, which is a continuation of application No. 10/685,117, filed on Oct. 14, 2003, now Pat. No. 7,481,825, which is a continuation of application No. 09/835,473, filed on Apr. 16, 2001, now Pat. No. 6,638,279, which is a continuation of application No. 09/532,942, filed on Mar. 22, 2000, now Pat. No. 6,238,395, which is a continuation of application No. 09/363,707, filed on Jul. 29, 1999, now Pat. No. 6,045,551, which is a continuation-in-part of application No. 09/323,488, filed on Jun. 1, 1999, now Pat. No. 6,117,160, which is a continuation of application No. 09/019,977, filed on Feb. 6, 1998, now Pat. No. 5,921,986.

(51) Int. Cl.

| A61B 17/04 | (2006.01) |
|---|---|
| A61B 17/70 | (2006.01) |
| A61B 17/17 | (2006.01) |
| A61B 17/82 | (2006.01) |
| A61B 17/68 | (2006.01) |

(52) U.S. Cl.
CPC ..... *A61B 17/1796* (2013.01); *A61B 2017/0404* (2013.01); *Y10S 606/907* (2013.01); *A61B 2017/0445* (2013.01); *A61B 17/0401* (2013.01); *Y10S 606/909* (2013.01); *A61B 2017/0458* (2013.01); *A61B 17/82* (2013.01); *A61B 17/683* (2013.01); *Y10S 606/91* (2013.01); *A61B 2017/0454* (2013.01)

USPC .......... 606/263; 606/232; 606/907; 606/909; 606/910

(58) Field of Classification Search
USPC .................... 606/60, 263, 74, 86 R, 228, 232
See application file for complete search history.

(56) References Cited

U.S. PATENT DOCUMENTS

| 157,343 A | 12/1874 | Molesworth |
|---|---|---|
| 319,296 A | 6/1885 | Molesworth |

(Continued)

FOREIGN PATENT DOCUMENTS

| CA | 1312518 C | 1/1993 |
|---|---|---|
| CA | 2641580 | 8/2007 |

(Continued)

OTHER PUBLICATIONS

Copending U.S. Appl. No. 11/932,907—RCE Response Sep. 15, 2011.

(Continued)

*Primary Examiner* — Sameh Boles
(74) *Attorney, Agent, or Firm* — Martin & Ferraro, LLP

(57) ABSTRACT

An anchor connected with a suture is moved through a passage between opposite sides of a bone. The anchor is then pivoted to change its orientation. A second anchor is connected with the suture. While tension is maintained in the suture, the suture is secured against movement relative to the anchors. This may be done by tying the suture or by using a suture retainer to hold the suture. A suture retainer may be used in place of the second anchor. The passage may extend across a fracture in the bone. The passage may have either a nonlinear or linear configuration. The passage may be formed by first moving a thin elongated member through the bone. The thin elongated member is then used as a guide for a drill. The thin elongated member is withdrawn from the drill and the suture anchor is moved through a passage in the drill.

20 Claims, 7 Drawing Sheets

(56) References Cited

U.S. PATENT DOCUMENTS

| | | |
|---|---|---|
| 668,878 A | 2/1901 | Jensen |
| 668,879 A | 2/1901 | Miller |
| 673,783 A | 5/1901 | Peters |
| 702,789 A | 6/1902 | Gibson |
| 832,201 A | 10/1906 | Kistler |
| 862,712 A | 8/1907 | Collins |
| 1,213,005 A | 1/1917 | Pillsbury |
| 1,433,031 A | 10/1922 | Henri |
| 1,725,670 A | 8/1929 | Novack |
| 1,863,057 A | 6/1932 | Innes |
| 1,870,942 A | 8/1932 | Beatty |
| 2,121,193 A | 12/1932 | Hanicke |
| 1,909,967 A | 5/1933 | Jones |
| 1,959,615 A | 5/1934 | Derrah |
| 2,187,852 A | 8/1936 | Friddle |
| 2,178,840 A | 11/1939 | Lorenian |
| 2,199,025 A | 4/1940 | Conn |
| 2,235,419 A | 3/1941 | Callahan |
| 2,248,054 A | 7/1941 | Becker |
| 2,270,188 A | 1/1942 | Longfellow |
| 2,433,815 A | 12/1947 | Nicephore et al. |
| 2,518,276 A | 8/1950 | Braward |
| 2,526,662 A | 10/1950 | Hipps et al. |
| 2,557,669 A | 6/1951 | Lloyd |
| 2,566,499 A | 9/1951 | Richter |
| 2,589,720 A | 3/1952 | McMath |
| 2,621,145 A | 12/1952 | Sano |
| 2,621,653 A | 12/1952 | Briggs |
| 2,642,874 A | 6/1953 | Keeling |
| 2,687,719 A | 8/1954 | Hoyt |
| 2,701,559 A | 2/1955 | Cooper |
| 2,724,326 A | 11/1955 | Long |
| 2,725,053 A | 11/1955 | Bambara |
| 2,830,587 A | 4/1958 | Everett |
| 2,854,983 A | 10/1958 | Baskin |
| 2,936,760 A | 5/1960 | Gants |
| 2,955,530 A | 10/1960 | Nilo |
| 3,039,468 A | 6/1962 | Price |
| 3,048,522 A | 8/1962 | Velley |
| 3,081,773 A | 3/1963 | Boyd |
| 3,108,357 A | 10/1963 | Liebig |
| 3,108,595 A | 10/1963 | Overment |
| 3,367,809 A | 5/1964 | Soloff |
| 3,204,635 A | 9/1965 | Voss et al. |
| 3,229,006 A | 1/1966 | Nohl |
| 3,253,594 A | 5/1966 | Matthews et al. |
| 3,347,234 A | 10/1967 | Voss |
| 3,391,690 A | 7/1968 | Armao |
| 3,397,699 A | 8/1968 | Kohl |
| 3,417,745 A | 12/1968 | Emanuel |
| 3,459,175 A | 8/1969 | Miller |
| 3,469,003 A | 9/1969 | Hardy |
| 3,477,429 A | 11/1969 | Sampson |
| 3,495,586 A | 2/1970 | Regenbogen |
| 3,513,848 A | 5/1970 | Winston et al. |
| 3,514,791 A | 6/1970 | Sparks |
| 3,517,128 A | 6/1970 | Hines |
| 3,518,993 A | 7/1970 | Blake |
| 3,554,192 A | 1/1971 | Isberner |
| 3,557,794 A | 1/1971 | Patten |
| 3,577,991 A | 5/1971 | Wilkinson |
| 3,593,709 A | 7/1971 | Halloran |
| 3,596,292 A | 8/1971 | Erb et al. |
| 3,608,539 A | 9/1971 | Miller |
| 3,613,497 A | 10/1971 | Heldermann |
| 3,620,218 A | 11/1971 | Schmitt et al. |
| 3,624,747 A | 11/1971 | McKnight et al. |
| 3,625,220 A | 12/1971 | Engelsher |
| 3,626,949 A | 12/1971 | Shute |
| 3,635,223 A | 1/1972 | Klieman |
| 3,648,705 A | 3/1972 | Lary |
| 3,653,388 A | 4/1972 | Tenckhoff |
| 3,656,476 A | 4/1972 | Swinney |
| 3,657,056 A | 4/1972 | Winston et al. |
| 3,670,732 A | 6/1972 | Robinson |
| 3,678,980 A | 7/1972 | Gutshall |
| 3,698,017 A | 10/1972 | Scales et al. |
| 3,709,218 A | 1/1973 | Halloran |
| 3,711,347 A | 1/1973 | Wagner et al. |
| 3,716,051 A | 2/1973 | Fischer |
| 3,721,244 A | 3/1973 | Elmaleh |
| 3,739,773 A | 6/1973 | Schmitt et al. |
| 3,750,652 A | 8/1973 | Sherwin |
| 3,760,808 A | 9/1973 | Bleuer |
| 3,769,980 A | 11/1973 | Karman |
| 3,774,244 A | 11/1973 | Walker |
| 3,774,596 A | 11/1973 | Cook |
| 3,779,239 A | 12/1973 | Fischer et al. |
| 3,788,318 A | 1/1974 | Kim et al. |
| 3,789,852 A | 2/1974 | Kim et al. |
| 3,800,788 A | 4/1974 | White |
| 3,802,438 A | 4/1974 | Wolvek |
| 3,804,089 A | 4/1974 | Bridgman |
| 3,807,393 A | 4/1974 | McDonald |
| 3,807,394 A | 4/1974 | Attenborough |
| 3,809,075 A | 5/1974 | Matles |
| 3,811,449 A | 5/1974 | Gravlee et al. |
| 3,812,855 A | 5/1974 | Banko |
| 3,825,010 A | 7/1974 | McDonald |
| 3,833,003 A | 9/1974 | Taricco |
| 3,835,849 A | 9/1974 | McGuire |
| 3,841,304 A | 10/1974 | Jones |
| 3,842,824 A | 10/1974 | Neufeld |
| 3,845,772 A | 11/1974 | Smith |
| 3,850,172 A | 11/1974 | Cazalis |
| 3,850,720 A | 11/1974 | Collins |
| 3,852,830 A | 12/1974 | Marmor |
| 3,857,396 A | 12/1974 | Hardwick |
| 3,863,639 A | 2/1975 | Kleaveland |
| 3,867,932 A | 2/1975 | Huene |
| 3,869,731 A | 3/1975 | Waugh et al. |
| 3,874,264 A | 4/1975 | Polos |
| 3,875,652 A | 4/1975 | Arnold |
| 3,875,946 A | 4/1975 | Duncan |
| 3,882,852 A | 5/1975 | Sinnreich |
| 3,889,686 A | 6/1975 | Duturbure et al. |
| 3,894,530 A | 7/1975 | Dardik et al. |
| 3,898,992 A | 8/1975 | Balamuth |
| 3,903,549 A | 9/1975 | Deyerle |
| 3,911,923 A | 10/1975 | Yoon |
| 3,915,171 A | 10/1975 | Shermeta |
| 3,918,442 A | 11/1975 | Nikolaev et al. |
| 3,920,022 A | 11/1975 | Pastor |
| 3,939,835 A | 2/1976 | Bridgman |
| 3,945,375 A | 3/1976 | Banko |
| 3,960,143 A | 6/1976 | Terada |
| 3,961,632 A | 6/1976 | Moossun |
| 3,967,625 A | 7/1976 | Yoon |
| 3,968,800 A | 7/1976 | Vilasi |
| 3,970,089 A | 7/1976 | Saice |
| 3,973,277 A | 8/1976 | Semple et al. |
| 3,976,079 A | 8/1976 | Samuels et al. |
| 3,989,049 A | 11/1976 | Yoon |
| 3,991,426 A | 11/1976 | Flom et al. |
| 3,994,287 A | 11/1976 | Turp et al. |
| 4,000,525 A | 1/1977 | Klawitter et al. |
| 4,022,216 A | 5/1977 | Stevens |
| 4,023,559 A | 5/1977 | Gaskell |
| 4,040,413 A | 8/1977 | Ohshiro |
| 4,053,953 A | 10/1977 | Flom et al. |
| 4,055,862 A | 11/1977 | Farling |
| 4,064,566 A | 12/1977 | Fletcher et al. |
| 4,077,412 A | 3/1978 | Moossun |
| 4,081,866 A | 4/1978 | Upshaw et al. |
| 4,083,369 A | 4/1978 | Sinnreich |
| 4,085,466 A | 4/1978 | Goodfellow et al. |
| 4,085,743 A | 4/1978 | Yoon |
| 4,089,071 A | 5/1978 | Kainberz et al. |
| 4,092,113 A | 5/1978 | Hardy |
| 4,103,680 A | 8/1978 | Yoon |
| RE29,757 E | 9/1978 | Helfet |
| 4,122,605 A | 10/1978 | Hirabayashi et al. |
| 4,142,517 A | 3/1979 | Contreras et al. |
| 4,148,307 A | 4/1979 | Utsugi |

(56) References Cited

U.S. PATENT DOCUMENTS

| | | |
|---|---|---|
| 4,156,574 A | 5/1979 | Boden |
| 4,164,794 A | 8/1979 | Spector et al. |
| 4,169,470 A | 10/1979 | Ender et al. |
| 4,171,544 A | 10/1979 | Hench et al. |
| 4,177,814 A | 12/1979 | Knepshield et al. |
| 4,183,102 A | 1/1980 | Guiset |
| 4,186,448 A | 2/1980 | Brekke |
| 4,191,747 A | 3/1980 | Scheicher |
| 4,198,981 A | 4/1980 | Sinnreich |
| 4,199,864 A | 4/1980 | Ashman |
| 4,200,939 A | 5/1980 | Oser |
| 4,203,444 A | 5/1980 | Bonnell et al. |
| 4,209,012 A | 6/1980 | Smucker |
| 4,209,861 A | 7/1980 | Brozone et al. |
| 4,210,148 A | 7/1980 | Stivala |
| 4,210,580 A | 7/1980 | Amrani |
| 4,213,209 A | 7/1980 | Insall et al. |
| 4,213,816 A | 7/1980 | Morris |
| 4,224,696 A | 9/1980 | Murray et al. |
| 4,224,929 A | 9/1980 | Furihata |
| 4,228,802 A | 10/1980 | Trott |
| 4,230,119 A | 10/1980 | Blum |
| 4,235,233 A | 11/1980 | Mouwen |
| 4,235,238 A | 11/1980 | Ogiu et al. |
| 4,240,433 A | 12/1980 | Bordow |
| 4,243,048 A | 1/1981 | Griffin |
| 4,244,370 A | 1/1981 | Furlow et al. |
| 4,257,411 A | 3/1981 | Cho |
| 4,263,900 A | 4/1981 | Nicholson |
| 4,265,231 A | 5/1981 | Scheller, Jr. et al. |
| 4,265,848 A | 5/1981 | Ruesch |
| 4,274,414 A | 6/1981 | Johnson et al. |
| 4,281,649 A | 8/1981 | Derweduwen |
| 4,291,698 A | 9/1981 | Fuchs |
| 4,295,464 A | 10/1981 | Shihata |
| 4,298,002 A | 11/1981 | Ronel et al. |
| 4,298,992 A | 11/1981 | Burstein et al. |
| 4,298,998 A | 11/1981 | Naficy |
| 4,299,224 A | 11/1981 | Noiles |
| 4,299,227 A | 11/1981 | Lincoff |
| 4,304,178 A | 12/1981 | Haeberle |
| 4,309,488 A | 1/1982 | Heide et al. |
| 4,311,145 A | 1/1982 | Esty et al. |
| 4,312,353 A | 1/1982 | Shahbabian |
| 4,320,762 A | 3/1982 | Bentov |
| 4,344,193 A | 8/1982 | Kenny |
| 4,349,029 A | 9/1982 | Mott |
| 4,349,921 A | 9/1982 | Kuntz |
| 4,351,069 A | 9/1982 | Ballintyn et al. |
| 4,352,883 A | 10/1982 | Lim |
| 4,357,940 A | 11/1982 | Muller |
| 4,364,381 A | 12/1982 | Sher et al. |
| 4,365,356 A | 12/1982 | Broemer et al. |
| 4,369,768 A | 1/1983 | Vukovic |
| 4,373,217 A | 2/1983 | Draenert |
| 4,373,709 A | 2/1983 | Whitt |
| 4,374,523 A | 2/1983 | Yoon |
| 4,385,404 A | 5/1983 | Sully et al. |
| 4,388,921 A | 6/1983 | Sutter et al. |
| 4,391,909 A | 7/1983 | Lim |
| 4,395,798 A | 8/1983 | McVey |
| 4,400,833 A | 8/1983 | Kurland |
| 4,407,273 A | 10/1983 | Ouchi |
| 4,409,974 A | 10/1983 | Freedland |
| 4,414,166 A | 11/1983 | Charlson et al. |
| 4,421,112 A | 12/1983 | Mains et al. |
| 4,430,760 A | 2/1984 | Smestad |
| 4,434,797 A | 3/1984 | Silander |
| 4,437,191 A | 3/1984 | Van der Zet et al. |
| 4,437,362 A | 3/1984 | Hurst |
| 4,442,655 A | 4/1984 | Stroetmann et al. |
| 4,444,180 A | 4/1984 | Schneider et al. |
| 4,445,509 A | 5/1984 | Auth |
| 4,447,227 A | 5/1984 | Kotsanis |
| 4,448,194 A | 5/1984 | DiGiovanni et al. |
| 4,450,591 A | 5/1984 | Rappaport |
| 4,453,421 A | 6/1984 | Umano |
| 4,453,539 A | 6/1984 | Raftopoulos et al. |
| 4,456,005 A | 6/1984 | Lichty |
| 4,457,302 A | 7/1984 | Caspari et al. |
| 4,461,281 A | 7/1984 | Carson |
| 4,466,429 A | 8/1984 | Loscher et al. |
| 4,466,888 A | 8/1984 | Verkaart |
| 4,472,840 A | 9/1984 | Jefferies |
| 4,474,177 A | 10/1984 | Whiteside |
| 4,484,579 A | 11/1984 | Meno et al. |
| 4,485,096 A | 11/1984 | Bell |
| 4,487,203 A | 12/1984 | Androphy |
| 4,493,317 A | 1/1985 | Klaue |
| 4,495,664 A | 1/1985 | Blanquaert |
| 4,501,031 A | 2/1985 | McDaniel et al. |
| 4,501,266 A | 2/1985 | McDaniel |
| 4,501,269 A | 2/1985 | Bagby |
| 4,502,159 A | 3/1985 | Woodroof et al. |
| 4,502,161 A | 3/1985 | Wall |
| 4,504,268 A | 3/1985 | Herlitze |
| 4,505,274 A | 3/1985 | Speelman |
| 4,506,681 A | 3/1985 | Mundell |
| 4,509,518 A | 4/1985 | McGarry et al. |
| 4,514,125 A | 4/1985 | Stol |
| 4,516,276 A | 5/1985 | Mittelmeier et al. |
| 4,526,173 A | 7/1985 | Sheehan |
| 4,532,926 A | 8/1985 | O'Holla |
| 4,535,757 A | 8/1985 | Webster |
| 4,535,772 A | 8/1985 | Sheehan |
| 4,540,404 A | 9/1985 | Wolvek |
| 4,541,423 A | 9/1985 | Barber |
| 4,543,375 A | 9/1985 | Doebler et al. |
| 4,545,374 A | 10/1985 | Jacobson |
| 4,547,327 A | 10/1985 | Bruins et al. |
| 4,551,135 A | 11/1985 | Gorman et al. |
| 4,553,272 A | 11/1985 | Mears |
| 4,554,686 A | 11/1985 | Baker |
| 4,555,242 A | 11/1985 | Saudagar |
| 4,556,059 A | 12/1985 | Adamson, Jr. |
| 4,556,350 A | 12/1985 | Bernhardt et al. |
| 4,556,391 A | 12/1985 | Tardivel et al. |
| 4,562,598 A | 1/1986 | Kranz |
| 4,565,192 A | 1/1986 | Shapiro |
| 4,566,138 A | 1/1986 | Lewis et al. |
| 4,572,186 A | 2/1986 | Gould et al. |
| 4,573,448 A | 3/1986 | Kambin |
| 4,574,794 A | 3/1986 | Cooke et al. |
| 4,575,371 A | 3/1986 | Nordqvist et al. |
| 4,584,722 A | 4/1986 | Levy et al. |
| 4,585,000 A | 4/1986 | Hershenson |
| 4,589,414 A | 5/1986 | Yoshida et al. |
| 4,589,686 A | 5/1986 | McGrew |
| 4,589,868 A | 5/1986 | Dretler |
| 4,590,928 A | 5/1986 | Hunt et al. |
| 4,597,379 A | 7/1986 | Kihn et al. |
| 4,599,085 A | 7/1986 | Riess et al. |
| 4,601,893 A | 7/1986 | Cardinal |
| 4,603,694 A | 8/1986 | Wheeler |
| 4,606,335 A | 8/1986 | Wedeen |
| 4,608,052 A | 8/1986 | Van Kampen et al. |
| 4,608,965 A | 9/1986 | Anspach, Jr. et al. |
| 4,610,662 A | 9/1986 | Weikl et al. |
| 4,611,593 A | 9/1986 | Fogarty et al. |
| 4,615,717 A | 10/1986 | Neubauer et al. |
| 4,619,391 A | 10/1986 | Sharkany et al. |
| 4,621,640 A | 11/1986 | Mulhollan et al. |
| 4,623,553 A | 11/1986 | Ries et al. |
| 4,624,254 A | 11/1986 | McGarry et al. |
| 4,630,609 A | 12/1986 | Chin |
| 4,632,101 A | 12/1986 | Freedland |
| 4,641,648 A | 2/1987 | Shapiro |
| 4,642,117 A | 2/1987 | Nguyen et al. |
| 4,642,120 A | 2/1987 | Nevo et al. |
| 4,645,503 A | 2/1987 | Lin et al. |
| 4,646,736 A | 3/1987 | Auth |
| 4,646,738 A | 3/1987 | Trott |
| 4,649,918 A | 3/1987 | Pegg et al. |
| 4,651,717 A | 3/1987 | Jakubczak |

(56) References Cited

U.S. PATENT DOCUMENTS

| | | |
|---|---|---|
| 4,651,752 A | 3/1987 | Fuerst |
| 4,654,464 A | 3/1987 | Mittelmeier et al. |
| 4,657,460 A | 4/1987 | Bien |
| 4,657,548 A | 4/1987 | Nichols |
| 4,659,268 A | 4/1987 | Del Mundo et al. |
| 4,662,063 A | 5/1987 | Collins et al. |
| 4,662,068 A | 5/1987 | Polonsky |
| 4,662,372 A | 5/1987 | Sharkany et al. |
| 4,662,887 A | 5/1987 | Turner et al. |
| 4,669,473 A | 6/1987 | Richards et al. |
| 4,678,470 A | 7/1987 | Nashef et al. |
| 4,681,106 A | 7/1987 | Kensey et al. |
| 4,681,107 A | 7/1987 | Kees, Jr. |
| 4,682,598 A | 7/1987 | Beraha |
| 4,685,458 A | 8/1987 | Leckrone |
| 4,685,460 A | 8/1987 | Thornton |
| 4,691,741 A | 9/1987 | Affa et al. |
| 4,696,667 A | 9/1987 | Masch |
| 4,705,040 A | 11/1987 | Mueller et al. |
| 4,706,659 A | 11/1987 | Matthews et al. |
| 4,706,670 A | 11/1987 | Andersen et al. |
| 4,708,139 A | 11/1987 | Dunbar, IV |
| 4,711,233 A | 12/1987 | Brown |
| 4,712,542 A | 12/1987 | Daniel et al. |
| 4,713,076 A | 12/1987 | Draenert |
| 4,713,077 A | 12/1987 | Small |
| 4,714,074 A | 12/1987 | Rey et al. |
| 4,716,893 A | 1/1988 | Fischer et al. |
| 4,716,901 A | 1/1988 | Jackson et al. |
| 4,718,909 A | 1/1988 | Brown |
| 4,718,916 A | 1/1988 | Morscher |
| 4,719,908 A | 1/1988 | Averill et al. |
| 4,721,096 A | 1/1988 | Naughton et al. |
| 4,721,103 A | 1/1988 | Freedland |
| 4,721,104 A | 1/1988 | Kaufman et al. |
| 4,722,331 A | 2/1988 | Fox |
| 4,722,948 A | 2/1988 | Sanderson |
| 4,724,584 A | 2/1988 | Kasai |
| 4,738,255 A | 4/1988 | Goble et al. |
| 4,739,751 A | 4/1988 | Sapega et al. |
| 4,741,330 A | 5/1988 | Hayhurst |
| 4,743,229 A | 5/1988 | Chu |
| 4,743,259 A | 5/1988 | Bolander et al. |
| 4,744,364 A | 5/1988 | Kensey |
| 4,747,405 A | 5/1988 | Leckrone |
| 4,749,585 A | 6/1988 | Greco et al. |
| 4,750,488 A | 6/1988 | Wuchinich et al. |
| 4,750,492 A | 6/1988 | Jacobs |
| 4,751,922 A | 6/1988 | Dipietropolo |
| 4,755,184 A | 7/1988 | Silverberg |
| 4,759,350 A | 7/1988 | Dunn et al. |
| 4,768,507 A | 9/1988 | Fischell |
| 4,772,286 A | 9/1988 | Goble et al. |
| 4,776,328 A | 10/1988 | Frey et al. |
| 4,776,738 A | 10/1988 | Winston |
| 4,776,851 A | 10/1988 | Bruchman et al. |
| 4,779,611 A | 10/1988 | Grooters et al. |
| 4,781,182 A | 11/1988 | Purnell et al. |
| 4,781,681 A | 11/1988 | Sharrow et al. |
| 4,781,922 A | 11/1988 | Bone |
| 4,784,133 A | 11/1988 | Mackin |
| 4,789,663 A | 12/1988 | Wallace et al. |
| 4,790,303 A | 12/1988 | Steffee |
| 4,790,819 A | 12/1988 | Li et al. |
| 4,792,336 A | 12/1988 | Hiavacek et al. |
| 4,793,359 A | 12/1988 | Sharrow |
| 4,794,854 A | 1/1989 | Swaim |
| 4,795,467 A | 1/1989 | Piez et al. |
| 4,796,629 A | 1/1989 | Grayzel |
| 4,798,205 A | 1/1989 | Bonomo et al. |
| 4,798,213 A | 1/1989 | Doppelt |
| 4,800,901 A | 1/1989 | Rosenberg |
| 4,801,299 A | 1/1989 | Brendel et al. |
| 4,802,479 A | 2/1989 | Haber et al. |
| 4,817,591 A | 4/1989 | Klause |
| 4,817,602 A | 4/1989 | Beraha |
| 4,822,224 A | 4/1989 | Carl et al. |
| 4,823,794 A | 4/1989 | Pierce |
| 4,825,857 A | 5/1989 | Kenna |
| 4,828,563 A | 5/1989 | Muller-Lierheim et al. |
| 4,832,025 A | 5/1989 | Coates |
| 4,832,026 A | 5/1989 | Jones |
| 4,832,683 A | 5/1989 | Idemoto et al. |
| 4,834,752 A | 5/1989 | Van Kampen |
| 4,834,757 A | 5/1989 | Brantigan |
| 4,841,960 A | 6/1989 | Garner |
| 4,842,517 A | 6/1989 | Kawahara et al. |
| 4,843,112 A | 6/1989 | Gerhart |
| 4,844,064 A | 7/1989 | Thimsen et al. |
| 4,846,791 A | 7/1989 | Hattler et al. |
| 4,846,812 A | 7/1989 | Walker et al. |
| 4,846,835 A | 7/1989 | Grande |
| 4,857,045 A | 8/1989 | Rydell |
| 4,861,334 A | 8/1989 | Nawaz |
| 4,862,874 A | 9/1989 | Kellner |
| 4,862,882 A | 9/1989 | Venturi et al. |
| 4,862,974 A | 9/1989 | Warren et al. |
| 4,863,472 A | 9/1989 | Tormala et al. |
| 4,867,157 A | 9/1989 | McGurk-Burleson et al. |
| 4,869,242 A | 9/1989 | Galluzzo |
| 4,870,957 A | 10/1989 | Goble et al. |
| 4,875,468 A | 10/1989 | Krauter et al. |
| 4,877,020 A | 10/1989 | Vich |
| 4,880,429 A | 11/1989 | Stone |
| 4,883,048 A | 11/1989 | Purnell et al. |
| 4,883,666 A | 11/1989 | Sabel et al. |
| 4,888,022 A | 12/1989 | Huebsch |
| 4,890,612 A | 1/1990 | Kensey |
| 4,892,552 A | 1/1990 | Ainsworth et al. |
| 4,895,148 A | 1/1990 | Bays et al. |
| 4,898,156 A | 2/1990 | Gatturna et al. |
| 4,899,729 A | 2/1990 | Gill et al. |
| 4,899,743 A | 2/1990 | Nicholson et al. |
| 4,899,744 A | 2/1990 | Fujitsuka et al. |
| 4,901,721 A | 2/1990 | Hakki |
| 4,902,296 A | 2/1990 | Bolander et al. |
| 4,904,259 A | 2/1990 | Itay |
| 4,904,261 A | 2/1990 | Dove |
| 4,909,789 A | 3/1990 | Taguchi |
| 4,911,721 A | 3/1990 | Aendergaten et al. |
| 4,919,667 A | 4/1990 | Richmond |
| 4,921,478 A | 5/1990 | Solano et al. |
| 4,921,479 A | 5/1990 | Grayzel |
| 4,922,897 A | 5/1990 | Sapega et al. |
| 4,923,464 A | 5/1990 | DiPisa, Jr. |
| 4,924,865 A | 5/1990 | Bays et al. |
| 4,924,866 A | 5/1990 | Yoon |
| 4,927,412 A | 5/1990 | Menasche |
| 4,927,421 A | 5/1990 | Goble et al. |
| 4,932,956 A | 6/1990 | Reddy et al. |
| 4,932,959 A | 6/1990 | Horzewski et al. |
| 4,932,960 A | 6/1990 | Green et al. |
| 4,932,973 A | 6/1990 | Gendler |
| 4,935,023 A | 6/1990 | Whiteside et al. |
| 4,935,028 A | 6/1990 | Drews |
| 4,936,848 A | 6/1990 | Bagby |
| 4,936,852 A | 6/1990 | Kent et al. |
| 4,944,760 A | 7/1990 | Kenna |
| 4,945,625 A | 8/1990 | Winston |
| 4,945,896 A | 8/1990 | Gade |
| 4,946,468 A | 8/1990 | Li |
| 4,950,296 A | 8/1990 | McIntyre |
| 4,950,298 A | 8/1990 | Gustilo et al. |
| 4,952,213 A | 8/1990 | Bowman et al. |
| 4,954,126 A | 9/1990 | Wallsten |
| 4,955,910 A | 9/1990 | Bolesky |
| 4,957,498 A | 9/1990 | Caspari et al. |
| 4,961,740 A | 10/1990 | Ray et al. |
| 4,961,741 A | 10/1990 | Hayhurst |
| 4,961,954 A | 10/1990 | Goldberg et al. |
| 4,963,151 A | 10/1990 | Ducheyne et al. |
| 4,963,489 A | 10/1990 | Naughton et al. |
| 4,964,862 A | 10/1990 | Arms |
| 4,964,865 A | 10/1990 | Burkhead et al. |

(56) References Cited

U.S. PATENT DOCUMENTS

| | | |
|---|---|---|
| 4,966,583 A | 10/1990 | Debbas |
| 4,968,298 A | 11/1990 | Michelson |
| 4,968,315 A | 11/1990 | Gatturna |
| 4,969,888 A | 11/1990 | Scholten et al. |
| 4,969,892 A | 11/1990 | Burton et al. |
| 4,969,895 A | 11/1990 | McLeod et al. |
| 4,979,949 A | 12/1990 | Matsen, III et al. |
| 4,979,957 A | 12/1990 | Hodorek |
| 4,983,179 A | 1/1991 | Sjostrom |
| 4,984,563 A | 1/1991 | Renaud |
| 4,984,564 A | 1/1991 | Yuen |
| 4,985,038 A | 1/1991 | Lyell |
| 4,990,161 A | 2/1991 | Kampner |
| 4,994,047 A | 2/1991 | Walker et al. |
| 4,994,067 A | 2/1991 | Summers |
| 4,994,071 A | 2/1991 | MacGregor |
| 4,995,868 A | 2/1991 | Brazier |
| 4,997,445 A | 3/1991 | Hodorek |
| 4,998,539 A | 3/1991 | Delsanti |
| 5,002,550 A | 3/1991 | Li |
| 5,002,557 A | 3/1991 | Hasson |
| 5,002,563 A | 3/1991 | Pyka et al. |
| 5,007,912 A | 4/1991 | Albrektsson et al. |
| 5,009,652 A | 4/1991 | Morgan et al. |
| 5,009,662 A | 4/1991 | Wallace et al. |
| 5,009,663 A | 4/1991 | Broome |
| 5,009,664 A | 4/1991 | Sievers |
| 5,013,316 A | 5/1991 | Goble et al. |
| 5,015,247 A | 5/1991 | Michelson |
| 5,015,255 A | 5/1991 | Kuslich |
| 5,019,090 A | 5/1991 | Pinchuk |
| 5,019,104 A | 5/1991 | Whiteside et al. |
| 5,021,056 A | 6/1991 | Hofmann et al. |
| 5,021,059 A | 6/1991 | Kensey et al. |
| 5,026,373 A | 6/1991 | Ray et al. |
| 5,027,827 A | 7/1991 | Cody et al. |
| 5,032,132 A | 7/1991 | Matsen, III et al. |
| 5,035,699 A | 7/1991 | Coates |
| 5,035,713 A | 7/1991 | Friis |
| 5,037,404 A | 8/1991 | Gold et al. |
| 5,037,422 A | 8/1991 | Hayhurst et al. |
| 5,037,423 A | 8/1991 | Kenna |
| 5,041,093 A | 8/1991 | Chu |
| 5,041,114 A | 8/1991 | Chapman et al. |
| 5,041,125 A | 8/1991 | Montano, Jr. |
| 5,041,129 A | 8/1991 | Hayhurst et al. |
| 5,042,976 A | 8/1991 | Ishitsu et al. |
| 5,046,513 A | 9/1991 | Gatturna et al. |
| 5,047,055 A | 9/1991 | Bao et al. |
| 5,051,049 A | 9/1991 | Wills |
| 5,053,009 A | 10/1991 | Herzberg |
| 5,053,039 A | 10/1991 | Hofmann et al. |
| 5,053,046 A | 10/1991 | Janese |
| 5,053,047 A | 10/1991 | Yoon |
| 5,059,193 A | 10/1991 | Kuslich |
| 5,059,206 A | 10/1991 | Winters |
| 5,060,678 A | 10/1991 | Bauman et al. |
| 5,061,274 A | 10/1991 | Kensey |
| 5,061,281 A | 10/1991 | Mares et al. |
| 5,061,286 A | 10/1991 | Lyle |
| 5,062,843 A | 11/1991 | Mahony, III |
| 5,069,674 A | 12/1991 | Fearnot et al. |
| 5,071,411 A | 12/1991 | Hillstead |
| 5,073,373 A | 12/1991 | O'Leary et al. |
| 5,078,731 A | 1/1992 | Hayhurst |
| 5,078,744 A | 1/1992 | Chvapil |
| 5,078,745 A | 1/1992 | Rhenter et al. |
| 5,082,670 A | 1/1992 | Gage et al. |
| 5,084,050 A | 1/1992 | Draenert |
| 5,084,051 A | 1/1992 | Tormala et al. |
| 5,085,660 A | 2/1992 | Lin |
| 5,085,661 A | 2/1992 | Moss |
| 5,092,348 A | 3/1992 | Dubrul et al. |
| 5,098,433 A | 3/1992 | Freedland |
| 5,098,434 A | 3/1992 | Serbousek |
| 5,098,436 A | 3/1992 | Ferrante et al. |
| 5,098,437 A | 3/1992 | Kashuba et al. |
| 5,099,859 A | 3/1992 | Bell |
| 5,100,405 A | 3/1992 | McLaren |
| 5,100,409 A | 3/1992 | Coates et al. |
| 5,100,417 A | 3/1992 | Cerier et al. |
| 5,100,689 A | 3/1992 | Goldberg et al. |
| 5,101,720 A | 4/1992 | Bianchi |
| 5,102,417 A | 4/1992 | Palmaz |
| 5,102,421 A | 4/1992 | Anspach, Jr. |
| 5,104,383 A | 4/1992 | Shichman |
| 5,108,399 A | 4/1992 | Eitenmuller et al. |
| 5,108,433 A | 4/1992 | May et al. |
| 5,108,441 A | 4/1992 | McDowell |
| 5,111,987 A | 5/1992 | Moeinzadeh et al. |
| 5,116,374 A | 5/1992 | Stone |
| 5,120,175 A | 6/1992 | Arbegast et al. |
| 5,122,122 A | 6/1992 | Allgood |
| 5,122,144 A | 6/1992 | Bert et al. |
| 5,123,520 A | 6/1992 | Schmid et al. |
| 5,123,906 A | 6/1992 | Kelman |
| 5,123,914 A | 6/1992 | Cope |
| 5,123,941 A | 6/1992 | Lauren et al. |
| 5,133,732 A | 7/1992 | Wiktor |
| RE34,021 E | 8/1992 | Mueller |
| 5,135,522 A | 8/1992 | Fahrenkrug et al. |
| 5,139,520 A | 8/1992 | Rosenberg |
| 5,141,520 A | 8/1992 | Goble et al. |
| 5,143,062 A | 9/1992 | Peckham |
| 5,143,093 A | 9/1992 | Sahota |
| 5,147,362 A | 9/1992 | Goble |
| 5,152,744 A | 10/1992 | Krause et al. |
| 5,152,765 A | 10/1992 | Ross et al. |
| 5,152,778 A | 10/1992 | Bales, Jr. et al. |
| 5,154,717 A | 10/1992 | Matsen, III et al. |
| 5,154,720 A | 10/1992 | Trott et al. |
| 5,156,613 A | 10/1992 | Sawyer |
| 5,156,616 A | 10/1992 | Meadows et al. |
| 5,158,553 A | 10/1992 | Berry et al. |
| 5,158,566 A | 10/1992 | Pianetti |
| 5,158,571 A | 10/1992 | Picha |
| 5,158,934 A | 10/1992 | Ammann et al. |
| 5,159,921 A | 11/1992 | Hoover |
| 5,162,506 A | 11/1992 | Hadden |
| 5,163,949 A | 11/1992 | Bonutti |
| 5,163,960 A | 11/1992 | Bonutti |
| 5,170,800 A | 12/1992 | Smith et al. |
| 5,171,243 A | 12/1992 | Kashuba et al. |
| 5,171,244 A | 12/1992 | Caspari et al. |
| 5,171,251 A | 12/1992 | Bregen et al. |
| 5,171,276 A | 12/1992 | Caspari et al. |
| 5,174,300 A | 12/1992 | Bales et al. |
| 1,312,518 A | 1/1993 | Hayhurst |
| 5,176,682 A | 1/1993 | Chow |
| 5,176,684 A | 1/1993 | Ferrante et al. |
| 5,176,702 A | 1/1993 | Bales et al. |
| 5,178,622 A | 1/1993 | Lehner, II |
| 5,179,964 A | 1/1993 | Cook |
| 5,180,388 A | 1/1993 | DiCarlo |
| 5,183,053 A | 2/1993 | Yeh et al. |
| 5,183,464 A | 2/1993 | Dubrul et al. |
| 5,185,001 A | 2/1993 | Galanakis |
| 5,186,178 A | 2/1993 | Yeh et al. |
| 5,192,287 A | 3/1993 | Fournier et al. |
| 5,192,326 A | 3/1993 | Bao et al. |
| 5,192,327 A | 3/1993 | Brantigan |
| 5,195,507 A | 3/1993 | Bilweis |
| 5,195,970 A | 3/1993 | Gahara |
| 5,197,166 A | 3/1993 | Meier et al. |
| 5,197,488 A | 3/1993 | Kovacevic |
| 5,197,955 A | 3/1993 | Stephens et al. |
| 5,197,968 A | 3/1993 | Clement |
| 5,197,971 A | 3/1993 | Bonutti |
| 5,197,987 A | 3/1993 | Koch et al. |
| 5,201,768 A | 4/1993 | Caspari et al. |
| 5,203,784 A | 4/1993 | Ross et al. |
| 5,203,787 A | 4/1993 | Noblitt et al. |
| 5,204,106 A | 4/1993 | Schepers et al. |
| 5,207,692 A | 5/1993 | Kraus et al. |

(56) References Cited

U.S. PATENT DOCUMENTS

| | | | |
|---|---|---|---|
| 5,208,950 | A | 5/1993 | Merritt |
| 5,209,776 | A | 5/1993 | Bass et al. |
| 5,211,647 | A | 5/1993 | Schmieding |
| 5,217,463 | A | 6/1993 | Mikhail |
| 5,217,486 | A | 6/1993 | Rice et al. |
| 5,217,493 | A | 6/1993 | Raad et al. |
| 5,219,359 | A | 6/1993 | McQuilkin et al. |
| 5,224,946 | A | 7/1993 | Hayhurst et al. |
| 5,226,426 | A | 7/1993 | Yoon |
| 5,226,877 | A | 7/1993 | Epstein |
| 5,226,899 | A | 7/1993 | Lee et al. |
| 5,226,915 | A | 7/1993 | Bertin |
| 5,228,459 | A | 7/1993 | Caspari et al. |
| 5,234,006 | A | 8/1993 | Eaton et al. |
| 5,234,425 | A | 8/1993 | Fogarty et al. |
| 5,234,433 | A | 8/1993 | Bert et al. |
| 5,236,432 | A | 8/1993 | Matsen, III et al. |
| 5,236,438 | A | 8/1993 | Wilk |
| 5,236,445 | A | 8/1993 | Hayhurst et al. |
| 5,242,902 | A | 9/1993 | Murphy et al. |
| 5,244,946 | A | 9/1993 | Guest et al. |
| 5,246,441 | A | 9/1993 | Ross et al. |
| 5,250,026 | A | 10/1993 | Ehrlich et al. |
| 5,250,055 | A | 10/1993 | Moore et al. |
| 5,250,070 | A | 10/1993 | Parodi |
| 5,254,091 | A | 10/1993 | Aliahmad et al. |
| 5,254,113 | A | 10/1993 | Wilk |
| 5,258,004 | A | 11/1993 | Bales et al. |
| 5,258,007 | A | 11/1993 | Spetzler et al. |
| 5,258,015 | A | 11/1993 | Li et al. |
| 5,258,016 | A | 11/1993 | DiPoto et al. |
| 5,258,031 | A | 11/1993 | Salib et al. |
| 5,258,032 | A | 11/1993 | Bertin |
| 5,261,914 | A | 11/1993 | Warren |
| 5,263,498 | A | 11/1993 | Caspari et al. |
| 5,263,987 | A | 11/1993 | Shah |
| 5,266,325 | A | 11/1993 | Kuzma et al. |
| 5,268,001 | A | 12/1993 | Nicholson et al. |
| 5,269,783 | A | 12/1993 | Sander |
| 5,269,785 | A | 12/1993 | Bonutti |
| 5,269,809 | A | 12/1993 | Hayhurst et al. |
| 5,273,524 | A | 12/1993 | Fox et al. |
| 5,275,166 | A | 1/1994 | Vaitekunas et al. |
| 5,281,235 | A | 1/1994 | Haber et al. |
| 5,282,803 | A | 2/1994 | Lackey |
| 5,282,832 | A | 2/1994 | Toso et al. |
| 5,282,861 | A | 2/1994 | Kaplan |
| 5,284,655 | A | 2/1994 | Bogdansky et al. |
| 5,285,655 | A | 2/1994 | Sung-Il et al. |
| 5,290,249 | A | 3/1994 | Foster et al. |
| 5,290,281 | A | 3/1994 | Tschakaloff |
| 5,295,994 | A | 3/1994 | Bonutti |
| 5,298,254 | A | 3/1994 | Prewett et al. |
| 2,696,338 | A | 4/1994 | Perrin |
| 5,304,119 | A | 4/1994 | Balaban et al. |
| 5,304,181 | A | 4/1994 | Caspari et al. |
| 5,306,280 | A | 4/1994 | Bregen et al. |
| 5,306,301 | A | 4/1994 | Graf et al. |
| 5,312,438 | A | 5/1994 | Johnson |
| 5,315,741 | A | 5/1994 | Dubberke |
| 5,318,588 | A | 6/1994 | Horzewski et al. |
| 5,320,611 | A | 6/1994 | Bonutti et al. |
| 5,322,505 | A | 6/1994 | Krause et al. |
| 5,324,308 | A | 6/1994 | Pierce |
| 5,326,361 | A | 7/1994 | Hollister |
| 5,328,480 | A | 7/1994 | Melker et al. |
| 5,329,846 | A | 7/1994 | Bonutti |
| 5,329,924 | A | 7/1994 | Bonutti |
| 5,330,468 | A | 7/1994 | Burkhart |
| 5,330,476 | A | 7/1994 | Hiot et al. |
| 5,330,486 | A | 7/1994 | Wilk |
| 5,330,497 | A | 7/1994 | Freitas et al. |
| 5,331,975 | A | 7/1994 | Bonutti |
| 5,334,146 | A | 8/1994 | Ozasa |
| 5,336,231 | A | 8/1994 | Adair |
| 5,336,240 | A | 8/1994 | Metzler et al. |
| 5,339,799 | A | 8/1994 | Kami et al. |
| 5,345,927 | A | 9/1994 | Bonutti |
| 5,349,956 | A | 9/1994 | Bonutti |
| 5,352,229 | A | 10/1994 | Goble et al. |
| 5,354,298 | A | 10/1994 | Lee et al. |
| 5,354,302 | A | 10/1994 | Ko |
| 5,356,413 | A | 10/1994 | Martins et al. |
| 5,360,450 | A | 11/1994 | Giannini |
| 5,366,480 | A | 11/1994 | Corriveau et al. |
| 5,370,646 | A | 12/1994 | Reese et al. |
| 5,370,660 | A | 12/1994 | Weinstein et al. |
| 5,370,662 | A | 12/1994 | Stone et al. |
| 5,372,146 | A | 12/1994 | Branch |
| 5,374,235 | A | 12/1994 | Ahrens |
| 5,376,101 | A | 12/1994 | Green et al. |
| 5,376,126 | A | 12/1994 | Lin |
| 5,379,759 | A | 1/1995 | Sewell, Jr. |
| 5,382,254 | A | 1/1995 | McGarry et al. |
| 5,383,883 | A | 1/1995 | Wilk et al. |
| 5,383,905 | A | 1/1995 | Golds et al. |
| 5,383,937 | A | 1/1995 | Mikhail |
| RE34,866 | E | 2/1995 | Kensey et al. |
| 5,390,683 | A | 2/1995 | Pisharodi |
| 5,391,171 | A | 2/1995 | Schmieding |
| 5,391,173 | A | 2/1995 | Wilk |
| RE34,871 | E | 3/1995 | McGuire et al. |
| 5,395,308 | A | 3/1995 | Fox et al. |
| 5,395,376 | A | 3/1995 | Caspari et al. |
| 5,397,311 | A | 3/1995 | Walker et al. |
| 5,397,331 | A | 3/1995 | Himpens et al. |
| 5,400,805 | A | 3/1995 | Warren |
| 5,403,312 | A | 4/1995 | Yates et al. |
| 5,403,317 | A | 4/1995 | Bonutti |
| 5,403,348 | A * | 4/1995 | Bonutti ........................ 606/232 |
| 5,405,359 | A | 4/1995 | Pierce |
| 5,411,523 | A | 5/1995 | Goble |
| 5,413,585 | A | 5/1995 | Pagedas |
| 5,415,663 | A | 5/1995 | Luckman et al. |
| 5,417,691 | A | 5/1995 | Hayhurst |
| 5,417,700 | A | 5/1995 | Egan |
| 5,417,701 | A | 5/1995 | Holmes |
| 5,417,712 | A | 5/1995 | Whittaker et al. |
| 5,423,796 | A | 6/1995 | Shikhman et al. |
| 5,423,819 | A | 6/1995 | Small et al. |
| 5,423,860 | A | 6/1995 | Lizardi et al. |
| 5,425,733 | A | 6/1995 | Schmieding |
| 5,431,670 | A | 7/1995 | Holmes |
| 5,439,470 | A | 8/1995 | Li |
| 5,441,502 | A | 8/1995 | Bartlett |
| 5,441,538 | A | 8/1995 | Bonutti |
| 5,443,482 | A | 8/1995 | Stone et al. |
| 5,443,512 | A | 8/1995 | Parr et al. |
| 5,445,615 | A | 8/1995 | Yoon |
| 5,447,503 | A | 9/1995 | Miller |
| 5,449,372 | A | 9/1995 | Schmaltz et al. |
| 5,449,382 | A | 9/1995 | Dayton |
| 5,451,235 | A | 9/1995 | Lock |
| 5,453,090 | A | 9/1995 | Martinez et al. |
| 5,454,365 | A | 10/1995 | Bonutti |
| 5,456,722 | A | 10/1995 | McLeod et al. |
| 5,458,653 | A | 10/1995 | Davidson |
| 5,462,549 | A | 10/1995 | Glock |
| 5,462,561 | A | 10/1995 | Voda |
| 5,464,424 | A | 11/1995 | O'Donnell, Jr. |
| 5,464,425 | A | 11/1995 | Skiba |
| 5,464,426 | A | 11/1995 | Bonutti |
| 5,464,427 | A | 11/1995 | Curtis et al. |
| 5,470,337 | A | 11/1995 | Moss |
| 5,472,444 | A | 12/1995 | Huebner et al. |
| 5,474,554 | A | 12/1995 | Ku |
| 5,474,559 | A | 12/1995 | Bertin et al. |
| 5,478,351 | A | 12/1995 | Meade et al. |
| 5,478,353 | A | 12/1995 | Yoon |
| 5,480,403 | A | 1/1996 | Lee et al. |
| 5,484,437 | A | 1/1996 | Michelson |
| 5,486,197 | A | 1/1996 | Le et al. |
| 5,487,844 | A | 1/1996 | Fujita |
| 5,488,958 | A | 2/1996 | Topel et al. |

(56) References Cited

U.S. PATENT DOCUMENTS

| | | |
|---|---|---|
| 5,492,697 A | 2/1996 | Boyan et al. |
| 5,496,292 A | 3/1996 | Burnham |
| 5,496,335 A | 3/1996 | Thomason et al. |
| 5,496,348 A | 3/1996 | Bonutti |
| 5,500,000 A | 3/1996 | Feagin et al. |
| 5,501,700 A | 3/1996 | Hirata |
| 5,504,977 A | 4/1996 | Weppner et al. |
| 5,505,735 A | 4/1996 | Li |
| 5,507,754 A | 4/1996 | Green et al. |
| 5,514,091 A | 5/1996 | Yoon |
| 5,514,153 A | 5/1996 | Bonutti |
| 5,520,700 A | 5/1996 | Beyar et al. |
| 5,522,844 A | 6/1996 | Johnson |
| 5,522,845 A | 6/1996 | Wenstrom, Jr. |
| 5,522,846 A | 6/1996 | Bonutti |
| 5,527,341 A | 6/1996 | Gogolewski et al. |
| 5,527,342 A | 6/1996 | Pietrzak et al. |
| 5,527,343 A | 6/1996 | Bonutti |
| 5,529,075 A | 6/1996 | Clark |
| 5,531,759 A | 7/1996 | Kensey et al. |
| 5,534,012 A | 7/1996 | Bonutti |
| 5,534,028 A | 7/1996 | Bao et al. |
| 5,540,718 A | 7/1996 | Bartlett |
| 5,542,423 A | 8/1996 | Bonutti |
| 5,542,947 A | 8/1996 | Treacy |
| 5,545,178 A | 8/1996 | Kensey et al. |
| 5,545,180 A | 8/1996 | Le et al. |
| 5,545,206 A | 8/1996 | Carson |
| 5,545,222 A | 8/1996 | Bonutti |
| 5,549,630 A | 8/1996 | Bonutti |
| 5,549,631 A | 8/1996 | Bonutti |
| 5,549,689 A | 8/1996 | Epstein et al. |
| 5,550,172 A | 8/1996 | Regula et al. |
| 2,215,943 A | 9/1996 | Collette |
| 5,556,402 A | 9/1996 | Xu |
| 5,562,668 A | 10/1996 | Johnson |
| 5,562,684 A | 10/1996 | Kammerer |
| 5,562,688 A | 10/1996 | Riza |
| 5,569,252 A | 10/1996 | Justin et al. |
| 5,569,259 A | 10/1996 | Ferrante et al. |
| 5,569,305 A | 10/1996 | Bonutti |
| 5,569,306 A | 10/1996 | Thal |
| 5,571,139 A | 11/1996 | Jenkins, Jr. |
| 5,571,196 A | 11/1996 | Stein |
| 5,573,517 A | 11/1996 | Bonutti et al. |
| 5,573,538 A | 11/1996 | Laboureau |
| 5,573,542 A | 11/1996 | Stevens |
| 5,575,801 A | 11/1996 | Habermeyer |
| 5,577,517 A | 11/1996 | Bonutti |
| 5,580,344 A | 12/1996 | Hasson |
| 5,584,835 A | 12/1996 | Greenfield |
| 5,584,860 A | 12/1996 | Goble et al. |
| 5,584,862 A | 12/1996 | Bonutti |
| 5,591,206 A | 1/1997 | Moufarrege |
| 5,593,422 A | 1/1997 | Muijs Van De Moer et al. |
| 5,593,425 A | 1/1997 | Bonutti et al. |
| 5,593,625 A | 1/1997 | Riebel et al. |
| 5,601,557 A | 2/1997 | Hayhurst |
| 5,601,558 A | 2/1997 | Torrie et al. |
| 5,601,565 A | 2/1997 | Huebner |
| 5,601,595 A | 2/1997 | Smith |
| 5,607,427 A | 3/1997 | Tschakaloff |
| 5,609,595 A | 3/1997 | Pennig |
| 5,609,635 A | 3/1997 | Michelson |
| 5,618,314 A | 4/1997 | Harwin et al. |
| 5,620,448 A | 4/1997 | Puddu |
| 5,620,461 A | 4/1997 | Muijs Van De Moer et al. |
| 5,624,462 A | 4/1997 | Bonutti |
| 5,624,463 A | 4/1997 | Stone et al. |
| 5,626,612 A | 5/1997 | Bartlett |
| 5,626,614 A | 5/1997 | Hart |
| 5,626,718 A | 5/1997 | Philippe et al. |
| 5,628,751 A | 5/1997 | Sander et al. |
| 5,630,824 A | 5/1997 | Hart |
| 5,634,926 A | 6/1997 | Jobe |
| 5,643,274 A | 7/1997 | Sander et al. |
| 5,643,293 A | 7/1997 | Kogasaka et al. |
| 5,643,295 A | 7/1997 | Yoon |
| 5,643,320 A | 7/1997 | Lower et al. |
| 5,643,321 A | 7/1997 | McDevitt |
| 5,644,002 A | 7/1997 | Cooper et al. |
| 5,645,553 A | 7/1997 | Kolesa et al. |
| 5,645,588 A | 7/1997 | Graf et al. |
| 5,645,597 A | 7/1997 | Krapiva |
| 5,645,599 A | 7/1997 | Samani |
| 5,649,955 A | 7/1997 | Hashimoto et al. |
| 5,649,963 A | 7/1997 | McDevitt |
| 5,651,377 A | 7/1997 | O'Donnell, Jr. |
| 5,658,313 A | 8/1997 | Thal |
| 5,660,225 A | 8/1997 | Saffran |
| 5,662,658 A | 9/1997 | Wenstrom, Jr. |
| 5,662,710 A | 9/1997 | Bonutti |
| 5,665,089 A | 9/1997 | Dall et al. |
| 5,665,109 A | 9/1997 | Yoon |
| 5,665,112 A | 9/1997 | Thal |
| 5,667,513 A | 9/1997 | Torrie et al. |
| 5,667,520 A | 9/1997 | Bonutti |
| 5,669,909 A | 9/1997 | Zdeblick et al. |
| 5,669,917 A | 9/1997 | Sauer et al. |
| 5,674,240 A | 10/1997 | Bonutti |
| 5,681,310 A | 10/1997 | Yuan et al. |
| 5,681,333 A | 10/1997 | Burkhart et al. |
| 5,681,351 A | 10/1997 | Jamiolkowski et al. |
| 5,681,352 A | 10/1997 | Clancy, III et al. |
| 5,682,886 A | 11/1997 | Delp et al. |
| 5,683,401 A | 11/1997 | Schmieding et al. |
| 5,683,418 A | 11/1997 | Luscombe et al. |
| 5,683,469 A | 11/1997 | Johnson et al. |
| 5,685,820 A | 11/1997 | Riek et al. |
| 5,685,826 A | 11/1997 | Bonutti |
| 5,688,283 A | 11/1997 | Knapp |
| 5,690,654 A | 11/1997 | Ovil |
| 5,690,655 A | 11/1997 | Hart et al. |
| 5,690,674 A | 11/1997 | Diaz |
| 5,690,676 A | 11/1997 | DiPoto et al. |
| 5,693,055 A | 12/1997 | Zahiri et al. |
| 5,694,951 A | 12/1997 | Bonutti |
| 5,697,950 A | 12/1997 | Fucci et al. |
| 5,702,397 A | 12/1997 | Goble et al. |
| 5,702,462 A | 12/1997 | Oberlander |
| 5,707,390 A | 1/1998 | Bonutti |
| 5,707,395 A | 1/1998 | Li |
| 5,713,897 A | 2/1998 | Goble et al. |
| 5,713,903 A | 2/1998 | Sander et al. |
| 5,713,921 A | 2/1998 | Bonutti |
| 5,715,836 A | 2/1998 | Kliegis et al. |
| 5,716,325 A | 2/1998 | Bonutti |
| 5,718,717 A | 2/1998 | Bonutti |
| 5,720,747 A | 2/1998 | Burke |
| 5,720,753 A | 2/1998 | Sander et al. |
| 5,722,978 A | 3/1998 | Jenkins, Jr. |
| 5,723,016 A | 3/1998 | Minns et al. |
| 5,725,529 A | 3/1998 | Nicholson et al. |
| 5,725,541 A | 3/1998 | Anspach, III et al. |
| 5,725,556 A | 3/1998 | Moser et al. |
| 5,725,557 A | 3/1998 | Gatturna et al. |
| 5,725,582 A | 3/1998 | Bevan |
| 5,730,747 A | 3/1998 | Ek et al. |
| 5,733,306 A | 3/1998 | Bonutti |
| 5,735,875 A | 4/1998 | Bonutti et al. |
| 5,735,877 A | 4/1998 | Pagedas |
| 5,735,899 A | 4/1998 | Schwartz et al. |
| 5,741,268 A | 4/1998 | Schutz |
| 5,741,282 A | 4/1998 | Anspach, III et al. |
| 5,752,952 A | 5/1998 | Adamson |
| 5,752,974 A | 5/1998 | Rhee et al. |
| 5,755,809 A | 5/1998 | Cohen et al. |
| 5,762,458 A | 6/1998 | Wang et al. |
| 5,763,416 A | 6/1998 | Bonadio et al. |
| 5,766,221 A | 6/1998 | Benderev et al. |
| 5,766,251 A | 6/1998 | Koshino |
| 5,769,854 A | 6/1998 | Bastian et al. |
| 5,769,894 A | 6/1998 | Ferragamo |
| 5,772,672 A | 6/1998 | Toy et al. |

(56) References Cited

U.S. PATENT DOCUMENTS

| | | |
|---|---|---|
| 5,776,151 A | 7/1998 | Chan |
| 5,779,706 A | 7/1998 | Tschakaloff |
| 5,779,719 A | 7/1998 | Klein et al. |
| 5,779,728 A | 7/1998 | Lunsford et al. |
| 5,782,862 A | 7/1998 | Bonutti |
| 5,782,925 A | 7/1998 | Collazo et al. |
| 5,785,713 A | 7/1998 | Jobe |
| 5,792,096 A | 8/1998 | Rentmeester et al. |
| 5,797,931 A | 8/1998 | Bito et al. |
| 5,797,963 A | 8/1998 | McDevitt |
| 5,800,537 A | 9/1998 | Bell |
| 5,800,544 A | 9/1998 | Demopulos |
| 5,806,518 A | 9/1998 | Mittelstadt |
| 5,807,403 A | 9/1998 | Beyar et al. |
| 5,810,827 A | 9/1998 | Haines et al. |
| 5,810,849 A | 9/1998 | Kontos |
| 5,810,853 A | 9/1998 | Yoon |
| 5,810,884 A | 9/1998 | Kim |
| 5,814,071 A | 9/1998 | McDevitt et al. |
| 5,814,072 A | 9/1998 | Bonutti |
| 5,814,073 A | 9/1998 | Bonutti |
| 5,817,107 A | 10/1998 | Schaller |
| 5,823,994 A | 10/1998 | Sharkey et al. |
| 5,824,009 A | 10/1998 | Fukuda et al. |
| 5,827,318 A | 10/1998 | Bonutti |
| 5,830,125 A | 11/1998 | Scribner et al. |
| 5,836,897 A | 11/1998 | Sakural et al. |
| 5,836,948 A | 11/1998 | Zucherman et al. |
| 5,839,899 A | 11/1998 | Robinson |
| 5,843,178 A | 12/1998 | Vanney et al. |
| 5,845,645 A | 12/1998 | Bonutti |
| 5,851,185 A | 12/1998 | Berns |
| 5,853,422 A | 12/1998 | Huebsch et al. |
| 5,860,997 A | 1/1999 | Bonutti |
| 5,865,834 A | 2/1999 | McGuire |
| 5,866,634 A | 2/1999 | Tokushige |
| 5,868,749 A | 2/1999 | Reed |
| 5,871,018 A | 2/1999 | Delp et al. |
| 5,873,891 A | 2/1999 | Sohn |
| 5,874,235 A | 2/1999 | Chan |
| 5,879,372 A | 3/1999 | Bartlett |
| 5,888,196 A | 3/1999 | Bonutti |
| 5,888,219 A | 3/1999 | Bonutti |
| 5,891,166 A | 4/1999 | Schervinsky |
| 5,891,168 A | 4/1999 | Thal |
| 5,893,880 A | 4/1999 | Egan et al. |
| 5,895,426 A | 4/1999 | Scarborough et al. |
| 5,897,559 A | 4/1999 | Masini |
| 5,897,574 A | 4/1999 | Bonutti |
| 5,899,911 A | 5/1999 | Carter |
| 5,899,921 A | 5/1999 | Caspari et al. |
| 5,902,321 A | 5/1999 | Caspari et al. |
| 5,906,579 A | 5/1999 | Vander Salm et al. |
| 5,906,616 A | 5/1999 | Pavlov et al. |
| 5,906,625 A | 5/1999 | Bito et al. |
| 5,908,429 A | 6/1999 | Yoon |
| 5,911,721 A | 6/1999 | Nicholson et al. |
| 5,916,221 A | 6/1999 | Hodorek et al. |
| 5,918,604 A | 7/1999 | Whelan |
| 5,919,193 A | 7/1999 | Slavitt |
| 5,919,194 A | 7/1999 | Anderson |
| 5,919,208 A | 7/1999 | Valenti |
| 5,919,215 A | 7/1999 | Wiklund et al. |
| 5,921,986 A | 7/1999 | Bonutti |
| 5,925,064 A | 7/1999 | Meyers et al. |
| 5,928,244 A | 7/1999 | Tovey et al. |
| 5,928,267 A | 7/1999 | Bonutti et al. |
| 5,931,838 A | 8/1999 | Vito |
| 5,931,869 A | 8/1999 | Boucher et al. |
| 5,935,094 A | 8/1999 | Zupkas |
| 5,935,131 A | 8/1999 | Bonutti |
| 5,935,149 A | 8/1999 | Ek |
| 5,940,942 A | 8/1999 | Fong |
| 5,941,900 A | 8/1999 | Bonutti |
| 5,941,901 A | 8/1999 | Egan |
| 5,947,982 A | 9/1999 | Duran |
| 5,948,000 A | 9/1999 | Larsen et al. |
| 5,948,001 A | 9/1999 | Larsen |
| 5,948,002 A | 9/1999 | Bonutti |
| 5,951,590 A | 9/1999 | Goldfarb |
| 5,954,739 A | 9/1999 | Bonutti |
| 5,957,953 A | 9/1999 | DiPoto et al. |
| 5,961,499 A | 10/1999 | Bonutti |
| 5,961,521 A | 10/1999 | Roger |
| 5,961,538 A | 10/1999 | Pedlick et al. |
| 5,961,554 A | 10/1999 | Janson et al. |
| 5,964,765 A | 10/1999 | Fenton, Jr. et al. |
| 5,964,769 A | 10/1999 | Wagner et al. |
| 5,968,044 A | 10/1999 | Nicholson et al. |
| 5,968,046 A | 10/1999 | Castleman |
| 5,968,047 A | 10/1999 | Reed |
| 5,980,520 A | 11/1999 | Vancaillie |
| 5,980,558 A | 11/1999 | Wiley |
| 5,980,559 A | 11/1999 | Bonutti |
| 5,984,929 A | 11/1999 | Bashiri et al. |
| 5,984,967 A | 11/1999 | Zdeblick et al. |
| 5,989,282 A | 11/1999 | Bonutti |
| 5,989,289 A | 11/1999 | Coates et al. |
| 5,993,458 A | 11/1999 | Vaitekunas et al. |
| 5,993,477 A | 11/1999 | Vaitekunas et al. |
| 6,007,537 A | 12/1999 | Burkinshaw et al. |
| 6,007,567 A | 12/1999 | Bonutti |
| 6,007,580 A | 12/1999 | Lehto et al. |
| 6,008,433 A | 12/1999 | Stone |
| 6,010,525 A | 1/2000 | Bonutti et al. |
| 6,010,526 A | 1/2000 | Sandstrom et al. |
| 6,013,853 A | 1/2000 | Athanasiou et al. |
| 6,017,305 A | 1/2000 | Bonutti |
| 6,017,321 A | 1/2000 | Boone |
| 6,024,746 A | 2/2000 | Katz |
| 6,033,410 A | 3/2000 | McLean et al. |
| 6,033,429 A | 3/2000 | Magovern |
| 6,033,430 A | 3/2000 | Bonutti |
| 6,042,596 A | 3/2000 | Bonutti |
| 6,045,551 A | 4/2000 | Bonutti |
| 6,050,998 A | 4/2000 | Fletcher et al. |
| 6,056,751 A | 5/2000 | Fenton, Jr. |
| 6,056,754 A | 5/2000 | Haines et al. |
| 6,056,772 A | 5/2000 | Bonutti |
| 6,056,773 A | 5/2000 | Bonutti |
| 6,059,797 A | 5/2000 | Mears |
| 6,059,817 A | 5/2000 | Bonutti et al. |
| 6,059,827 A | 5/2000 | Fenton |
| 6,059,831 A | 5/2000 | Braslow et al. |
| 6,063,095 A | 5/2000 | Wang et al. |
| 6,066,151 A | 5/2000 | Miyawaki et al. |
| 6,066,160 A | 5/2000 | Colvin et al. |
| 6,066,166 A | 5/2000 | Bischoff et al. |
| 6,066,175 A | 5/2000 | Henderson et al. |
| 6,068,637 A | 5/2000 | Popov et al. |
| 6,068,648 A | 5/2000 | Cole et al. |
| 6,074,409 A | 6/2000 | Goldfarb |
| 6,077,277 A | 6/2000 | Mollenauer et al. |
| 6,077,292 A | 6/2000 | Bonutti |
| 6,080,161 A | 6/2000 | Eaves, III et al. |
| 6,083,244 A | 7/2000 | Lubbers et al. |
| 6,083,522 A | 7/2000 | Chu et al. |
| 6,086,593 A | 7/2000 | Bonutti |
| 6,086,608 A | 7/2000 | Ek et al. |
| 6,090,072 A | 7/2000 | Kratoska et al. |
| 6,099,531 A | 8/2000 | Bonutti |
| 6,099,537 A | 8/2000 | Sugai et al. |
| 6,099,547 A | 8/2000 | Gellman et al. |
| 6,099,550 A | 8/2000 | Yoon |
| 6,099,552 A | 8/2000 | Adams |
| 6,102,850 A | 8/2000 | Wang et al. |
| 6,102,928 A | 8/2000 | Bonutti |
| 6,102,950 A | 8/2000 | Vaccaro |
| 6,102,955 A | 8/2000 | Mendes et al. |
| 6,106,529 A | 8/2000 | Techiera |
| 6,106,545 A | 8/2000 | Egan |
| 6,110,188 A | 8/2000 | Narciso, Jr. |
| 6,110,207 A | 8/2000 | Eichhorn et al. |
| 6,117,160 A | 9/2000 | Bonutti |

(56) References Cited

U.S. PATENT DOCUMENTS

| | | |
|---|---|---|
| 6,120,536 A | 9/2000 | Ding et al. |
| 6,123,710 A | 9/2000 | Pinczewski et al. |
| 6,125,574 A | 10/2000 | Ganaja et al. |
| 6,126,677 A | 10/2000 | Ganaja et al. |
| 6,132,468 A | 10/2000 | Mansmann |
| 6,132,472 A | 10/2000 | Bonutti |
| 6,139,320 A | 10/2000 | Hahn |
| RE36,974 E | 11/2000 | Bonutti |
| 6,146,385 A | 11/2000 | Torrie et al. |
| 6,149,669 A | 11/2000 | Li |
| 6,152,949 A | 11/2000 | Bonutti |
| 6,155,756 A | 12/2000 | Mericle et al. |
| 6,156,070 A | 12/2000 | Incavo et al. |
| 6,159,224 A | 12/2000 | Yoon |
| 6,159,234 A | 12/2000 | Bonutti et al. |
| 6,171,236 B1 | 1/2001 | Bonutti |
| 6,171,299 B1 | 1/2001 | Bonutti |
| 6,171,307 B1 | 1/2001 | Orlich |
| 6,171,340 B1 | 1/2001 | McDowell |
| 6,174,313 B1 | 1/2001 | Bonutti |
| 6,174,314 B1 | 1/2001 | Waddell |
| 6,174,324 B1 | 1/2001 | Egan et al. |
| 6,179,840 B1 | 1/2001 | Bowman |
| 6,179,850 B1 | 1/2001 | Goradia |
| 6,187,008 B1 | 2/2001 | Hamman |
| 6,187,023 B1 | 2/2001 | Bonutti |
| 6,190,400 B1 | 2/2001 | Van De Moer et al. |
| 6,190,401 B1 | 2/2001 | Green |
| 6,193,754 B1 | 2/2001 | Seedhom |
| 6,200,322 B1 | 3/2001 | Branch et al. |
| 6,200,329 B1 | 3/2001 | Fung et al. |
| 6,203,565 B1 | 3/2001 | Bonutti et al. |
| 6,214,051 B1 | 4/2001 | Badorf et al. |
| 6,217,591 B1 | 4/2001 | Egan et al. |
| 6,217,617 B1 | 4/2001 | Bonutti |
| 6,224,593 B1 | 5/2001 | Ryan |
| 6,224,630 B1 | 5/2001 | Bao et al. |
| 6,228,086 B1 | 5/2001 | Wahl et al. |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,749 B1 | 6/2001 | Rayhanabad |
| 6,241,771 B1 | 6/2001 | Gresser et al. |
| 6,258,091 B1 | 7/2001 | Sevrain et al. |
| 6,261,295 B1 | 7/2001 | Nicholson |
| 6,264,675 B1 | 7/2001 | Brotz |
| 6,267,761 B1 | 7/2001 | Ryan |
| 6,273,717 B1 | 8/2001 | Hahn et al. |
| 6,277,136 B1 | 8/2001 | Bonutti |
| 6,280,474 B1 | 8/2001 | Cassidy et al. |
| 6,286,746 B1 | 9/2001 | Egan et al. |
| 6,287,325 B1 | 9/2001 | Bonutti |
| 6,293,961 B2 | 9/2001 | Schwartz et al. |
| 6,296,646 B1 | 10/2001 | Williamson |
| 6,306,159 B1 | 10/2001 | Schwartz et al. |
| 6,309,405 B1 | 10/2001 | Bonutti |
| 6,312,448 B1 | 11/2001 | Bonutti |
| 6,319,252 B1 | 11/2001 | McDevitt et al. |
| 6,319,271 B1 | 11/2001 | Schwartz et al. |
| 6,325,806 B1 | 12/2001 | Fox |
| 6,338,730 B1 | 1/2002 | Bonutti et al. |
| 6,340,365 B2 | 1/2002 | Dittrich et al. |
| 6,342,075 B1 | 1/2002 | Macarthur |
| 6,348,056 B1 | 2/2002 | Bates et al. |
| 6,358,252 B1 | 3/2002 | Shapira |
| 6,358,266 B1 | 3/2002 | Bonutti |
| 6,358,271 B1 | 3/2002 | Egan et al. |
| 6,361,565 B1 | 3/2002 | Bonutti |
| 6,364,897 B1 | 4/2002 | Bonutti |
| 6,368,325 B1 | 4/2002 | McKinley et al. |
| 6,368,326 B1 | 4/2002 | Dakin et al. |
| 6,368,343 B1 | 4/2002 | Bonutti et al. |
| 6,371,957 B1 | 4/2002 | Amrein et al. |
| 6,398,797 B2 | 6/2002 | Bombard et al. |
| 6,409,742 B1 | 6/2002 | Fulton, III |
| 6,409,743 B1 | 6/2002 | Fenton, Jr. |
| 6,409,764 B1 | 6/2002 | White et al. |
| 6,419,704 B1 | 7/2002 | Ferree |
| 6,423,063 B1 | 7/2002 | Bonutti |
| 6,423,088 B1 | 7/2002 | Fenton |
| 6,425,919 B1 | 7/2002 | Lambrecht |
| 6,428,562 B2 | 8/2002 | Bonutti |
| 6,432,115 B1 | 8/2002 | Mollenauer et al. |
| 6,447,516 B1 | 9/2002 | Bonutti |
| 6,450,985 B1 | 9/2002 | Schoelling et al. |
| 6,451,042 B1 | 9/2002 | Bonutti |
| 6,461,360 B1 | 10/2002 | Adams |
| 6,464,713 B2 | 10/2002 | Bonutti |
| 6,468,289 B1 | 10/2002 | Bonutti |
| 6,468,293 B2 | 10/2002 | Bonutti et al. |
| 6,471,715 B1 | 10/2002 | Weiss |
| 6,471,724 B2 | 10/2002 | Zdeblick et al. |
| 6,475,230 B1 | 11/2002 | Bonutti |
| 6,482,209 B1 | 11/2002 | Engh et al. |
| 6,488,196 B1 | 12/2002 | Fenton |
| 6,500,179 B1 | 12/2002 | Masini |
| 6,500,195 B2 | 12/2002 | Bonutti |
| 6,503,259 B2 | 1/2003 | Huxel et al. |
| 6,503,267 B2 | 1/2003 | Bonutti et al. |
| 6,503,277 B2 | 1/2003 | Bonutti |
| 6,527,774 B2 | 3/2003 | Lieberman |
| 6,530,933 B1 | 3/2003 | Yeung et al. |
| 6,535,764 B2 | 3/2003 | Imran et al. |
| 6,540,786 B2 | 4/2003 | Chibrac et al. |
| 6,543,455 B2 | 4/2003 | Bonutti |
| 6,544,267 B1 | 4/2003 | Cole et al. |
| 6,545,390 B1 | 4/2003 | Hahn et al. |
| 6,547,792 B1 | 4/2003 | Tsuji et al. |
| 6,551,304 B1 | 4/2003 | Whalen et al. |
| 6,554,852 B1 | 4/2003 | Oberlander |
| 6,557,426 B2 | 5/2003 | Reinemann et al. |
| 6,558,390 B2 | 5/2003 | Cragg |
| 6,562,043 B1 | 5/2003 | Chan |
| 6,568,313 B2 | 5/2003 | Fukui et al. |
| 6,569,167 B1 | 5/2003 | Bobechko et al. |
| 6,569,187 B1 | 5/2003 | Bonutti |
| 6,572,635 B1 | 6/2003 | Bonutti |
| 6,575,980 B1 | 6/2003 | Robie et al. |
| 6,575,982 B1 | 6/2003 | Bonutti |
| D477,776 S | 7/2003 | Pontaoe |
| 6,585,750 B2 | 7/2003 | Bonutti |
| 6,585,764 B2 | 7/2003 | Wright et al. |
| 6,589,248 B1 | 7/2003 | Hughes |
| 6,589,281 B2 | 7/2003 | Hyde, Jr. |
| 6,592,531 B2 | 7/2003 | Bonutti |
| 6,592,609 B1 | 7/2003 | Bonutti |
| 6,594,517 B1 | 7/2003 | Nevo |
| 6,605,090 B1 | 8/2003 | Trieu et al. |
| 6,607,534 B2 | 8/2003 | Bonutti |
| 6,610,080 B2 | 8/2003 | Morgan |
| 6,616,696 B1 | 9/2003 | Merchant |
| 6,618,910 B1 | 9/2003 | Pontaoe |
| 6,620,181 B1 | 9/2003 | Bonutti |
| 6,623,486 B1 | 9/2003 | Weaver |
| 6,623,487 B1 | 9/2003 | Goshert |
| 6,626,944 B1 | 9/2003 | Taylor |
| 6,630,000 B1 | 10/2003 | Bonutti |
| 6,632,245 B2 | 10/2003 | Kim |
| 6,635,073 B2 | 10/2003 | Bonutti |
| 6,638,279 B2 | 10/2003 | Bonutti |
| 6,638,309 B2 | 10/2003 | Bonutti |
| 6,641,592 B1 | 11/2003 | Sauer et al. |
| 6,645,227 B2 | 11/2003 | Fallin et al. |
| 6,652,532 B2 | 11/2003 | Bonutti |
| 6,652,587 B2 | 11/2003 | Felt et al. |
| 6,666,877 B2 | 12/2003 | Morgan et al. |
| 6,669,705 B2 | 12/2003 | Westhaver et al. |
| 6,679,888 B2 | 1/2004 | Green et al. |
| 6,685,750 B1 | 2/2004 | Plos et al. |
| 6,699,240 B2 | 3/2004 | Francischelli |
| 6,702,821 B2 | 3/2004 | Bonutti |
| 6,702,856 B2 | 3/2004 | Bonutti |
| 6,705,179 B1 | 3/2004 | Mohtasham |
| 6,709,457 B1 | 3/2004 | Otte |

(56) References Cited

U.S. PATENT DOCUMENTS

| | | |
|---|---|---|
| 6,719,765 B2 | 4/2004 | Bonutti |
| 6,719,797 B1 | 4/2004 | Ferree |
| 6,719,803 B2 | 4/2004 | Bonutti |
| 6,722,552 B2 | 4/2004 | Fenton |
| 6,723,102 B2 | 4/2004 | Johnson et al. |
| 6,733,506 B1 | 5/2004 | McDevitt et al. |
| 6,733,531 B1 | 5/2004 | Trieu |
| 6,736,853 B2 | 5/2004 | Bonutti |
| 6,755,865 B2 | 6/2004 | Tarabishy |
| 6,764,514 B1 | 7/2004 | Li et al. |
| 6,770,078 B2 | 8/2004 | Bonutti |
| 6,776,938 B2 | 8/2004 | Bonutti |
| 6,780,198 B1 | 8/2004 | Gregoire et al. |
| 6,786,989 B2 | 9/2004 | Torriani et al. |
| 6,796,003 B1 | 9/2004 | Marvel |
| 6,818,010 B2 | 11/2004 | Eichhorn et al. |
| 6,823,871 B2 | 11/2004 | Schmieding |
| 6,827,723 B2 | 12/2004 | Carson |
| 6,835,198 B2 | 12/2004 | Bonutti |
| 6,860,885 B2 | 3/2005 | Bonutti |
| 6,860,904 B2 | 3/2005 | Bonutti |
| 6,878,167 B2 | 4/2005 | Ferree |
| 6,890,334 B2 | 5/2005 | Brace et al. |
| 6,893,434 B2 | 5/2005 | Fenton et al. |
| 6,899,722 B2 | 5/2005 | Bonutti |
| 6,905,517 B2 | 6/2005 | Bonutti |
| 6,908,466 B1 | 6/2005 | Bonutti et al. |
| 6,913,666 B1 | 7/2005 | Aeschlimann et al. |
| 6,916,321 B2 | 7/2005 | TenHuisen |
| 6,921,264 B2 | 7/2005 | Mayer et al. |
| 6,923,824 B2 | 8/2005 | Morgan et al. |
| 6,932,835 B2 | 8/2005 | Bonutti |
| 6,942,684 B2 | 9/2005 | Bonutti |
| 6,944,111 B2 | 9/2005 | Nakamura et al. |
| 6,955,540 B2 | 10/2005 | Mayer et al. |
| 6,955,683 B2 | 10/2005 | Bonutti |
| 6,958,077 B2 | 10/2005 | Suddaby |
| 6,981,983 B1 | 1/2006 | Rosenblatt et al. |
| 6,989,029 B2 | 1/2006 | Bonutti |
| 6,990,982 B1 | 1/2006 | Bonutti |
| 6,997,940 B2 | 2/2006 | Bonutti |
| 7,001,385 B2 | 2/2006 | Bonutti |
| 7,001,411 B1 | 2/2006 | Dean |
| 7,004,959 B2 | 2/2006 | Bonutti |
| 7,008,226 B2 | 3/2006 | Mayer et al. |
| 7,018,380 B2 | 3/2006 | Cole |
| 7,033,379 B2 | 4/2006 | Peterson |
| 7,048,741 B2 | 5/2006 | Swanson |
| 7,048,755 B2 | 5/2006 | Bonutti |
| 7,066,960 B1 | 6/2006 | Dickman |
| 7,070,557 B2 | 7/2006 | Bonutti |
| 7,087,073 B2 | 8/2006 | Bonutti |
| 7,090,111 B2 | 8/2006 | Egan et al. |
| 7,094,251 B2 | 8/2006 | Bonutti |
| 7,104,996 B2 | 9/2006 | Bonutti |
| 7,114,500 B2 | 10/2006 | Bonutti |
| 7,128,753 B1 | 10/2006 | Bonutti et al. |
| 7,128,763 B1 | 10/2006 | Blatt |
| 7,134,437 B2 | 11/2006 | Bonutti |
| 7,147,652 B2 | 12/2006 | Bonutti et al. |
| 7,153,312 B1 | 12/2006 | Torrie et al. |
| 7,160,405 B2 | 1/2007 | Aeschlimann et al. |
| 7,179,259 B1 | 2/2007 | Gibbs |
| 7,192,448 B2 | 3/2007 | Ferree |
| 7,208,013 B1 | 4/2007 | Bonutti |
| 7,217,273 B2 | 5/2007 | Bonutti |
| 7,217,279 B2 | 5/2007 | Reese |
| 7,217,290 B2 | 5/2007 | Bonutti |
| 7,241,297 B2 | 7/2007 | Shaolian et al. |
| 7,250,051 B2 | 7/2007 | Francischelli |
| 7,252,685 B2 | 8/2007 | Bindseil et al. |
| 7,273,497 B2 | 9/2007 | Ferree |
| 7,311,719 B2 | 12/2007 | Bonutti |
| 7,329,263 B2 | 2/2008 | Bonutti |
| 7,335,205 B2 | 2/2008 | Aeshclimann |
| 7,371,240 B2 | 5/2008 | Pinczewski et al. |
| 7,429,266 B2 | 9/2008 | Bonutti |
| 7,445,634 B2 | 11/2008 | Trieu |
| 7,462,200 B2 | 12/2008 | Bonutti |
| 7,481,825 B2 | 1/2009 | Bonutti |
| 7,481,831 B2 | 1/2009 | Bonutti |
| 7,510,557 B1 | 3/2009 | Bonutti |
| 7,510,895 B2 | 3/2009 | Raterman |
| 7,610,557 B2 | 10/2009 | McLennan et al. |
| 7,615,054 B1 | 11/2009 | Bonutti |
| 7,635,390 B1 | 12/2009 | Bonutti |
| 7,708,740 B1 | 5/2010 | Bonutti |
| 7,708,741 B1 | 5/2010 | Bonutti |
| 7,727,283 B2 | 6/2010 | Bonutti |
| 7,749,229 B1 | 7/2010 | Bonutti |
| 7,780,670 B2 | 8/2010 | Bonutti |
| 7,806,896 B1 | 10/2010 | Bonutti |
| 7,806,897 B1 | 10/2010 | Bonutti |
| 7,828,852 B2 | 11/2010 | Bonutti |
| 7,837,736 B2 | 11/2010 | Bonutti |
| 7,854,750 B2 | 12/2010 | Bonutti |
| 7,879,072 B2 | 2/2011 | Bonutti |
| 7,891,691 B2 | 2/2011 | Bearey |
| 7,892,236 B1 | 2/2011 | Bonutti |
| 7,892,261 B2 | 2/2011 | Bonutti |
| 7,896,880 B2 | 3/2011 | Bonutti |
| 7,931,690 B1 | 4/2011 | Bonutti |
| 7,959,635 B1 | 6/2011 | Bonutti |
| 7,967,820 B2 | 6/2011 | Bonutti |
| RE43,143 E | 1/2012 | Hayhurst |
| 8,092,462 B2 | 1/2012 | Pinczewski et al. |
| 8,128,669 B2 | 3/2012 | Bonutti |
| 8,133,229 B1 | 3/2012 | Bonutti |
| 8,140,982 B2 | 3/2012 | Hamilton, II et al. |
| 8,147,514 B2 | 4/2012 | Bonutti |
| 8,162,977 B2 | 4/2012 | Bonutti et al. |
| 8,425,522 B2 | 4/2013 | Bonutti |
| 8,486,066 B2 | 7/2013 | Bonutti |
| 8,496,657 B2 | 7/2013 | Bonutti et al. |
| 8,617,185 B2 | 12/2013 | Bonutti |
| 8,623,030 B2 | 1/2014 | Bonutti |
| 8,632,552 B2 | 1/2014 | Bonutti |
| 8,641,726 B2 | 2/2014 | Bonutti |
| 8,690,944 B2 | 4/2014 | Bonutti |
| 2001/0002440 A1 | 5/2001 | Bonutti |
| 2001/0009250 A1 | 7/2001 | Herman et al. |
| 2001/0023371 A1 | 9/2001 | Bonutti |
| 2001/0041916 A1 | 11/2001 | Bonutti |
| 2002/0016593 A1 | 2/2002 | Hearn et al. |
| 2002/0016633 A1 | 2/2002 | Lin et al. |
| 2002/0019649 A1 | 2/2002 | Sikora |
| 2002/0026244 A1 | 2/2002 | Trieu |
| 2002/0029055 A1 | 3/2002 | Bonutti |
| 2002/0029083 A1 | 3/2002 | Zucherman et al. |
| 2002/0029084 A1 | 3/2002 | Paul et al. |
| 2002/0040246 A1 | 4/2002 | Bonutti |
| 2002/0045902 A1 | 4/2002 | Bonutti |
| 2002/0062153 A1 | 5/2002 | Paul et al. |
| 2002/0103495 A1 | 8/2002 | Cole |
| 2002/0123750 A1 | 9/2002 | Eisermann et al. |
| 2002/0138150 A1 | 9/2002 | Leclercq |
| 2002/0183762 A1 | 12/2002 | Anderson et al. |
| 2002/0188301 A1 | 12/2002 | Dallara et al. |
| 2003/0009147 A1 | 1/2003 | Bonutti |
| 2003/0023260 A1 | 1/2003 | Bonutti |
| 2003/0032975 A1 | 2/2003 | Bonutti |
| 2003/0039196 A1 | 2/2003 | Nakamura et al. |
| 2003/0040758 A1 | 2/2003 | Wang et al. |
| 2003/0065361 A1 | 4/2003 | Dreyfuss |
| 2003/0105474 A1 | 6/2003 | Bonutti |
| 2003/0118518 A1 | 6/2003 | Hahn et al. |
| 2003/0158582 A1 | 8/2003 | Bonutti et al. |
| 2003/0167072 A1 | 9/2003 | Oberlander |
| 2003/0181800 A1 | 9/2003 | Bonutti |
| 2003/0195530 A1 | 10/2003 | Thill |
| 2003/0195565 A1 | 10/2003 | Bonutti |
| 2003/0204204 A1 | 10/2003 | Bonutti |
| 2003/0216742 A1 | 11/2003 | Wetzler et al. |
| 2003/0225438 A1 | 12/2003 | Bonutti et al. |

(56) References Cited

U.S. PATENT DOCUMENTS

| | | |
|---|---|---|
| 2003/0229361 A1 | 12/2003 | Jackson |
| 2004/0010287 A1 | 1/2004 | Bonutti |
| 2004/0030341 A1 | 2/2004 | Aeschlimann et al. |
| 2004/0034357 A1 | 2/2004 | Beane et al. |
| 2004/0097794 A1 | 5/2004 | Bonutti |
| 2004/0097939 A1 | 5/2004 | Bonutti |
| 2004/0098016 A1 | 5/2004 | Bonutti |
| 2004/0098050 A1 | 5/2004 | Foerster et al. |
| 2004/0127930 A1 | 7/2004 | Bonutti |
| 2004/0138689 A1 | 7/2004 | Bonutti |
| 2004/0138690 A1 | 7/2004 | Bonutti |
| 2004/0138703 A1 | 7/2004 | Alleyne |
| 2004/0143285 A1 | 7/2004 | Bonutti |
| 2004/0143334 A1 | 7/2004 | Ferree |
| 2004/0167548 A1 | 8/2004 | Bonutti |
| 2004/0172033 A1 | 9/2004 | Bonutti |
| 2004/0193181 A1 | 9/2004 | Bonutti |
| 2004/0220616 A1 | 11/2004 | Bonutti |
| 2004/0225325 A1 | 11/2004 | Bonutti |
| 2004/0230223 A1 | 11/2004 | Bonutti |
| 2004/0236374 A1 | 11/2004 | Bonutti et al. |
| 2004/0254582 A1 | 12/2004 | Bonutti |
| 2005/0033366 A1 | 2/2005 | Cole |
| 2005/0038514 A1 | 2/2005 | Helm et al. |
| 2005/0043796 A1 | 2/2005 | Grant et al. |
| 2005/0071012 A1 | 3/2005 | Serhan et al. |
| 2005/0090827 A1 | 4/2005 | Gedebou |
| 2005/0096699 A1 | 5/2005 | Wixey et al. |
| 2005/0110214 A1 | 5/2005 | Shank et al. |
| 2005/0113928 A1 | 5/2005 | Cragg et al. |
| 2005/0126680 A1 | 6/2005 | Aeschlimann et al. |
| 2005/0143826 A1 | 6/2005 | Zucherman et al. |
| 2005/0149024 A1 | 7/2005 | Ferrante et al. |
| 2005/0149029 A1 | 7/2005 | Bonutti |
| 2005/0203521 A1 | 9/2005 | Bonutti |
| 2005/0216059 A1 | 9/2005 | Bonutti |
| 2005/0216087 A1 | 9/2005 | Zucherman et al. |
| 2005/0222620 A1 | 10/2005 | Bonutti |
| 2005/0240190 A1 | 10/2005 | Gall et al. |
| 2005/0240227 A1 | 10/2005 | Bonutti |
| 2005/0246021 A1 | 11/2005 | Ringeisen et al. |
| 2005/0261684 A1 | 11/2005 | Shaolian et al. |
| 2005/0267481 A1 | 12/2005 | Carl et al. |
| 2005/0267534 A1 | 12/2005 | Bonutti |
| 2006/0009855 A1 | 1/2006 | Goble et al. |
| 2006/0015101 A1 | 1/2006 | Warburton et al. |
| 2006/0015108 A1 | 1/2006 | Bonutti |
| 2006/0024357 A1 | 2/2006 | Carpenter et al. |
| 2006/0026244 A1 | 2/2006 | Watson |
| 2006/0064095 A1 | 3/2006 | Senn et al. |
| 2006/0089646 A1 | 4/2006 | Bonutti |
| 2006/0122600 A1 | 6/2006 | Cole |
| 2006/0122704 A1 | 6/2006 | Vresilovic et al. |
| 2006/0142799 A1 | 6/2006 | Bonutti |
| 2006/0167495 A1 | 7/2006 | Bonutti |
| 2006/0200199 A1 | 9/2006 | Bonutti |
| 2006/0212073 A1 | 9/2006 | Bonutti |
| 2006/0217765 A1 | 9/2006 | Bonutti |
| 2006/0229623 A1 | 10/2006 | Bonutti |
| 2006/0235470 A1 | 10/2006 | Bonutti |
| 2006/0241695 A1 | 10/2006 | Bonutti |
| 2006/0265009 A1 | 11/2006 | Bonutti |
| 2006/0265011 A1 | 11/2006 | Bonutti |
| 2007/0032825 A1 | 2/2007 | Bonutti et al. |
| 2007/0088362 A1 | 4/2007 | Bonutti et al. |
| 2007/0102005 A1 | 5/2007 | Bonutti |
| 2007/0118129 A1 | 5/2007 | Fraser et al. |
| 2007/0198555 A1 | 8/2007 | Friedman et al. |
| 2007/0208378 A1 | 9/2007 | Bonutti et al. |
| 2007/0265561 A1 | 11/2007 | Yeung |
| 2007/0270833 A1 | 11/2007 | Bonutti |
| 2008/0021474 A1 | 1/2008 | Bonutti et al. |
| 2008/0039845 A1 | 2/2008 | Bonutti |
| 2008/0039873 A1 | 2/2008 | Bonutti |
| 2008/0046090 A1 | 2/2008 | Paul et al. |
| 2008/0047567 A1 | 2/2008 | Bonutti |
| 2008/0051799 A1 | 2/2008 | Bonutti |
| 2008/0058822 A1 | 3/2008 | Bonutti |
| 2008/0065140 A1 | 3/2008 | Bonutti |
| 2008/0097448 A1 | 4/2008 | Binder et al. |
| 2008/0103519 A1 | 5/2008 | Bonutti |
| 2008/0108897 A1 | 5/2008 | Bonutti et al. |
| 2008/0108916 A1 | 5/2008 | Bonutti |
| 2008/0114399 A1 | 5/2008 | Bonutti |
| 2008/0132950 A1 | 6/2008 | Lange |
| 2008/0140116 A1 | 6/2008 | Bonutti |
| 2008/0140117 A1 | 6/2008 | Bonutti |
| 2008/0195145 A1 | 8/2008 | Bonutti |
| 2008/0269753 A1 | 10/2008 | Cannestra |
| 2008/0269808 A1 | 10/2008 | Gall et al. |
| 2009/0024161 A1 | 1/2009 | Bonutti |
| 2009/0093684 A1 | 4/2009 | Schorer |
| 2009/0138014 A1 | 5/2009 | Bonutti |
| 2009/0194969 A1 | 8/2009 | Bearey |
| 2010/0211120 A1 | 8/2010 | Bonutti |
| 2010/0312350 A1 | 12/2010 | Bonutti |
| 2011/0060375 A1 | 3/2011 | Bonutti |
| 2011/0295253 A1 | 12/2011 | Bonutti et al. |
| 2012/0010623 A1 | 1/2012 | Bonutti |
| 2012/0165841 A1 | 6/2012 | Bonutti |
| 2012/0191140 A1 | 7/2012 | Bonutti |
| 2012/0215226 A1 | 8/2012 | Bonutti |
| 2012/0215233 A1 | 8/2012 | Bonutti et al. |
| 2012/0221017 A1 | 8/2012 | Bonutti |
| 2013/0144389 A1 | 6/2013 | Bonutti |
| 2013/0226185 A1 | 8/2013 | Bonutti |
| 2013/0226311 A1 | 8/2013 | Bonutti |
| 2014/0018852 A1 | 1/2014 | Bonutti |
| 2014/0018853 A1 | 1/2014 | Bonutti |
| 2014/0018854 A1 | 1/2014 | Bonutti |
| 2014/0025110 A1 | 1/2014 | Bonutti |
| 2014/0025111 A1 | 1/2014 | Bonutti |
| 2014/0025112 A1 | 1/2014 | Bonutti |

FOREIGN PATENT DOCUMENTS

| | | |
|---|---|---|
| CA | 2680827 | 9/2008 |
| CA | 2698057 | 3/2009 |
| CH | 117960 A | 5/1927 |
| DE | 337437 C | 5/1921 |
| DE | 605255 C | 11/1934 |
| DE | 1903016 | 10/1964 |
| DE | 1903316 | 10/1964 |
| DE | 1903016 | 8/1970 |
| DE | 2411226 A1 | 9/1974 |
| DE | 32 11 682 | 10/1983 |
| DE | 3517204 | 11/1986 |
| DE | 37 07 787 A1 | 9/1988 |
| DE | 3722538 | 1/1989 |
| DE | 90 02 844.9 U1 | 1/1991 |
| DE | 9002844 U1 | 1/1991 |
| EP | 0 010 650 A1 | 5/1980 |
| EP | 0 192 576 A1 | 8/1986 |
| EP | 0 283 661 A2 | 9/1988 |
| EP | 0 287 998 A2 | 10/1988 |
| EP | 0 418 147 A1 | 3/1991 |
| EP | 0 699 416 | 3/1996 |
| EP | 784454 | 5/1996 |
| EP | 773004 | 5/1997 |
| EP | 1614525 | 1/2006 |
| EP | 1988837 | 8/2007 |
| EP | 2134294 | 12/2009 |
| FR | 325846 A | 5/1903 |
| FR | 726041 A | 5/1932 |
| FR | 1 111 677 A | 3/1956 |
| FR | 2 344 267 A1 | 10/1977 |
| FR | 2 580 504 A1 | 10/1986 |
| FR | 2 682 287 A1 | 4/1993 |
| FR | 2717368 | 3/1994 |
| FR | 2 696 338 | 4/1994 |
| FR | 2696338 | 4/1994 |
| FR | 2728779 | 1/1995 |
| FR | 2736257 | 7/1995 |
| FR | 2750031 | 6/1996 |

(56) References Cited

FOREIGN PATENT DOCUMENTS

| FR | 2771621 | | 11/1997 |
|----|---------|---|---------|
| FR | 2785171 | | 10/1998 |
| GB | 214913 | A | 5/1924 |
| GB | 2093701 | A | 9/1982 |
| GB | 2306110 | A | 4/1997 |
| JP | S6429266 | A | 1/1989 |
| JP | 8140982 | | 6/1996 |
| JP | H08173436 | | 7/1996 |
| JP | 3738221 | | 1/2006 |
| SU | 184396 | | 7/1966 |
| SU | 1323090 | A1 | 7/1987 |
| SU | 1367947 | A1 | 1/1988 |
| WO | WO 87/01270 | A1 | 3/1987 |
| WO | WO 88/01517 | A1 | 3/1988 |
| WO | 91/12779 | | 9/1991 |
| WO | 93/23094 | | 11/1993 |
| WO | WO 93/23094 | | 11/1993 |
| WO | WO9408642 | | 4/1994 |
| WO | 95/16398 | | 6/1995 |
| WO | WO 95/16398 | | 6/1995 |
| WO | WO 95/31941 | | 11/1995 |
| WO | WO9614802 | | 5/1996 |
| WO | WO 96/29029 | | 9/1996 |
| WO | WO9712779 | | 4/1997 |
| WO | WO 97/20522 | | 6/1997 |
| WO | WO 97/39700 | | 10/1997 |
| WO | 97/49347 | | 12/1997 |
| WO | WO 97/49347 | | 12/1997 |
| WO | WO9811838 | | 3/1998 |
| WO | WO9826720 | | 6/1998 |
| WO | WO0253011 | | 7/2002 |
| WO | 2007/092869 | | 8/2007 |
| WO | 2007/092869 | A2 | 8/2007 |
| WO | WO 2007/092869 | A3 | 8/2007 |
| WO | 2008/116203 | | 9/2008 |
| WO | 2009/029908 | | 3/2009 |
| WO | WO2010099222 | | 2/2010 |

OTHER PUBLICATIONS

Copending U.S. Appl. No. 11/258,795 Non-Final Office Action mailed Apr. 26, 2011.
Copending U.S. Appl. No. 11/689,670, RCE Response Sep. 19, 2011.
European Search Report dated Sep. 10, 2012 for EP08732724.3.
Copending U.S. Appl. No. 10/614,352, Final Office Action Jul. 12, 2010.
Copending U.S. Appl. No. 11/932,602 Final Response to Office Action Jun. 10, 2011.
Copending U.S. Appl. No. 11/671,556 Response filed Aug. 23, 2010.
Co-pending U.S. Appl. No. 11/438,537, Supplemental Final Rejection mailed Sep. 25, 2009.
Petition for Inter Partes Review of U.S. Patent No. 5,980,559, IPR 2013-00603, Filing Date Sep. 24, 2013.
Petition for Inter Partes Review of U.S. Patent No. 7,087,073, IPR 2013-00604, Filing Date Sep. 24, 2013.
Declaration of Wayne J. Sebastianelli, MD Regarding U.S. Patent No. 7,087,073, Sep. 24, 2013, IPR 2013-00604.
Petition for Inter Partes Review of U.S. Patent No. 6,500,195, IPR 2013-00624, Filing Date Oct. 2, 2013.
Declaration of Dr. Philip Hardy in Support of Petition for Inter Partes Review of U.S. Patent No. 6,500,195, IPR 2013-00624,.
Petition for Inter Partes Review of U.S. Patent No. 5,527,343, IPR 2013-00628, Filing Date Sep. 26, 2013, Sep. 25, 2013.
Corrected Petition for Inter Partes Review of US Patent No. 5,921,986, IPR 2013-00631, Filing Date Sep. 27, 2013.
Expert Declaration of Steve E. Jordan, MD, for Inter Partes Review of US Patent No. 5,921,986, IPR 2013-00631, Sep. 24, 2013.
Corrected Petition for Inter Partes Review of US Patent No. 8,147,514, IPR 2013-00632, Filing Date Sep. 27, 2013.
Declaration of Steve Jordan for USP 8,147,514, from IPR 2013-00632, dated Sep. 23, 2013 (exhibit 1009).
Corrected Petition for Inter Partes Review of US Patnet No. 8,147,514, IPR 2013-00633, Filing Date Sep. 27, 2013.
Declaration of Steve Jordan for USP 8,147,514, from IPR 2013-00633, dated Sep. 23, 2013 (exhibit 1006).
Flory, Principles of Polymer Chemistry, 1953, selected pages (cited in IPR 2013-00603, exhibit 1012).
Grizzi, Hydrolytic degradation of devices based on poly(DL-lactic acid) size-dependence, Biomaterials, 1995, vol. 16, No. 4, p. 305-11 (cited in IPR 2013-00603, exhibit 1006).
Gopferich, Mechanisms of polymer degradation and erosion, Biomaterials, 1996, vol. 17, No. 2, p. 103-114 (cited in IPR 2013-00603, exhibit 1013).
Gao et el, Swelling of Hydroxypropyl Methylcellulose Matrix Tablets . . . , J. of Pharmaceutical Sciences, vol. 85, No. 7, Jul. 1996, p. 732-740 (cited in IPR 2013-00603, exhibit 1014).
Linvatec, Impact Suture Anchor brochure, 2004 (cited in IPR 2013-00628, exhibit 1010).
Seitz et al, Repair of the Tibiofibular Syndesmosis with a Flexible Implant, J. of Orthopaedic Trauma, vol. 5, No. 1, p. 78-82, 1991 (cited in IPR 2013-00631, exhibit 1007) (cited in 2013-00632).
Translation of FR2696338 with translators certificate dated Sep. 17, 2013 (cited in IPR 2013-00631, 2013-00632).
Translation of DE9002844.9 with translator's certificate dated Sep. 26, 2013 (cited in IPR 2013-00631, 2013-00632).
Declaration of Steve Jordan for USP 5921986, from IPR 2013-00632, dated Sep. 24, 2013 (exhibit 1010).
Declaration of Steve Jordan for USP 5921986, from IPR 2013-00633, dated Sep. 24, 2013 (exhibit 1007).
Declaration of Dr. Steve E. Jordan for USP 8,147,514, from IPR 2013-00631, dated Sep. 23, 2013.
IPR—International Publication WO/2008/116203, published Sep. 22, 2009 for PCT/US08/57948.
ISR—International Search Report WO/2008/116203, published Dec. 24, 2008 for PCT/US08/57948.
IPER—Internation Preliminary Report on Patentability, WO/2008/116203, published Sep. 22, 2009 for PCT/US08/57948.
Written Opinion WO/2008/116203 dated Oct. 23, 2008 for PCT/US08/57948.
IPR—International Publication WO2009/029908, published May 3, 2009 for PCT/US08/74941.
ISR—International Search Report, WO2009/029908, published May 3, 2009 for PCT/US08/74941.
IPER—Internation Preliminary Report on Patentability, WO2009/029908, published Mar. 2, 2010 for PCT/US08/74941.
Written Opinion WO2009/029908 dated Feb. 28, 2010 for PCT/US08/74941.
International Search Report PCT/US2010/025263 completed Apr. 13, 2010.
Written Opinion for PCT/US2010/025263 completed Apr. 13, 2010.
Arthrex, Protect your graft, Am J Sports Med, vol. 22, No. 4, Jul.-Aug. 1994.
Barrett et al, T-Fix endoscopic meniscal repair: technique and approach to different types of tears, Apr-95, Arthroscopy vol. 11 No. 2 p. 245-51.
Cope, Suture Anchor for Visceral Drainage, AJR, vol. 148 p. 160-162, Jan. 1986.
Gabriel, Arthroscopic Fixation Devices, Wiley Enc. of Biomed Eng., 2006.
Innovasive, We've got you covered, Am J Sports Med, vol. 26, No. 1, Jan.-Feb. 1998.
510k—TranSet Fracture Fixation System, Feb. 24, 2004, k033717.
510k—Linvatec Biomaterials modification of Duet and impact Suture Anchor, Nov. 19, 2004, k042966.
510k, arthrex pushlock, Jun. 29, 2005, K051219.
510k, mitek micro anchor, Nov. 6, 1996, K962511.
510k, Multitak Suture System, Jan. 10, 1997, K964324.
510k, Modified Mitek 3.5mm Absorbable Suture Anchor System, Jun. 9, 1997, K970896.
510K, Summary for Arthrex Inc.'s Bio-Interference Screw, Jul. 9, 1997, K971358.
510k, Surgicraft Bone Tie, Sep. 25, 1998, K982719.

(56) References Cited

OTHER PUBLICATIONS

Karlsson et al, Repair of Bankart lesions with a suture anchor in recurrent dislocation of the shoulder, Scand. j. of Med & Science in Sports, 1995, 5:170-174.
Madjar et al, Minimally Invasive Pervaginam Procedures, for the Treatment of Female Stress Incontinence . . . , Artificial Organs, 22 (10) 879-885, 1998.
Nowak et al, Comparative Study of Fixation Techniques in the Open Bankart Operation Using Either a Cannulated Screw or Suture-Anchors, Acta Orthopcedica Belgica, vol. 64-2-1998.
Packer et al, Repair of Acute Scapho-Lunate Dissociation Facilitated by the "Tag" Suture Anchor, Journal of Hand Surgery (British and European Volume, 1994) 19B: 5: 563-564.
Shea et al, Technical Note: Arthroscopic Rotator Cuff Repair Using a Transhumeral Approach to Fixation, Arthroscopy: The Journal of Arthroscopic and Related Surgery, vol. 14, No. 1 (Jan.-Feb. 1998), pp. 118-122.
Tfix, Acufex just tied the knot . . . , Am. J. Sports Med., vol. 22, No. 3, May-Jun. 1994.
Wong et al, Case Report: Proper Insertion Angle Is Essential to Prevent Intra-Articular Protrusion of a Knotless Suture Anchor in Shoulder Rotator Cuff Repair, Arthroscopy: The Journal of Arthroscopic and Related Surgery, vol. 26, No. 2 (Feb. 2010), pp. 286-290.
Cobb et al, Late Correction of Malunited Intercondylar Humeral Fractures Intra-Articular Osteotomy and Tricortical Bone Grafting, J BoneJointSurg [Br] 1994; 76-B:622-6.
Fellinger, et al, Radial avulsion of the triangular fibrocartilage complex in acute wrist trauma: a new technique for arthroscopic repair, Jun. 1997, Arthroscopy vol. 13 No. 3 p. 370-4.
Hecker et al , Pull-out strength of suture anchors for rotator cuff and Bankart lesion repairs, Nov.-Dec. 1993 , The American Journal of Sports Medicine, vol. 21 No. 6 p. 874-9.
Hernigou et al , Proximal Tibial Osteotomy for Osteoarthritis with Varus Deformity A Ten to Thirteen-Year Follow-Up Study, J Bone Joint Surg, vol. 69-A, No. 3. Mar. 1987, p. 332-354.
Ibarra et al, Glenoid Replacement in Total Shoulder Arthroplasty, The Orthopedic Clinics of Northamerica: Total Shoulder Arthroplasty, vol. 29 No. 3, Jul. 1998 p. 403-413.
Mosca et al, Calcaneal Lengthening for Valgus Deformity of the Hindfoot: Results in Children Who Had Severe, Symptomatic fLATFOOT and Skewfoot, J Bone Joint Surg,, 1195- p. 499-512.
Murphycet al , Radial Opening Wedge Osteotomy in Madelung's Deformity, J. Hand Surg, vol. 21 A No. 6 Nov. 1996, p. 1035-44.
Biomet, Stanmore Modular Hip, J. Bone Joint Surg., vol. 76-B : No. Two, Mar. 1994.
Intl Prelim Rep on Patentability and Written Opinion for PCT/US10/25263 dated Aug. 30, 2011.
The Search for the Holy Grail: A Centrury of Anterior Cruciate Ligament Reconstruction, R. John Naranja, American Journal of Orthopedics, Nov. 1997.
Femoral Bone Plug Recession in Endoscope Anterior Cruciate Ligament Reconstruction, David E. Taylor, Arthroscopy: The Journal of Arthroscopic and Related Surgery, Aug. 1996.
Meniscus Replacement with Bone Anchors: A Surgical Technique, Arthroscopy: The Journal of Arthroscopic and Related Surgery, 1994.
Problem Solving Report Question No. 1014984.066, Ultrasonic Welding, (c) 1999.
Guide to Ultrasound Plastic Assembly, Ultrasonic Division Publication, (c) 1995.
Branson, Polymers: Characteristics and Compatibility for Ultrasonic Assembly, Applied Technologies Group, Publication unknown.
Enabling Local Drug Delivery-Implant Device Combination Therapies, Surmodics, Inc., (c) 2003.
Stent Based Delivery of Sirolimus Reduces Neointimal Formation in a Porcine Coronary Model, Takeshi Suzuki, American Heart Association, Inc. (c) 2001.
Why Tie a Knot When You Can Use Y-Knot?, Innovasive Devices Inc., (c) 1998.
Ask Oxford, compact Oxford English dictionary: projection, Mar. 30, 2009.
Ask Oxford, compact Oxford English dictionary: slit, Mar. 30, 2009.
Textured Surface Technology, Branson Technolog, Branson Ultrasonics Copr., (c) 1992.
IPR—International Publication WO/2007/092869, published Aug. 16, 2007 for PCT/US2007/061730.
ISR—International Search Report WO/2007/092869, published Dec. 13, 2007 for PCT/US2007/061730.
Intl Prelim Report on Patentability, WO/2007/092869, published Aug. 12, 2008 for PCT/US2007/061730.
Written Opinion WO/2007/092869 dated Aug. 7, 2008 for PCT/US2007/061730.
U.S. Appl. No. 13/221,043, filed Jun. 2001, Bonutti.
Copending U.S. Appl. No. 09/556,458, Non-Final Rejection mailed Sep. 25, 2002.
Copending U.S. Appl. No. 09/556,458, Response to Office Action Dec. 26, 2002.
Copending U.S. Appl. No. 10/614,352, Examiner Interview Summary Jul. 31, 2007.
Copending U.S. Appl. No. 10/614,352, Final Rejection mailed Jan. 25, 2007.
Copending U.S. Appl. No. 10/614,352, Final Rejection mailed Apr. 14, 2009.
Copending U.S. Appl. No. 10/614,352, Final Rejection mailed Oct. 2, 2007.
Copending U.S. Appl. No. 10/614,352, non Final Office Action Aug. 10, 2011.
Copending U.S. Appl. No. 10/614,352, Non-Final Rejection mailed Jan. 15, 2008.
Copending U.S. Appl. No. 10/614,352, Non-Final Rejection mailed Apr. 17, 2007.
Copending U.S. Appl. No. 10/614,352, Non-Final Rejection mailed Aug. 1, 2006.
Copending U.S. Appl. No. 10/614,352, Non-Final Rejection mailed Aug. 21, 2008.
Copending U.S. Appl. No. 10/614,352, Non-Final Rejection mailed Nov. 24, 2009.
Copending U.S. Appl. No. 10/614,352, Non-Final Rejection mailed Dec. 1, 2005.
Copending U.S. Appl. No. 10/614,352, Request for Continued Examination Sep. 14, 2009.
Copending U.S. Appl. No. 10/614,352, Request for Continued Examination Oct. 30, 2007.
Copending U.S. Appl. No. 10/614,352, Response to Office Action Mar. 1, 2006.
Copending U.S. Appl. No. 10/614,352, Response to Office Action Mar. 26, 2007.
Copending U.S. Appl. No. 10/614,352, Response to Office Action Apr. 26, 2010.
Copending U.S. Appl. No. 10/614,352, Response to Office Action May 15, 2008.
Copending U.S. Appl. No. 10/614,352, Response to Office Action Jul. 17, 2007.
Copending U.S. Appl. No. 10/614,352, Response to Office Action Sep. 14, 2009.
Copending U.S. Appl. No. 10/614,352, Response to Office Action Oct. 30, 2007.
Copending U.S. Appl. No. 10/614,352, Response to Office Action Nov. 1, 2006.
Copending U.S. Appl. No. 10/614,352, Response to Office Action Dec. 22, 2008.
Copending U.S. Appl. No. 11/931,823, final Office Action mailed Aug. 2, 2011.
Copending U.S. Appl. No. 11/931,823, Office Action mailed Nov. 24, 2010.
Copending U.S. Appl. No. 11/931,823, Response to Office Action Aug. 9, 2010.
Copending U.S. Appl. No. 11/931,823, RestrictionElect dated Jun. 8, 2010.
Copending U.S. Appl. No. 11/187,482, Response to Office Action Jun. 21. 2011.

(56) References Cited

OTHER PUBLICATIONS

Copending U.S. Appl. No. 10/413,696, Non-Final Rejection mailed Sep. 23, 2005.
Copending U.S. Appl. No. 10/413,696, Requirement for Restriction Jun. 8, 2005.
Copending U.S. Appl. No. 10/413,696, Response to Office Action Jul. 5, 2005.
Copending U.S. Appl. No. 10/413,696, Response to Office Action Dec. 20, 2005.
Copending U.S. Appl. No. 11/460,650, Examiner Interview Summary mailed Dec. 23, 2009.
Copending U.S. Appl. No. 11/460,650, Final Rejection mailed Apr. 20, 2010.
Copending U.S. Appl. No. 11/460,650, Final Rejection mailed Aug. 29, 2008.
Copending U.S. Appl. No. 11/460,650, Non-Final Rejection mailed Mar. 10, 2009.
Copending U.S. Appl. No. 11/460,650, Non-Final Rejection mailed May 30, 2007.
Copending U.S. Appl. No. 11/460,650, Non-Final Rejection mailed Sep. 16, 2009.
Copending U.S. Appl. No. 11/460,650, Non-Final Rejection mailed Dec. 28, 2007.
Copending U.S. Appl. No. 11/460,650, Request for Continued Examination Jan. 29, 2009.
Copending U.S. Appl. No. 11/460,650, Response to Office Action Jan. 12, 2010.
Copending U.S. Appl. No. 11/460,650, Response to Office Action Jan. 29, 2009.
Copending U.S. Appl. No. 11/460,650, Response to Office Action Mar. 28, 2008.
Copending U.S. Appl. No. 11/460,650, Response to Office Action Jun. 10, 2009.
Copending U.S. Appl. No. 11/460,650, Response to Office Action Oct. 1, 2007.
Copending U.S. Appl. No. 11/461,110, Final Rejection mailed Dec. 8, 2009.
Copending U.S. Appl. No. 11/461,110, Non-Final Rejection mailed Apr. 22, 2009.
Copending U.S. Appl. No. 11/461,110, Non-Final Rejection mailed Jun. 6, 2008.
Copending U.S. Appl. No. 11/461,110, Request for Continued Examination Mar. 12, 2008.
Copending U.S. Appl. No. 11/461,110, Request for Continued Examination Jun. 8, 2010.
Copending U.S. Appl. No. 11/461,110, Response to Office Action Mar. 12, 2008.
Copending U.S. Appl. No. 11/461,110, Response to Office Action Jun. 8, 2010.
Copending U.S. Appl. No. 11/461,110, Response to Office Action Sep. 22, 2009.
Copending U.S. Appl. No. 11/461,110, Response to Office Action Oct. 6, 2008.
Copending U.S. Appl. No. 11/461,110, Response to Office Action Oct. 15, 2007.
Copending U.S. Appl. No. 11/461,110, Final Rejection mailed Dec. 12, 2007.
Copending U.S. Appl. No. 11/461,110, Non-Final Rejection mailed May 14, 2007.
Copending U.S. Appl. No. 11/930,621, Final Rejection Jun. 22, 2010.
Copending U.S. Appl. No. 11/930,621, Non-Final Rejection mailed Sep. 21, 2009.
Copending U.S. Appl. No. 11/930,621, Response to Office Action Mar. 22, 2010.
Copending U.S. Appl. No. 09/524,397, Final Rejection mailed Jun. 15, 2001.
Copending U.S. Appl. No. 09/524,397, Non-Final Rejection mailed Dec. 18, 2000.
Copending U.S. Appl. No. 09/524,397, Response to Office Action Mar. 19, 2001.
Copending U.S. Appl. No. 09/524,397, Response to Office Action Oct. 15, 2001.
Copending U.S. Appl. No. 10/458,117, Advisory Action Jan. 20, 2006.
Copending U.S. Appl. No. 10/458,117, Examiner Interview Summary mailed May 16, 2008.
Copending U.S. Appl. No. 10/458,117, Non-Final Rejection mailed Mar. 22, 2005.
Copending U.S. Appl. No. 10/458,117, Non-Final Rejection mailed Nov. 15, 2006.
Copending U.S. Appl. No. 10/458,117, Request for Continued Examination Feb. 26, 2008.
Copending U.S. Appl. No. 10/458,117, Request for Continued Examination Feb. 21, 2006.
Copending U.S. Appl. No. 10/458,117, Request for Continued Examination Aug. 3, 2007.
Copending U.S. Appl. No. 10/458,117, Response to Office Action Feb. 13, 2007.
Copending U.S. Appl. No. 10/458,117, Response to Office Action Jun. 22, 2005.
Copending U.S. Appl. No. 10/458,117, Response to Office Action Aug. 3, 2007.
Copending U.S. Appl. No. 10/458,117, Response to Office Action Nov. 8, 2005.
Copending U.S. Appl. No. 10/458,117, Final Rejection mailed May 3, 2007.
Copending U.S. Appl. No. 10/458,117, Final Rejection mailed Sep. 8, 2005.
Copending U.S. Appl. No. 11/370,775, Examiner Interview Summary mailed Oct. 29, 2007.
Copending U.S. Appl. No. 11/370,775, Examiner Interview Summary mailed Apr. 24, 2008.
Copending U.S. Appl. No. 11/370,775, Examiner Interview Summary mailed Feb. 27, 2009.
Copending U.S. Appl. No. 11/370,775, Examiner Interview Summary mailed Aug. 28, 2009.
Copending U.S. Appl. No. 11/370,775, Non-Final Rejection mailed Feb. 6, 2007.
Copending U.S. Appl. No. 11/370,775, Non-Final Rejection mailed Jan. 22, 2008.
Copending U.S. Appl. No. 11/370,775, Non-Final Rejection mailed Oct. 15, 2008.
Copending U.S. Appl. No. 11/370,775, Non-Final Rejection mailed Nov. 6, 2009.
Copending U.S. Appl. No. 11/370,775, Response to Office Action Jun. 4, 2007.
Copending U.S. Appl. No. 11/370,775, Response to Office Action Oct. 26, 2007.
Copending U.S. Appl. No. 11/370,775, Response to Office Action May 22, 2008.
Copending U.S. Appl. No. 11/370,775, Response to Office Action Jan. 15, 2009.
Copending U.S. Appl. No. 11/370,775, Response to Office Action Aug. 13, 2009.
Copending U.S. Appl. No. 11/370,775, Response to Office Action May 6, 2010.
Copending U.S. Appl. No. 11/370,775, Supplemental Response to Office Action Jan. 30, 2009.
Copending U.S. Appl. No. 11/370,775, Final Rejection mailed Aug. 31, 2007.
Copending U.S. Appl. No. 11/370,775, Final Rejection mailed Mar. 13, 2009.
Copending U.S. Appl. No. 11/370,775, Request for Continued Examination Oct. 26, 2007.
Copending U.S. Appl. No. 11/370,775, Request for Continued Examination Jan. 10, 2011.
Copending U.S. Appl. No. 11/370,775, Request for Continued Examination Aug. 13, 2009.
Copending U.S. Appl. No. 11/456,132, Examiner Interview Summary mailed Aug. 28, 2009.
Copending U.S. Appl. No. 11/456,132, Request for Continued Examination Jun. 11, 2008.

(56) References Cited

OTHER PUBLICATIONS

Copending U.S. Appl. No. 11/456,132, Response to Office Action Jan. 7, 2009.
Copending U.S. Appl. No. 11/456,132, Response filed Jan. 18, 2012.
Copending U.S. Appl. No. 11/456,132, Response to Office Action Apr. 14, 2011.
Copending U.S. Appl. No. 11/456,132, Response to Office Action Apr. 19, 2010.
Copending U.S. Appl. No. 11/456,132, Response to Office Action Jun. 11, 2008.
Copending U.S. Appl. No. 11/456,132, Response to Office Action Aug. 13, 2009.
Copending U.S. Appl. No. 11/456,132, Response to Office Action Nov. 19, 2007.
Copending U.S. Appl. No. 11/456,132, Final Rejection mailed Mar. 11, 2008.
Copending U.S. Appl. No. 11/456,132, Final Rejection mailed Dec. 18, 2009.
Copending U.S. Appl. No. 11/456,132, Non-Final Rejection mailed Mar. 13, 2009.
Copending U.S. Appl. No. 11/456,132, Non-Final Rejection mailed Jun. 18, 2007.
Copending U.S. Appl. No. 11/456,132, Non-Final Rejection mailed Oct. 7, 2008.
Copending U.S. Appl. No. 11/456,221, Final Rejection mailed Feb. 22, 2008.
Copending U.S. Appl. No. 11/456,221, Final Rejection mailed Mar. 24, 2010.
Copending U.S. Appl. No. 11/456,221, Non-Final Rejection mailed Jul. 6, 2009.
Copending U.S. Appl. No. 11/456,221, Non-Final Rejection mailed Jul. 9, 2007.
Copending U.S. Appl. No. 11/456,221, Non-Final Rejection mailed Oct. 29, 2008.
Copending U.S. Appl. No. 11/456,221, Request for Continued Examintation Jun. 19, 2008.
Copending U.S. Appl. No. 11/456,221, Response to Office Action Jan. 6, 2010.
Copending U.S. Appl. No. 11/456,221, Response to Office Action Mar. 30, 2009.
Copending U.S. Appl. No. 11/456,221, Response to Office Action May 22, 2008.
Copending U.S. Appl. No. 11/456,221, Response to Office Action Nov. 9, 2007.
Copending U.S. Appl. No. 11/932,051, Final Office Action mailed Jun. 9, 2011.
Copending U.S. Appl. No. 11/932,051, RCE Response Dec. 9, 2011.
Copending U.S. Appl. No. 11/932,051, Requirement for Restriction Jan. 22, 2010.
Copending U.S. Appl. No. 10/228,855, Non-Final Rejection mailed Sep. 28, 2005.
Copending U.S. Appl. No. 10/228,855, Response to Office Action Dec. 28, 2005.
Copending U.S. Appl. No. 11/465,199, Response to Office Action Jun. 28, 2010.
Copending U.S. Appl. No. 11/465,199, Non-Final Rejection mailed Dec. 28, 2009.
Copending U.S. Appl. No. 11/932,602, non final Office Action Oct. 6, 2010.
Copending U.S. Appl. No. 11/932,602, Response to Office Action Apr. 6, 2011.
Copending U.S. Appl. No. 12/359,364, Final Office Action Apr. 7, 2011.
Copending U.S. Appl. No. 11/438,537, RCE Response Nov. 21, 2011.
Copending U.S. Appl. No. 11/932,907, non-final Office Action Nov. 17, 2010.
Copending U.S. Appl. No. 11/932,907, Response to Office Action Apr. 18, 2011.
Copending U.S. Appl. No. 11/133,730, Final Office action Aug. 17, 2011.
Copending U.S. Appl. No. 11/169,475, Response Sep. 2, 2011.
Copending U.S. Appl. No. 11/169,475, Office Action Mar. 2, 2011.
Copending U.S. Appl. No. 11/126,543, non Final Office Action Aug. 10, 2011.
Copending U.S. Appl. No. 11/126,543, RCE Response filed Jun. 30, 2011.
Copending U.S. Appl. No. 10/780,444, Examiner Interview Summary mailed Nov. 20, 2009.
Copending U.S. Appl. No. 10/780,444, Final Rejection mailed Mar. 30, 2010.
Copending U.S. Appl. No. 10/780,444, Final Rejection mailed Dec. 23, 2008.
Copending U.S. Appl. No. 10/780,444, nonFinal Office Action Aug. 9, 2011.
Copending U.S. Appl. No. 10/780,444, Non-Final Rejection mailed Mar. 11, 2008.
Copending U.S. Appl. No. 10/780,444, Non-Final Rejection mailed Jul. 7, 2009.
Copending U.S. Appl. No. 10/780,444, Request for Continued Examination Apr. 23, 2009.
Copending U.S. Appl. No. 10/780,444, Requirement for Restriction Sep. 12, 2007.
Copending U.S. Appl. No. 10/780,444, Requirement for Restriction Apr. 10, 2007.
Copending U.S. Appl. No. 10/780,444, Response filed Feb. 9, 2012.
Copending U.S. Appl. No. 10/780,444, Response to Office Action Apr. 23, 2009.
Copending U.S. Appl. No. 10/780,444, Response to Office Action May 10, 2007.
Copending U.S. Appl. No. 10/780,444, Response to Office Action Jul. 9, 2008.
Copending U.S. Appl. No. 10/780,444, Response to Office Action Oct. 12, 2007.
Copending U.S. Appl. No. 10/780,444, Response to Office Action Dec. 4, 2009.
Copending U.S. Appl. No. 10/779,978, Non-Final Office Action mailed Jan. 13, 2011.
Copending U.S. Appl. No. 10/779,978, Final Rejection mailed Feb. 3, 2009.
Copending U.S. Appl. No. 10/779,978, Final Rejection mailed May 14, 2010.
Copending U.S. Appl. No. 10/779,978, Non-Final Rejection mailed Jun. 18, 2008.
Copending U.S. Appl. No. 10/779,978, Non-Final Rejection mailed Aug. 3, 2007.
Copending U.S. Appl. No. 10/779,978, Non-Final Rejection mailed Oct. 1, 2009.
Copending U.S. Appl. No. 10/779,978, Request for Continued Examination Jul. 6, 2009.
Copending U.S. Appl. No. 10/779,978, Requirement for Restriction Apr. 20, 2007.
Copending U.S. Appl. No. 10/779,978, Response to Office Action Feb. 1, 2010.
Copending U.S. Appl. No. 10/779,978, Response to Office Action Mar. 25, 2008.
Copending U.S. Appl. No. 10/779,978, Response to Office Action May 21, 2007.
Copending U.S. Appl. No. 10/779,978, Response to Office Action Jul. 6, 2009.
Copending U.S. Appl. No. 10/779,978, Response to Office Action Jul. 13, 2011.
Copending U.S. Appl. No. 10/779,978, Response to Office Action Oct. 20, 2008.
Copending U.S. Appl. No. 10/779,978, Response to Office Action Dec. 3, 2007.
Copending U.S. Appl. No. 10/797,685, Examiner Interview Summary mailed Sep. 11, 2007.
Copending U.S. Appl. No. 10/797,685, Final Rejection mailed Apr. 25, 2007.
Copending U.S. Appl. No. 10/797,685, Non-Final Rejection mailed Nov. 17, 2006.

(56) References Cited

OTHER PUBLICATIONS

Copending U.S. Appl. No. 10/797,685, Response to Office Action Feb. 20, 2007.
Copending U.S. Appl. No. 10/797,685, Response to Office Action Aug. 27, 2007.
Copending U.S. Appl. No. 11/874,323, Office Action mailed Jul. 6, 2011.
Copending U.S. Appl. No. 11/874,323, Response filed Jun. 21, 2011.
Copending U.S. Appl. No. 11/202,294, Office Action mailed Jun. 24, 2011.
Copending U.S. Appl. No. 11/202,294, Response filed Dec. 24, 2011.
Copending U.S. Appl. No. 11/358,399, non Final Office Action Jan. 3, 2011.
Copending U.S. Appl. No. 11/358,399, Response filed Jul. 5, 2011.
Copending U.S. Appl. No. 11/671,556, Final Office Action mailed Nov. 12, 2010.
Copending U.S. Appl. No. 11/671,556, Non-Final Rejection mailed Feb. 22, 2010.
Copending U.S. Appl. No. 11/671,556, Requirement for Restriction Sep. 1, 2009.
Copending U.S. Appl. No. 11/671,556, Response to Office Action Nov. 2, 2009.
Copending U.S. Appl. No. 11/416,618, Examiner Interview Summary mailed Apr. 15, 2010.
Copending U.S. Appl. No. 11/416,618, Final Rejection mailed Jun. 24, 2009.
Copending U.S. Appl. No. 11/416,618, Non-Final Rejection mailed Oct. 13, 2009.
Copending U.S. Appl. No. 11/416,618, Non-Final Rejection mailed Nov. 26, 2008.
Copending U.S. Appl. No. 11/416,618, Response to Office Action Mar. 15, 2010.
Copending U.S. Appl. No. 11/416,618, Response to Office Action Mar. 26, 2009.
Copending U.S. Appl. No. 11/416,618, Response to Office Action Apr. 16, 2010.
Copending U.S. Appl. No. 11/416,618, Response to Office Action Sep. 24, 2009.
Copending U.S. Appl. No. 11/416,618, Request for Continued Examination Dec. 8, 2010.
Copending U.S. Appl. No. 11/689,670, Final Office Action mailed Mar. 17, 2011.
Copending U.S. Appl. No. 11/689,670, Requirement for Restriction Mar. 15, 2010.
Copending U.S. Appl. No. 11/689,670, Response to Office Action Jan. 3, 2011.
Copending U.S. Appl. No. 11/689,670, Response to Office Action Apr. 15, 2010.
Copending U.S. Appl. No. 12/202,210, Requirement for Restriction mailed Aug. 16, 2011.
Copending U.S. Appl. No. 12/202,210, Response filed Dec. 16, 2011.
File History of U.S. Patent No. 5,403,348; U.S. Appl. No. 08/062,295; filed May 14, 1993; 231 pages.
File History of U.S. Patent No. 5,522,846; U.S. Appl. No. 08/402,352; filed Mar. 10, 1995; 215 pages.
File History of U.S. Patent No. 5,527,343; U.S. Appl. No. 08/344,466; filed Nov. 23, 1994; 246 pages.
File History of U.S. Patent No. 5,549,630; U.S. Appl. No. 08/291,970; filed Aug. 17, 1994; 276 pages.
File History of U.S. Patent No. 5,980,559; U.S. Appl. No. 08/964,167; filed Nov. 4, 1997; 57 pages.
File History of U.S. Patent No. 6,500,195; U.S. Appl. No. 09/872,033; filed Jun. 1, 2001; 522 pages.
File History of U.S. Patent No. 7,087,073; U.S. Appl. No. 10/413,696; filed Apr. 14, 2003; 13 pages.
Petition for *Inter Partes* Review of U.S. Patent No. 5,980,559 Under 35 U.S.C. § 312 and 37 C.F.R. § 42.104; filed Sep. 24, 2013; IPR2013-00603; with exhibits, 382 pages.
Declaration of David Kaplan, PH.D. Regarding U.S. Patent No. 5,980,559, IPR 2013-00603, Sep. 24, 2013.
Petition for *Inter Partes* Review of U.S. Patent No. 7,087,073 Under 35 U.S.C. § 312 and 37 C.F.R. § 42.104; filed Sep. 24, 2013; IPR2013-00604; with exhibits, 243 pages.
Declaration of Wayne J. Sebastianelli, MD Regarding U.S. Patent No. 7,087,073, Sep. 24, 2013,IPR 2013-00604.
Petition for *Inter Partes* Review of U.S. Patent No. 6,500,195 Under 35 U.S.C. § 312 and 37 C.F.R. § 42.104; filed Sep. 25, 2013; IPR2013-00624; with exhibits, 1152 pages.
Declaration of Dr. Philip Hardy in Support of Petition for Inter Partes Review of U.S. Patent No. 6,500,195, IPR 2013-00624.
Petition for *Inter Partes* Review of U.S. Patent No. 5,527,343 Under 35 U.S.C. § 312 and 37 C.F.R. § 42.104; filed Sep. 26, 2013; IPR2013-00628; with exhibits, 882 pages.
Declaration of Dr. Philip Hardy in Support of Petition for Inter Partes Review of U.S. Patent No. 5,527,343, IPR 2013-00628, Sep. 25, 2013.
Corrected Petition for *Inter Partes* Review of U.S. Patent No. 5,921,986 Under 35 U.S.C. §§ 311-319 and 37 C.F.R. § 42.100 Et Seq.; filed Oct. 11, 2013; IPR2013-00631; with exhibits, 285 pages.
Expert Declaration of Steve E. Jordan, MD, for Inter Partes Review of U.S. Patent No. 5,921,986, IPR 2013-00631, Sep. 24, 2013.
Corrected Petition for *Inter Partes* Review of U.S. Patent No. 8,147,514 Under 35 U.S.C. §§ 311-319 and 37 C.F.R. § 42.100 Et Seq.; filed Oct. 11, 2013; IPR2013-00632; with exhibits, 268 pages.
Declaration of Steve E. Jordan for U.S. Patent No. 8,147,514, IPR 2013-00631, dated Sep. 23, 2013.
Declaration of Steve E. Jordan for U.S. Patent No. 8,147,514, IPR 2013-00632 and IPR 2013-00633, Sep. 23, 2013; (exhibits 1006 & 1009); 61 pages.
Declaration of Steve E. Jordan for U.S. Patent No. 5,921,986, from IPR 2013-00632, dated Sep. 24, 2013 (exhibit 1010).
Declaration of Steve E. Jordan for U.S. Patent No. 5,921,986, from IPR 2013-00633, dated Sep. 24, 2013 (exhibit 1007).
Corrected Petition for *Inter Partes* Review of U.S. Patent No. 8,147,514 Under 35 U.S.C. §§ 311-319 and 37 C.F.R. § 42.100 Et. Seq.; filed Oct. 11, 2013; IPR2013-00633; with exhibits, 248 pages.
*Bonutti Skeletal Innovations LLC* v. *Linvatec Corporation and ConMed Corporation*; "Defendants Linvatec and ConMed Corporation's Invalidity Contentions;" With Exhibits; Case No. 6:12-cv-01379; M.D. Florida; Sep. 30, 2013; 2703 pages.
*Bonutti Skeletal Innovations LLC* v. *Linvatec Corporation and ConMed Corporation*; "Defendants Linvatec and ConMed Corporation's Non-Infringement Contentions;" With Exhibits; Case No. 6:12-cv-01379; M.D. Florida; Sep. 30, 2013; 310 pages.
*Bonutti Skeletal Innovations LLC* v. *Linvatec Corporation and ConMed Corporation*; "Defendants' Proposed Claim Term Constructions;" With Exhibits; Case No. 6:12-cv-01379; M.D. Florida; Nov. 1, 2013; 53 pages.
*Bonutti Skeletal Innovations LLC* v. *Linvatec Corporation and ConMed Corporation*; "Defendants' Proposed Terms for Construction;" Case No. 6:12-cv-01379; M.D. Florida; Oct. 10, 2013; 9 pages.
*Bonutti Skeletal Innovations LLC* v. *Linvatec Corporation and ConMed Corporation*; "Joint Claim Construction Statement;" With Exhibits; Case No. 6:12-cv-01379; M.D. Florida; Nov. 15, 2013; 55 pages.
*Bonutti Skeletal Innovations LLC* v. *Linvatec Corporation and ConMed Corporation*; "Plaintiff Bonutti Skeletal Innovations LLC's Initial Identification of Disputed Claim Terms;" Case No. 6:12-cv-01379; M.D. Florida; Oct. 10, 2013; 3 pages.
*Bonutti Skeletal Innovations LLC* v. *Linvatec Corporation and ConMed Corporation*; "Plaintiff Bonutti Skeletal Innovations LLC's Proposed Interpretations of Disputed Claim Terms;" With Exhibits; Case No. 6:12-cv-01379; M.D. Florida; Nov. 1, 2013; 35 pages.
*Bonutti Skeletal Innovations LLC* v. *Linvatec Corporation and ConMed Corporation*; "Order;" Case No. 6:12-cv-1379-Orl-22TBS; M.D. Florida; Mar. 25, 2014; 22 pages.
*Bonutti Skeletal Innovations LLC* v. *Arthrex*; "Defendant Arthrex Inc.'s Preliminary Identification of Proposed Claim Terms for Construction by the Court;" Case No. 6:12-cv-01380; M.D. Florida; Mar. 15, 2013; 8 pages.

(56) References Cited

OTHER PUBLICATIONS

*Bonutti Skeletal Innovations LLC* v. *Arthrex*; "Defendant Arthrex Inc.'s Preliminary Identification of Proposed Claim Terms for Construction by the Court;" Case No. 6:13-cv-00620; M.D. Florida; Oct. 16, 2013; 8 pages.

*Bonutti Skeletal Innovations LLC* v. *Arthrex*; "Defendant Arthrex, Inc.'s Disclosure of Preliminary Non-Infringement and Invalidity Contentions;" With Exhibits; Case No. 6:13-cv-00620; M.D. Florida; Sep. 23, 2013; 1751 pages.

*Bonutti Skeletal Innovations LLC* v. *Arthrex*; "Defendant Arthrex, Inc.'s Notice of a First Supplemental Disclosure of Preliminary Invalidity Contentions;" With Exhibits; Case No. 6:13-cv-00620; M.D. Florida; Oct. 24, 2013; 660 pages.

*Bonutti Skeletal Innovations LLC* v. *Arthrex*; "Defendant Arthrex, Inc.'s Preliminary Constructions of Terms Proposed for Construction by the Court;" Case No. 6:13-cv-01380; M.D. Florida; Mar. 25, 2013; 11 pages.

*Bonutti Skeletal Innovations LLC* v. *Arthrex*; "Defendant Arthrex, Inc.'s Preliminary Constructions of Terms Proposed for Construction by the Court;" With Exhibit; Case No. 6:12-cv-00620; M.D. Florida; Nov. 1, 2013; 27 pages.

*Bonutti Skeletal Innovations LLC* v. *Arthrex*; "Defendant Arthrex, Inc.'s Supplemental Claim Construction Statement;" Case No. 6:13-cv-00620; M.D. Florida; Nov. 15, 2013; 9 pages.

*Bonutti Skeletal Innovations LLC* v. *Arthrex*; "First Amended Complaint with Exhibits" Case No. 6:12-cv-01380; M.D. Florida; Sep. 21, 2012; 259 pages.

*Bonutti Skeletal Innovations LLC* v. *Arthrex*; "Joint Claim Construction Statement;" Case No. 6:13-cv-00620; M.D. Florida; Nov. 15, 2013; 25 pages.

*Bonutti Skeletal Innovations LLC* v. *Arthrex*; "Consent Joint Motion for Leave to File Corrected Joint Claim Construction Statement Exhibit;" Case No. 6:13-cv-00620; M.D. Florida; Dec. 12, 2013; 23 pages.

*Bonutti Skeletal Innovations LLC* v. *Arthrex*; "Notice of Filing Corrected Joint Claim Construction Statement;" Case No. 6:13-cv-00620; M.D. Florida; Dec. 23, 2013; 21 pages.

*Bonutti Skeletal Innovations LLC* v. *Arthrex*; "Plaintiff Bonutti Skeletal Innovations LLC's Proposed Interpretations of Disputed Claim Terms;" With Exhibits; Case No. 6:13-cv-00620; M.D. Florida; Nov. 1, 2013; 34 pages.

*Bonutti Skeletal Innovations LLC* v. *Arthrex*; "Plaintiffs Initial Preliminary Identification of Claim Terms and Phrases Potentially Needing Interpretation by the Court;" Case No. 6:13-cv-01380; M.D. Florida; Mar. 15, 2013; 5 pages.

*Bonutti Skeletal Innovations LLC* v. *Arthrex*, "Order," Case No. 6:13-cv-620; M.D. Florida, Mar. 25, 2014, 29 pages.

*Bonutti Skeletal Innovations LLC* v. *DePuy Mitek LLC, et al.*; "Declaration of Stephen M. Belkoff, PH.D in Support of Plaintiff Bonutti Skeletal Innovations LLC's Preliminary Claim Construction Brief;" Civil Action No. 1:12-cv-11667; United States District Court District of Massachusetts; Dec. 9, 2013; 49 pages.

*Bonutti Skeletal Innovations LLC* v. *DePuy Mitek LLC, et al.*; "Defendants' List of Proposed Claim Terms and Phrases for Interpretation;" Civil Action No. 1:12-cv-11667; United States District Court District of Massachusetts; Oct. 3, 2013; 6 pages.

*Bonutti Skeletal Innovations LLC* v. *DePuy Mitek LLC, et al.*; "Defendants' Preliminary Invalidity Disclosures;" Civil Action No. 1:12-cv-11667; United States District Court District of Massachusetts; Aug. 29, 2013; 73 pages.

*Bonutti Skeletal Innovations LLC* v. *DePuy Mitek LLC, et al.*; "Defendants' Preliminary Non-Infringement Disclosures;" Civil Action No. 1:12-cv-11667; United States District Court District of Massachusetts; Aug. 29, 2013; 86 pages.

*Bonutti Skeletal Innovations LLC* v. *DePuy Mitek LLC, et al.*; "Defendants' Proposed Claim Constructions;" Civil Action No. 1:12-cv-11667; United States District Court District of Massachusetts; Oct. 10, 2013; 7 pages.

*Bonutti Skeletal Innovations LLC* v. *DePuy Mitek LLC, et al.*; "Depuy's Opening Claim Construction Brief;" Civil Action No. 1:12-cv-11667; United States District Court District of Massachusetts; Dec. 9, 2013; 35 pages.

*Bonutti Skeletal Innovations LLC* v. *DePuy Mitek LLC, et al.*; "Joint Appendices A through I;" Civil Action No. 1:12-cv-11667; United States District Court District of Massachusetts; Dec. 9, 2013; 413 pages.

*Bonutti Skeletal Innovations LLC* v. *DePuy Mitek LLC, et al.*; "Plaintiff Bonutti Skeletal Innovations LLC's Claim Construction Reply Brief;" Civil Action No. 1:12-cv-11667; United States District Court District of Massachusetts; Jan. 16, 2014; 24 pages.

*Bonutti Skeletal Innovations LLC* v. *DePuy Mitek LLC, et al.*; "Plaintiff Bonutti Skeletal Innovations LLC's List of Proposed Claim Terms and Phrases for Interpretation;" Civil Action No. 1:12-cv-11667; United States District Court District of Massachusetts; Oct. 3, 2013; 4 pages.

*Bonutti Skeletal Innovations LLC* v. *DePuy Mitek LLC, et al.*; "Plaintiff Bonutti Skeletal Innovations LLC's Preliminary Claim Construction Brief;" Civil Action No. 1:12-cv-11667; United States District Court District of Massachusetts; Dec. 9, 2013; 27 pages.

*Bonutti Skeletal Innovations LLC* v. *DePuy Mitek LLC, et al.*; "Plaintiff Bonutti Skeletal Innovations LLC's Response to Defendants' Proposed Claim Constructions;" Civil Action No. 1:12-cv-11667; United States District Court District of Massachusetts; Oct. 30, 2013; 14 pages.

*Bonutti Skeletal Innovations LLC* v. *DePuy Mitek LLC, et al.*; "Plaintiff's Initial Preliminary Infringement Disclosures;" Civil Action No. 1:12-cv-11667; United States District Court District of Massachusetts; May 30, 2013; 8 pages.

*Bonutti Skeletal Innovations LLC* v. *DePuy Mitek LLC, et al.*; "DePuy's Reply Claim Construction Brief;" Civil Action No. 1:12-cv-11667; United States District Court District of Massachusetts; Jan. 16, 2014; 23 pages.

Amis, Andrew A.; "Anterior Cruciate Ligament Graft Positioning, Tensioning, and Twisting;" Knee Surgery, Sports Traumatology, Arthroscopy, 6 [Suppl. 1]; 1998; pp. S2-S12.

Amis, Andrew A.; "Anterior Cruciate Ligament Replacement, Knee Stability and the Effects of Implants;" The Journal of Bone and Joint Surgery, 71-B; 1989; pp. 819-824.

Andersen, Henrik Norholm, et al.; "The Immediate Postoperative Kinematic State After Anterior Cruciate Ligament Reconstruction with Increasing Peroperative Tension;" Knee Surger, Sports Traumatology, Arthroscopy, 6[Suppl. 1]; 1998; pp. S62-S69.

Barber, F. Alan, et al.; "Suture Anchor Failure Strength—An In Vivo Study;" Arthroscopy: The Journal of Arthroscopic and Related Surgery, vol. 9, No. 6; 1993; pp. 647-652.

Barber, F. Alan; "The Ultimate Strength of Suture Anchors;" Arthroscopy: The Journal of Arthroscopic and Related Surgery, vol. 11, No. 1; Feb. 1995, pp. 21-28.

Barrett, Gene R., et al.; "T-Fix Endoscopic Meniscal Repair: Technique and Approach to Different Types of Tears;" Arthroscopy, vol. 11, No. 2; pp. 245-251.

Barrows, Thomas H., et al.; "Synthetic Bioabsorbable Polymers;" High Performance Biomaterials: A Comprehensive Guide to Medical and Pharmaceutical Applications 243 (Michael Szycher ed.); 1991.

Bylski-Austrow, D.I., et al.; "Anterior Cruciate Ligament Replacements: A Mechanical Study of Femoral Attachment Location, Flexion Angle at Tensioning, and Initial Tension;" Journal of Orthopaedic Research, 8; 1990; pp. 522-531.

Diduch, et al.; "Modern Concepts in Arthroscopic Bankart Repair;" Journal of Long Term Effects of Medical Implants, 9(2&3); 1999; pp. 377-393.

Escalas, F., et al.; "T-Fix Anchor Sutures for Arthroscopic Meniscal Repair;" Knee Surgery, Sports Traumatol, Arthroscopy; 1997, vol. 5, pp. 72-76.

Flory, Principles of Polymer Chemisty, 1953, selected pages.

Gao et al., Swelling of Hydroxypropyl Methycellulose Matrix Tablets . . . , J. of Pharmaceutical Sciences, vol. 85, No. 7, Jul. 1996, p. 732-740.

Gopferich, Mechanisms of polymer degradation and erosion, Biomaterials, 1996, vol. 17, No. 2, p. 103-114.

(56) References Cited

OTHER PUBLICATIONS

Grizzi; "Hydrolytic degradation of devices based on poly(DL-lactic acid) size-dependence;" Biomaterials, 1995, vol. 16, No. 4; pp. 305-11.

Grumbine, et al.; "Grappling Suture Fixation Technique;" Clin Podiatr Med Surg. 3(2); 1986; pp. 235-239.

Hanna, et al.; "Repair of Distal Tendo Achillis Rupture With the Use of the Mitek Anchor System;" J Am Podiatr Med Assoc, 83(12); Dec. 1993; pp. 663-668.

Hecker et al.; Pull-out strength of suture anchors for rotator cuff and Bankart lesion repairs, Nov.-Dec. 1993, The American Journal of Sports Medicine, vol. 21, No. 6 p. 874-9.

ISR—International Search Report, WO/2009/029908, published Oct. 28, 2008 for PCT/US2008/074941.

Karlsson, J. et al; "Repair of Bankart Lesions With a Suture Anchor in Recurrent Dislocation of the Shoulder;" Scand. J. of Med & Science in Sports, 1995, 5:170-174.

Kurosaka, Masahiro, et al.; "A Biomechanical Comparison of Different Surgical Techniques of Graft Fixation in Anterior Cruciate Ligament Reconstruction;" The American Journal of Sports Medicine, vol. 15, No. 3; 1987; pp. 225-229.

Lambert, Kenneth L.; "Vascularized Patellar Tendon Graft with Rigid Internal Fixation for Anterior Cruciate Ligament Insufficiency;" Clinical Orthopaedics and Related Research, No. 172; Jan.-Feb. 1983; pp. 85-89.

Linvatec, Impact Suture Anchor brochure, 2004.

Markolf, Keith L., et al.; "Biomechanical Consequences of Replacement of the Anterior Cruciate Ligament with a Patellar Ligament Allograft;" The Journal of Bone and Joint Surgery, vol. 78-A, No. 11; Nov. 1996; pp. 1720-1727.

Ming Li; Structure-Property Relationships in the Case of the Degradation of Massive Aliphatic Poly-(α-Hydroxy Acids) in Aqueous Media (Parts 1-3) Journals of Materials Science: Materials in Medicine 1; 1990; pp. 123-139 and 198-206.

Nabors, Eric D., et al.; "Anterior Cruciate Ligament Graft Tensioning in Full Extension;" The American Journal of Sports Medicine, vol. 23, No. 4; 1995; pp. 488-492.

Nativ, O., et al.; "Bladder Neck Suspension Using Bone Anchors for the Treatment of Female Stress Incontinence;" ASAIO J., 43(3); May-Jun. 1997; pp. 204-208.

Obrist, J. et al.; "Bankart Operation With the Mitek Anchor System;" Unfallchirurgie, 17(4); Aug. 1991; pp. 208-212.

Pol E. Huijsmans, et al., "Arthroscopic Rotator Cuff Repair with Double Row Fixation," The Journal of Bone and Joint Surgery, Jun. 2007, vol. 89-A, No. 6, pp. 1248-1257.

Richmond, Modificatio of the Bankart Reconstruction with a Suture Anchor, Am J Sports Med, vol. 19, No. 4, p. 343-346, 1991.

Rodgers, et al.; "The Use of Osseous Suture Anchors in the Treatment of Severe, Complicated Elbow Dislocations;" Am J. Orthrop, 25(11); Nov. 1996; pp. 794-798.

Seitz et al.; "Repair of the Tibiofibular Syndesmosis with a Flexible Implant;" Journal of Orthopaedic Trama, vol. 5, No. 1; p. 78-82, 1991.

Meniscus Replacement with Bone Anchors: A Surgical Technique, Arthroscopy: The Journal of Arcioscopic and Related Surgery, 1994.

Snyder, SJ; "Evaluation and Treatment of the Rotator Cuff;" Orthop Clin North Am, 24(1); Jan. 1993; pp. 173-192.

Steiner, Mark E., et al.; "Anterior Cruciate Ligament Graft Fixation;" The American Journal of Sports Medicine, vol. 22, No. 2; 1994; pp. 240-247.

Suchenski, Maureen, et al.; "Material Properties and Composition of Soft-Tissue Fixation;" 26 Arthroscopy: The Journal of Arthroscopy and Related Surgery 822, vol. 26, No. 6; 2010, pp. 821-831.

Taylor, David E., et al.; "Femoral Bone Plug Recession in Endoscopic Anterior Cruciate Ligament Reconstruction;" Arthoscopy: The Journal of Arthroscopic and Related Surgery, vol. 12, No. 4; Aug. 1996; pp. 513-515.

Tohyama, Harukazu, et al.; "Significance of Graft Tension in Anterior Cruciate Ligament Reconstruction;" Knee Surgery, Sports Traumatology, Arthroscopy, 6 [Suppl. 1]; 1998; pp. S30-S37.

Verhaven, E., et al.; "Surgical Treatment of Acute Biceps Tendon Ruptures With a Suture Anchor;" Acta Orthop Belg, 59(4); 1993; pp. 426-429.

Van Heerwaarden, R.J., et al.; "Effect of Pretension in Reconstructions of the Anterior Cruciate Ligament With a Dacron Prosthesis;" Knee Surgery, Sports Traumatology, Arthroscopy, 3; 1996; pp. 202-208.

Van Kampen, Albert, et al.; "The Effect of Different Graft Tensioning in Anterior Cruciate Ligament Reconstruction: A Prospective Randomized Study;" The Journal of Arthroscopy and Related Surgery, vol. 14, No. 8; Nov.-Dec. 1998; 1998; pp. 845-850.

Weinraub, et al.; "A New Method for Reattachment of the Tendo Achillis Following Retrocalcaneal Exostectomy;" J Foot Ankle Surg, 37(2); Mar.-Apr. 1998; pp. 86-95.

Westrich, et al.; "Isolated Rupture and Repair of the Popliteus Tendon;" Arthoscopy, 11(5); Oct. 1995; pp. 628-632.

Yamamoto, Yuhei, et al.; "Application of a Suture Anchor Technique for Flap Fixation to Bone;" Journal of Reconstructive Microsurgery; Jul. 1996, vol. 12, No. 5, pp. 313-315.

Yoshiya, Shinichi, et al.; "Graft Tension in Anterior Cruciate Ligament Reconstruction;" The American Journal of Sports Medicine, vol. 15, No. 5; 1987, pp. 464-470.

Copending U.S Appl. No. 11/230,020, Final Office Action dated Aug. 2, 2011.

Copending U.S. Appl. No. 12/030,728, Response to Office Action Sep. 21, 2011.

*Bonutti Skeletal Innovations LLC v. DePuy Mitek LLC, et al.*; "Memorandum and Order on Claim Construction;" Civil Action No. 1:12-cv-11667; United States District Court District of Massachusetts; May 2, 2014; 22 pages.

\* cited by examiner

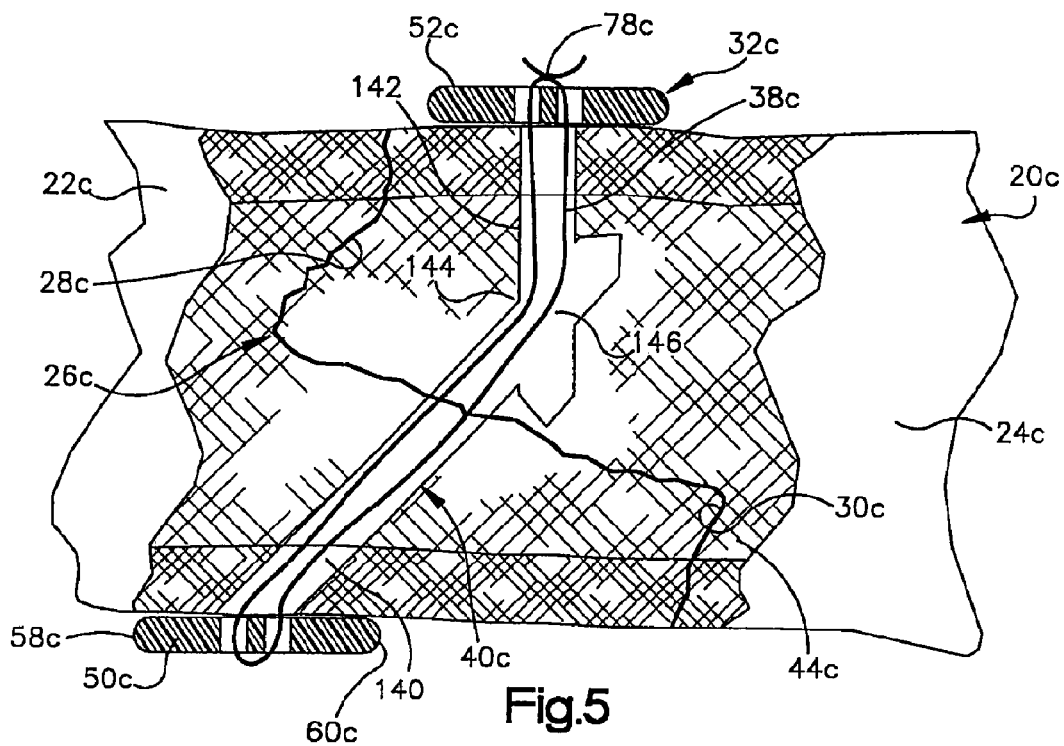
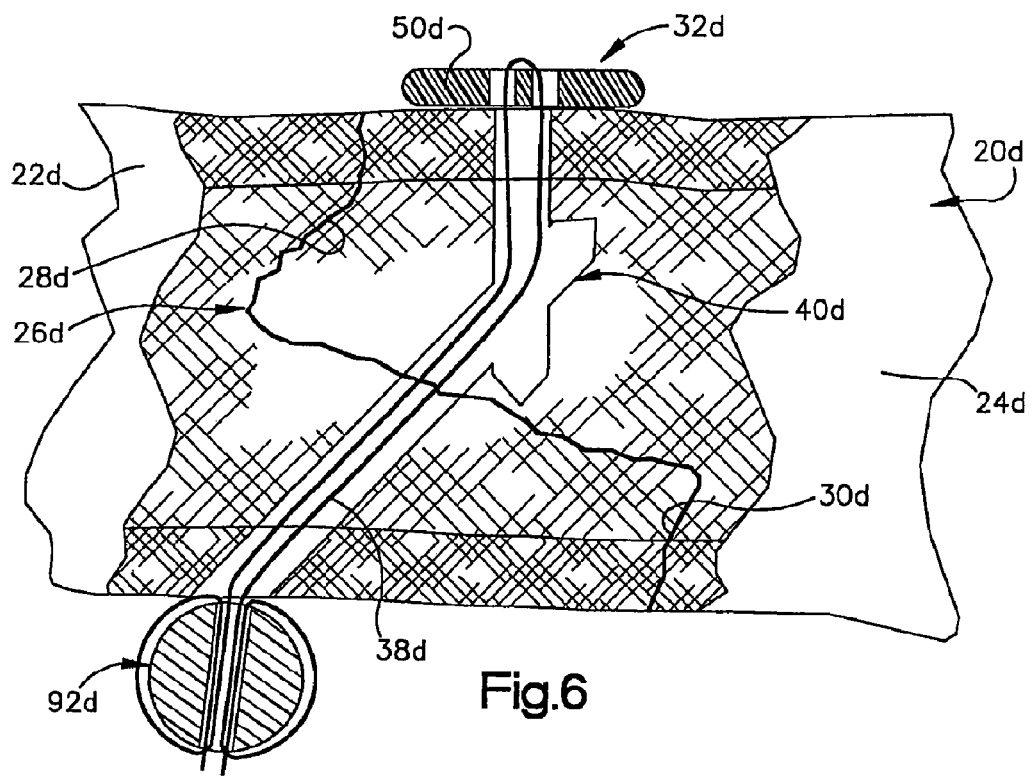

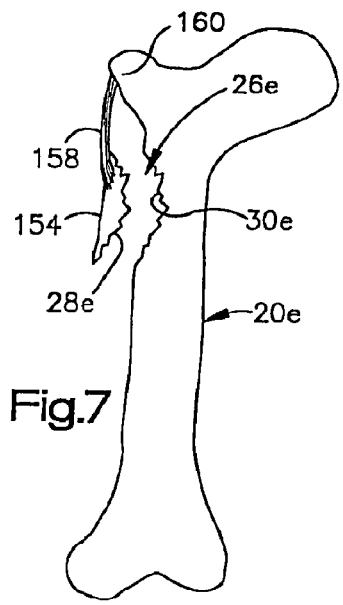
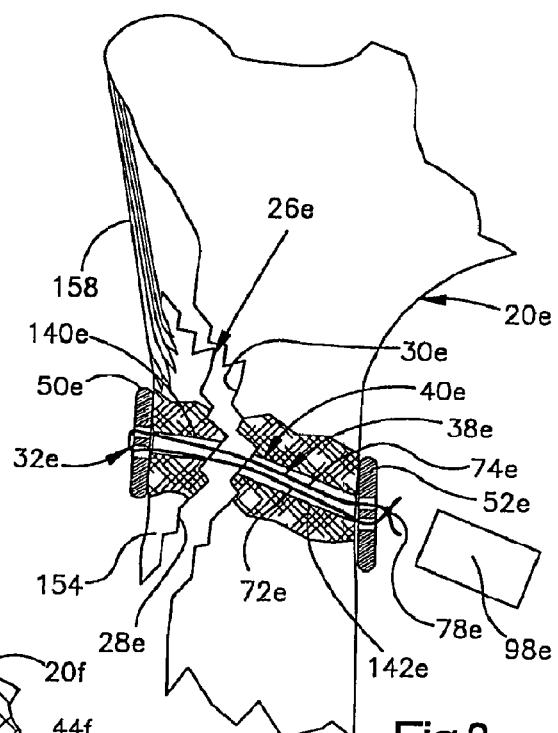
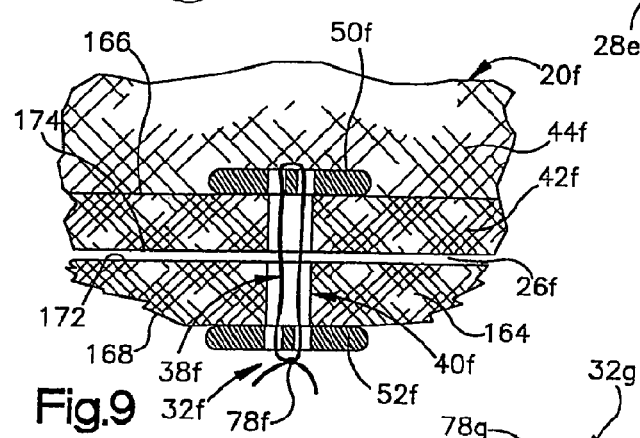
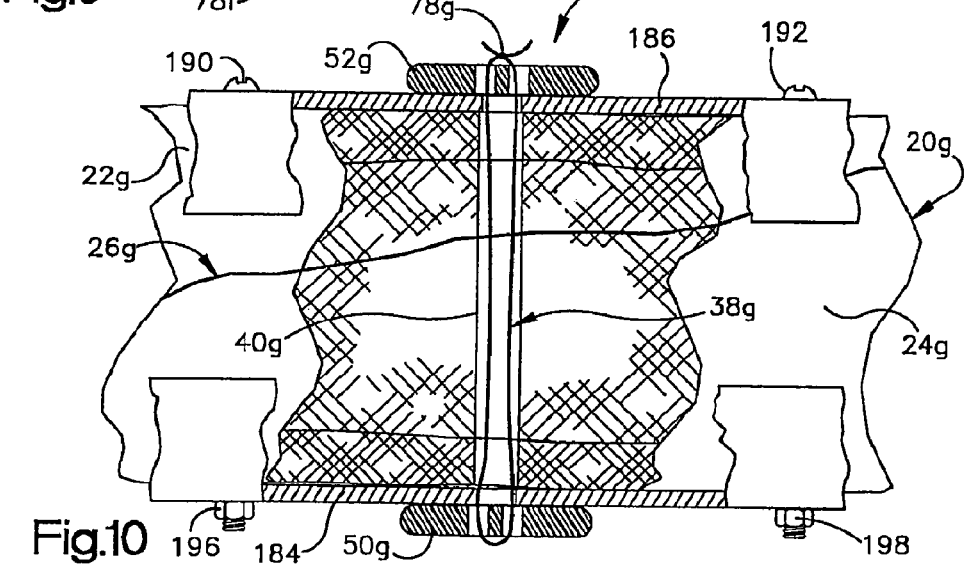

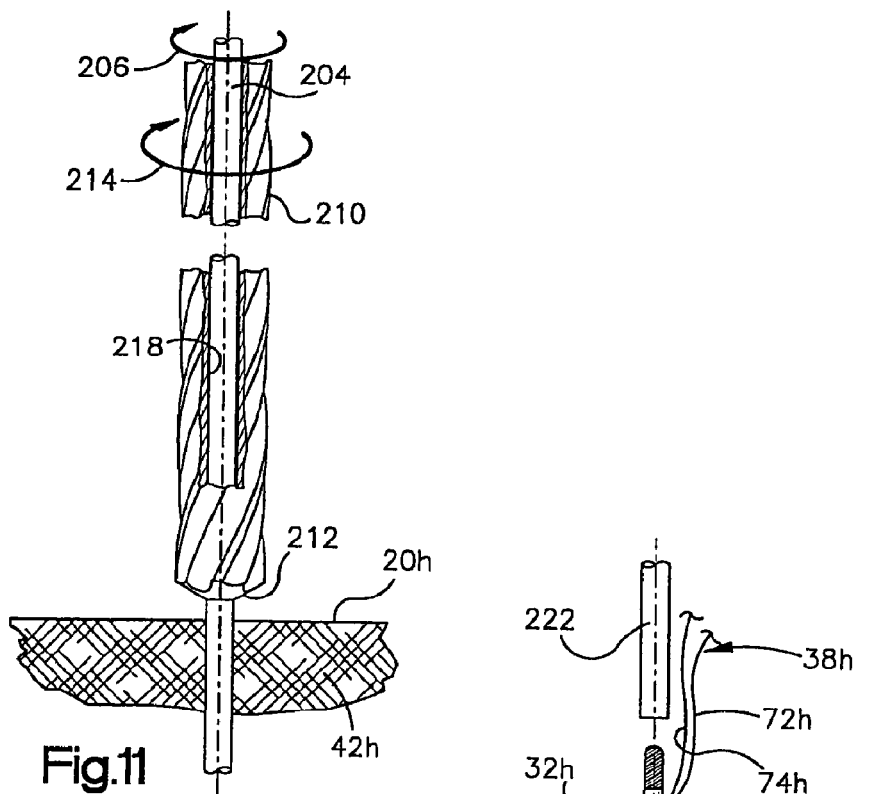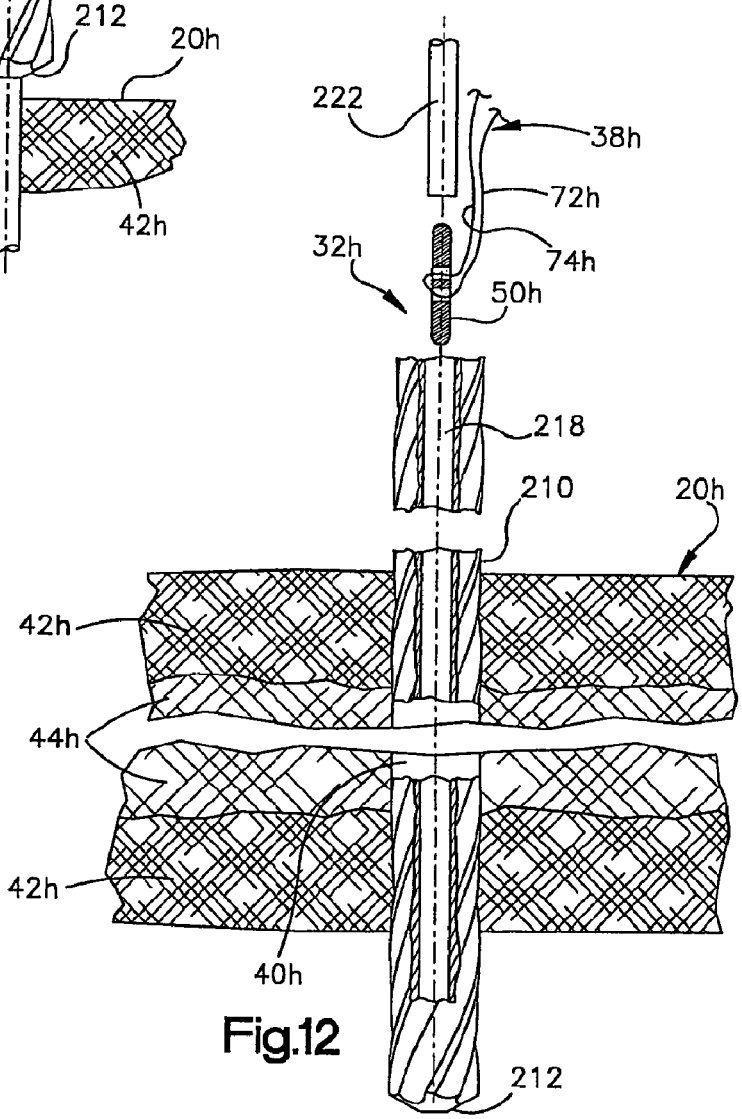

APPARATUS AND METHOD FOR SECURING A PORTION OF A BODY

CROSS-REFERENCE TO RELATED APPLICATIONS

This application is a continuation of U.S. patent application Ser. No. 12/359,364 filed Jan. 26, 2009, now U.S. Pat. No. 8,147,514. The aforementioned application Ser. No. 12/359,364 is itself a continuation of U.S. patent application Ser. No. 10/685,117 filed Oct. 14, 2003, now U.S. Pat. No. 7,481,825. The aforementioned application Ser. No. 10/685,117 is itself a continuation of U.S. patent application Ser. No. 09/835,473 filed Apr. 16, 2001, now U.S. Pat. No. 6,638,279. The aforementioned application Ser. No. 09/835,473 is itself a continuation of U.S. patent application Ser. No. 09/532,942 filed Mar. 22, 2000, now U.S. Pat. No. 6,238,395. The aforementioned application Ser. No. 09/532,942 is itself a continuation of U.S. patent application Ser. No. 09/363,707 filed Jul. 29, 1999, now U.S. Pat. No. 6,045,551. The aforementioned application Ser. No. 09/363,707 is itself a continuation-in-part of U.S. patent application Ser. No. 09/323,488 filed Jun. 1, 1999, now U.S. Pat. No. 6,117,160. The aforementioned application Ser. No. 09/323,488 is itself a continuation of U.S. patent application Ser. No. 09/019,977 filed Feb. 6, 1998, now U.S. Pat. No. 5,921,986. The benefit of the earlier filing dates of the aforementioned applications and patents is claimed.

BACKGROUND OF THE INVENTION

The present invention relates to a new and improved method and apparatus for securing sections of a fractured bone and/or securing body tissue to bone.

When a bone is broken or fractured, it is necessary to press sections of the bone on opposite sides of the fracture together in order to promote healing of the bone. Bone screws have been used with or without metal plates to hold the sections of the fractured bone against movement relative to each other. In addition, it has been suggested that avulsion fractures could be treated by using wire sutures between sections of bone in a matter similar to that disclosed in U.S. Pat. No. 5,474,554. It has also been suggested that an anchor could be retained in a bone is a manner disclosed in U.S. Pat. Nos. 5,527,343 and 5,534,012.

SUMMARY OF THE INVENTION

The present invention relates to a method of securing sections of a fractured bone. Sections of a fractured bone are held against movement relative to each other.

In accordance with one aspect of the present invention, there is provided a bone suture assembly for treating a fracture of a bone. The bone suture assembly includes a first bone plate positioned proximate to the bone and a suture positioned through the first bone plate and across the fracture of the bone to thereby stabilize the fracture. The suture assembly may include a second bone plate positioned proximate to the bone generally opposite the first bone plate. The suture may be positioned through the second bone plate to stabilize the fracture. The suture assembly may also include a passage through the bone and across the fracture, wherein the suture is disposed within the passage. The passage may be nonlinear and may include a tubular member. The suture may be disposed within the tubular member.

Furthermore, the bone suture assembly may include at least one fastener to hold the first bone plate to the bone. At least one fastener may extend across the fracture of the bone and may extend through the bone and through the second bone plate. At least one fastener may also include a screw and nut. Additionally, the suture assembly may include a tubular member in the bone positioned across the fracture, and the suture may be disposed within the tubular member. The tubular member may be packed with bone particles or bone osteoinductive protein.

In accordance with another aspect of the present invention, the bone suture assembly includes a first suture anchor positioned proximate to the bone, a first bone plate positioned between the first suture anchor and the bone, and a suture positioned across the fracture of the bone to stabilize the fracture. The suture has a first end portion disposed through the bone plate and attached to the first suture anchor. The suture assembly may also include a second suture anchor positioned proximate to the bone generally opposite the first suture anchor. The second suture anchor may be attached to a second end portion of the suture.

Moreover, the bone suture assembly may include a second bone plate positioned between the second suture anchor and the bone. The suture assembly may also include a passage through the bone and across the fracture, wherein the suture is disposed within the passage. In the present invention, the first and second suture anchors may be suture retainers which may have deformable material to hold the suture retainers to the suture.

In accordance with still another aspect of the present invention, a method for treating a fracture of a bone is provided. The method includes positioning at least one suture anchor proximate to the bone, positioning at least one bone plate between at least one suture anchor and the bone, and moving at least one suture across the fracture of the bone and through at least one bone plate. The method also includes attaching at least one suture to at least one suture anchor and tensioning at least one suture to stabilize the fracture of the bone. At least one suture anchor may be a suture retainer.

In addition, the method may include fastening at least one bone plate to the bone with at least one screw. At least one screw may have a length less than the diameter of the bone, and at least one screw may have a length greater than the diameter of the bone. At least one screw may include at least one nut, and at least one screw may extend across the fracture of the bone.

Furthermore, the method may include forming at least one passage through the bone and moving at least one suture through at least one passage. Also, at least one suture attached to at least one suture anchor may be moved through at least one passage. The method may also include changing the orientation of at least one suture anchor from a first to a second configuration thereby causing at least one suture anchor to become proximate to the bone and impassable through at least one passage. Finally, the method may include tensioning at least one suture between at least two suture anchors to stabilize the fracture of the bone.

BRIEF DESCRIPTION OF THE DRAWINGS

The foregoing and other features of the invention will become more apparent upon a consideration of the following description taken in connection with the accompanying drawings wherein:

FIG. 5 is a schematic illustration, generally similar to FIGS. 2-4, illustrating the manner in which a suture extends between suture anchors through a nonlinear passage;

FIG. 6 is a schematic illustration, generally similar to FIG. 5, illustrating the manner in which a suture extends between a suture anchor and a suture retainer through a nonlinear passage;

FIG. 7 is a schematic illustration depicting a bone which has been fractured in such a manner as to have a bone fragment connected with the bone by muscle or other fibrous tissue;

FIG. 8 is a schematic illustration depicting the manner in which the bone fragment of FIG. 7 is connected to the bone by a suture and a pair of suture anchors;

FIG. 9 is a schematic illustration depicting the manner in which a bone fragment is connected with a bone by a suture which extends between an anchor within the bone and an anchor which engages the bone fragment;

FIG. 10 is a schematic illustration, generally similar to FIGS. 2-4, illustrating in the manner in which plates and rigid fasteners are used in association with a suture and anchors to treat a bone fracture;

FIG. 11 is a schematic illustration depicting the manner in which a thin elongated member is moved through bone and the manner in which a drill is moved along the thin elongated member to enlarge a passage formed in the bone by the thin elongated member;

FIG. 12 is a schematic illustration depicting the manner in which an anchor is moved through a passage in the drill of FIG. 11 after the thin elongated member has been removed from the passage in the drill;

DETAILED DESCRIPTION OF THE INVENTION

Figure 1:
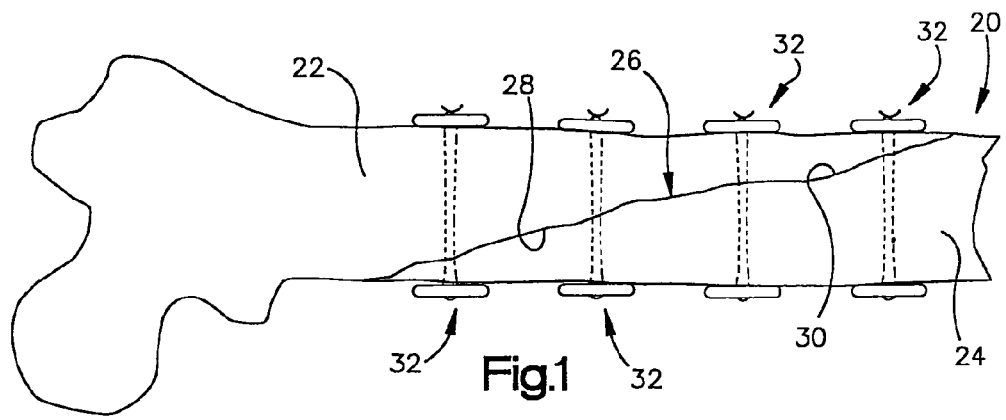
FIG. 1 is a schematic illustration of a bone having a fracture which has been treated with sutures and suture anchors.

A bone 20 which has been fractured is illustrated in FIG. 1. The bone 20 is divided into two sections 22 and 24 by a fracture 26. Opposite side surfaces 28 and 30 of the fracture 26 are pressed together by bone suture assemblies 32.

Figure 2:
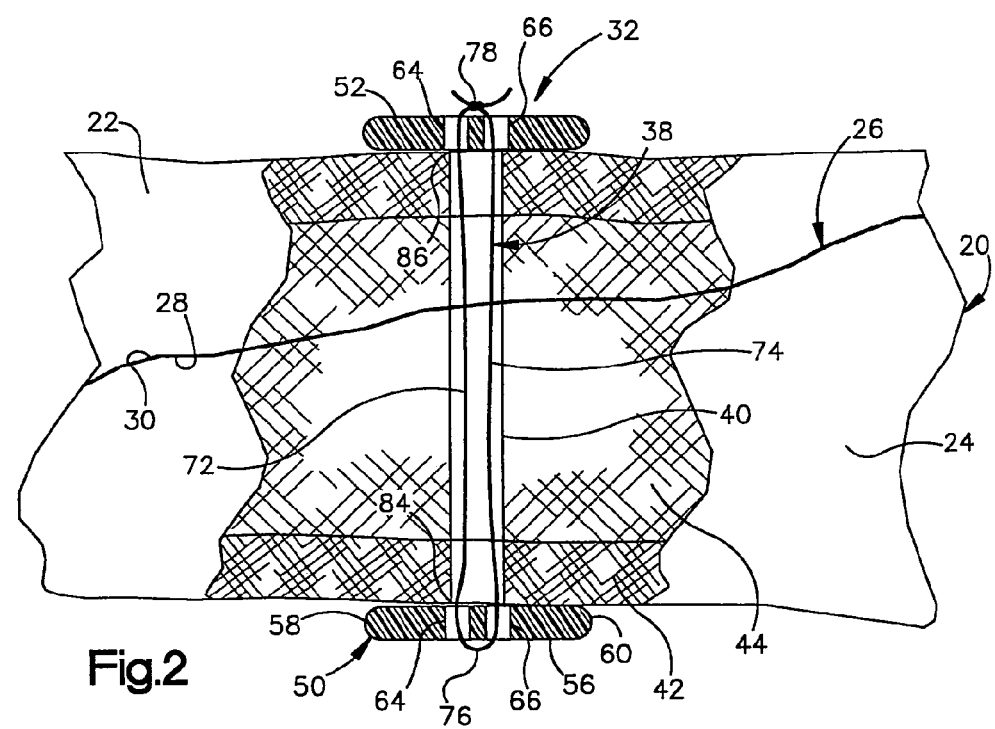
FIG. 2 is an enlarged fragmentary schematic sectional view of a portion of the bone of FIG. 1 and illustrating the manner in which a suture extends across the fracture and interconnects suture anchors on opposite sides of the fracture.

It should be understood that the bone suture assemblies 32 may be utilized in the treatment of any one of many different types of fractures. The fractures may or may not result in the formation of one or more bone fragments. In FIG. 1, the bone suture assemblies 32 have been illustrated as interconnecting sections 22 and 24 of a complete bone fracture of the spiral type. However, the bone suture assemblies 32 could be utilized to connect a fragment of a bone to the main portion of the bone from which the fragment was broken off. Each of the bone suture assemblies 32 has the same construction. However, the bone suture assemblies 32 could have different constructions if desired. The construction of one of the identical bone suture assemblies 32 is illustrated in FIG. 2.

The bone suture assembly 32 (FIG. 2) includes a flexible suture 38 which extends across the fracture 26. The suture 38 is disposed in a straight cylindrical passage 40 which extends diametrically across a generally cylindrical portion of the bone 20. The passage 40 extends through hard compact tissue of an outer layer 42 of the bone and through spongy or cancellous bone tissue 44 which is enclosed by the hard outer layer. Although the passage 40 has a linear configuration, the passage could have a nonlinear configuration if desired.

The suture 38 extends between a first suture anchor 50 disposed on one side of the fracture 26 and a second suture anchor 52 disposed on the opposite side of the fracture. Tension is maintained in the suture 38 to press the suture anchors 50 and 52 against opposite sides of the bone 20 with a predetermined force. This force presses the side surfaces 28 and 30 of the fracture 26 firmly together to promote healing of the fracture. If desired, buttons or other force distributing members could be provided between the anchors 50 and 52 and the bone 20. Body tissue could be disposed between the anchors 50 and 52 and the bone 20.

The suture 38 and/or suture anchors 50 and 52 may be formed of any desired natural or artificial material. For example, the suture 38 may formed of either a polymeric material or a metal. The suture 38 may be biodegradable. Any known suture material may be utilized to form the suture 38.

The suture anchors 50 and 52 have the same construction. However, the anchor 50 could have a construction which is different than the construction of the anchor 52. The anchor 50 has a cylindrical outer side surface 56 which extends between smooth rounded end portions 58 and 60. A pair of parallel cylindrical openings 64 and 66 extend diametrically through the anchor 50. The anchor 50 is free of sharp corners or projections to avoid cutting or abrading of body tissue disposed adjacent to the anchor.

The suture anchor 50 is made of a biocompatible material. Suitable materials include stainless steel or titanium, cobalt chrome and other biocompatible metals. Polymeric material may also be used, suitable polymeric materials includes polyethylene, polypropylene, and biodegradable material such as PLA and PGA. It is believed that it may be preferred to form the suture anchors 50 and 52 from biodegradable or bioerodible copolymers. If desired, the anchor 50 could be formed of body material or hydrophilic materials.

It is contemplated that the anchor 50 may have any desired configuration. For example, the anchor 50 could have any one of the configurations disclosed in U.S. Pat. No. 5,522,846 issued Jun. 4, 1996 and entitled "Suture Anchor". Alternatively, the suture anchor 50 could have the configuration disclosed in U.S. Pat. No. 5,534,012 issued Jul. 9, 1996 and entitled "Method and Apparatus for Anchoring a Suture".

Although the anchor 50 may have any desired configuration, the cross-sectional size of the anchor is such as to enable the anchor to be moved through the passage 40. In addition, the length of the anchor 50 is such as to enable it to span an opening at an end of the passage 40 and transmit force from the suture 38 to a substantial area on the outer layer 42 of the bone 20. It is believed that it will be preferred to form the anchor 50 in such a manner as to eliminate any sharp corners or projections.

In the illustrated embodiment of the invention, the anchor 50 has a cylindrical configuration. This particular anchor has an axial length of about two millimeters and a diameter of about one millimeter. The length of the anchor 50 may be approximately three times the diameter of the anchor. The openings 64 and 66 have a diameter of about one-half millimeter.

It should be understood that the foregoing dimensions have been set forth herein for purposes of clarity of description and it is contemplated that the size of the anchor 50 may vary as a function of the size of the bone being treated. Thus, relatively small anchors may be used in association with treatment of small bones in a wrist, hand, foot or ankle of a patient. Relatively large anchors may be used in association with treatment of larger bones in an arm, shoulder, leg or hip of a patient. It should be understood that the bone suture assembly 32 may be used in conjunction with many different bones other than the specific bones previously mentioned.

Only a single anchor 50 or 52 has been shown at opposite ends of the passage 40. It is contemplated that a plurality of anchors could be provided at each end of the passage 40. For example, a pair of separate or interconnected anchors could be provided in a manner similar to that disclosed in the aforementioned U.S. Pat. No. 5,534,012.

In the embodiment of the invention illustrated in FIG. 2, the suture 38 has a pair of limbs or sections 72 and 74 which extend through the openings 64 and 66 in the suture anchors 50 and 52. A connector section 76 interconnects the two limbs 72 and 74 of the suture 38 and engages a portion of the anchor 50. A knot 78 is formed in the opposite ends of the limbs 72 and 74 to interconnect the two limbs of the suture 38.

When the knot 78 is formed, a predetermined tension is present in the limbs 72 and 74 of the suture 38. This results in the suture anchors 50 and 52 being pressed firmly against the bone 20 with a predetermined force. This predetermined force is maintained during and after tying of the knot 78.

When the bone suture assembly 32 is to be used to treat the fracture 26 in the bone 20, the two sections 22 and 24 of the bone are pressed together at the fracture 26 to align the side surfaces 28 and 30 of the fracture. A drill is then used to form the passage 40 which extends diametrically through the generally cylindrical bone 20. Of course, the passage 40 could be formed by the use of a tool other than a drill. If desired, the passage 40 could have a noncircular cross-sectional configuration.

Once the passage 40 has been formed in the two sections 22 and 24 of the bone 20, a tubular cylindrical member is inserted into the passage 40 and extends diametrically through the bone 20. The leading end of the tubular cylindrical member is aligned with a circular outlet 84 from the passage 40. The opposite end of the tubular member is aligned with a circular inlet 86 to the passage 40. The tubular member has a thin cylindrical wall which engages the sections 22 and 24 of the bone 20. A cylindrical inner side surface of the tubular member defines a passage having a diameter which is only slightly less than the diameter of the passage 40.

By inserting the tubular member into the passage 40, the portions of the passage disposed on opposite sides of the fracture 26 are maintained in alignment. The tubular member may be flexible to enable the tubular member to be inserted into a nonlinear passage 40 through the bone 20. The tubular member may be formed of metal or a polymeric material. If the tubular member is formed of a polymeric material, it may be preferred to form the tubular member from a biodegradable or bioerodible copolymer.

The suture 38 is formed into a loop which extends through the openings 64 and 66 in the anchor 50. At this time, the suture 38 has a length which is substantially greater than the length illustrated in FIG. 2. The cylindrical anchor 50, with the suture 38 connected thereto, is then positioned in axial alignment with the tubular member which extends through the passage 40. Thus, the anchor 50 is moved to an orientation in which a longitudinal central axis of the anchor is coincident with the longitudinal central axis of the cylindrical passage in the tubular member which extends through the passage 40 in the bone 20.

The leading end 58 of the anchor 50 is then moved into the cylindrical tubular member which forms a liner for the passage 40. A pusher member pushes the anchor 50 from an upper (as viewed in FIG. 2) end of the tubular member along the passage 40 in the bone 20 and through the outlet 84 from the passage. As the anchor 50 moves through the passage 40, the suture 38 is pulled through the passage 40 by the anchor.

The orientation of the anchor 50 is then changed from an orientation in which the longitudinal central axis of the anchor 50 is aligned with the longitudinal central axis of the passage 40 to an orientation in which the longitudinal central axis of the anchor 50 extends generally perpendicular to the longitudinal central axis of the passage 40, i.e., the orientation shown in FIG. 2. To pivot the anchor 50 to the orientation shown in FIG. 2, as the anchor emerges from the outlet 84, the suture 38 is tensioned. The combination of the tension in the suture 38 and force applied against the trailing end 60 of the anchor by the pusher member causes the anchor to pivot about the trailing end 60 of the anchor. The pusher member is then withdrawn and the suture tensioned to move the anchor to the position shown in FIG. 2 in a manner similar to that described in the aforementioned U.S. Pat. Nos. 5,527,343 and 5,534,012.

Although it is believed that it may be preferred to change the orientation of the anchor 50 after it has emerged from the passage 40, the anchor could be blocked from reentering the passage in other ways if desired. Thus, the anchor could expand after emerging from the passage 40. This could be accomplished by having spring biased arms held in a retracted position by engagement of spring biased arms with the inner side surface of the tubular cylindrical member which lines the passage 40. Upon emerging from the passage, the arms would move outward under the influence of spring forces and extend radially outward beyond the edge of the exit from the passage 40. If desired, the anchor 50 could be constructed so as to expand in a manner similar to that disclosed in U.S. Pat. No. 5,397,331 and/or U.S. Pat. No. 4,409,974.

Rather than expanding under the influence of stored energy, such as spring force, the anchor 50 could expand by absorbing body fluids. Thus, the anchor 50 may be compressed when it moves through the passage 40 and will expand and absorb body fluids after emerging from the passage 40. It is contemplated that the anchor 50 could be constructed so as to expand in any one of the ways disclosed in U.S. patent application Ser. No. 08/699,553 filed Aug. 19, 1996 by Peter M. Bonutti and entitled "Suture Anchor".

The cylindrical tubular member is then withdrawn from the passage 40. It should be understood that the cylindrical tubular member is used to line the passage 40 in the bone 20 during movement of the anchor 50 through the passage. The use of the tubular member to line the passage 40 may be omitted if desired. However, if the use of the tubular member to line the passage 40 is omitted, the anchor 50 and pusher member would be exposed to the cancellous bone tissue 44 during movement of the anchor through the passage.

The limbs 72 and 74 of the suture 38 are then threaded through openings 64 and 66 in the second suture anchor 52. The limbs 72 and 74 of the suture 38 are tensioned and the second anchor 52 is pressed against the outer side surface of the bone 20. While a predetermined tension force is maintained in the limbs 72 and 74 of the suture 38, the knot 78 is tied in the suture to interconnect the two suture anchors 50 and 52 with the suture 38. The suture 38 is then trimmed to the desired length.

Once the knot 78 has been tied between the limbs 72 and 74 of the suture 38, the tension in the suture 38 presses the side surfaces 28 and 30 of the fracture 26 together. This pressure between the side surfaces 28 and 30 of the fracture 26 is maintained by the suture 38 and suture anchors 50 and 52 until the fracture heals. It is believed that it may be preferred to form the suture 38 and suture anchors 50 and 52 of a biodegradable material which, after the fracture 26 has healed, will dissolve in the patient's body.

The cylindrical tubular member which is inserted into the passage 40 through the bone 20 performs the dual functions of lining the inside of the passage 40 and maintaining the two sections 22 and 24 of the bone in alignment. The cylindrical tubular member could have a slot formed in a side wall of the tubular member to facilitate insertion of the tubular member into the passage 40. It is contemplated that the cylindrical tubular member could be left in the passage 40 after the bone suture assembly 32 has been installed. If the slotted or unslotted cylindrical tubular member is to be left in the passage 40, the cylindrical tubular member may be formed of a biodegradable or bioerodible copolymer. When the cylindrical tubular member remains in the passage 40, the suture 38 extends through the tubular member.

Although only a knot 78 has been shown in FIG. 2 adjacent to the second anchor 52, a suture retainer could be provided to further hold the limbs 72 and 74 of the suture 38. If a suture retainer is to be used in association with the knot 78, the suture retainer will be moved along the limbs of the suture 38 toward the knot before the limbs 72 and 74 of the suture are trimmed to the short length shown in FIG. 2. The suture retainer would then be plastically deformed to grip the limbs 72 and 74 of the suture 38. Thereafter, the suture limbs 72 and 74 would be trimmed to a desired length.

Bone Suture Assembly

Second Embodiment

Figure 3:
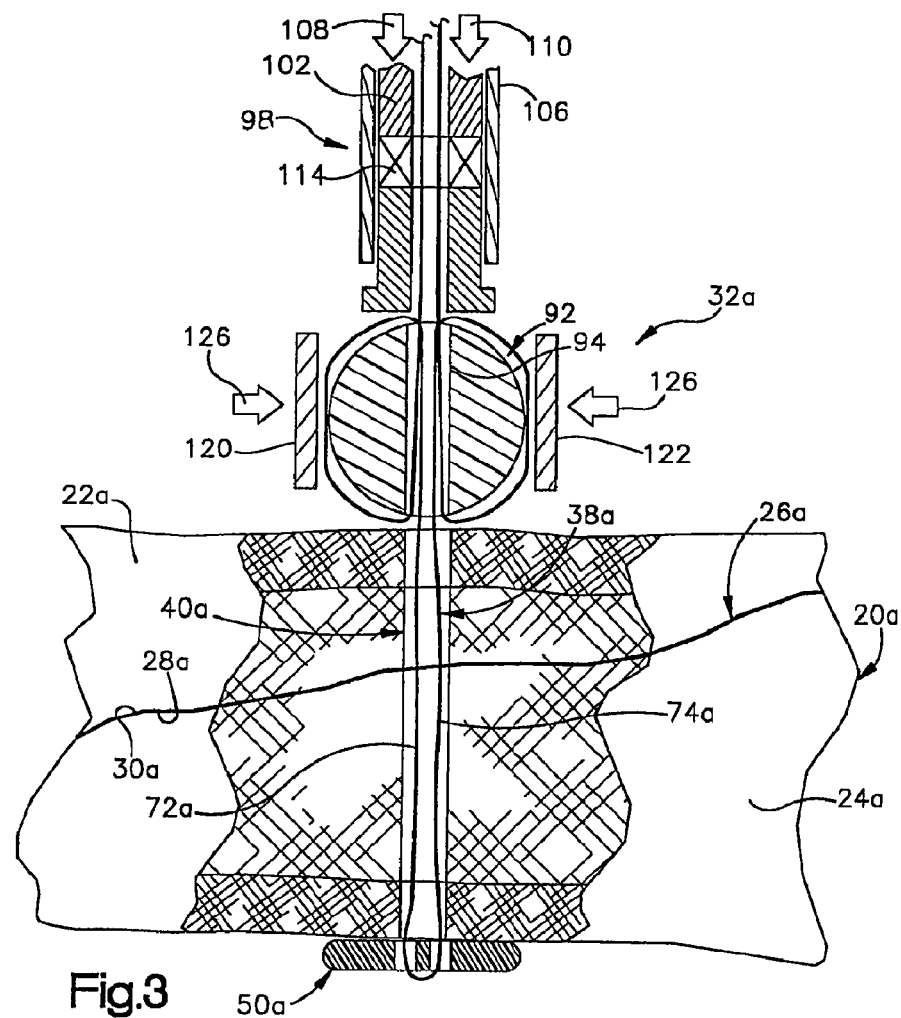
FIG. 3 is a schematic illustration, generally similar to FIG. 2, illustrating the manner in which a suture retainer is used to maintain tension in a suture which extends across a fracture to a suture anchor.

In the embodiment of the invention illustrated in FIG. 2, a pair of suture anchors 50 and 52 are connected with the suture 38 to maintain tension in the suture and pressure against opposite side surfaces 28 and 30 of the fracture 26. In the embodiment of the invention illustrated in FIG. 3, a suture retainer is used in place of one of the suture anchors. Since the embodiment of the invention illustrated in FIG. 3 is generally similar to the embodiment of the invention illustrated in FIG. 2, similar numerals will be utilized to designate similar components, the suffix letter "a" being associated with the embodiment of the invention illustrated in FIG. 3 to avoid confusion.

A bone 20a has sections 22a and 24a which are separated by a fracture 26a. The fracture 26a has side surfaces 28a and 30a which are pressed together by a bone suture assembly 32a. A suture 38a extends through a cylindrical passage 40a which extends diametrically through the generally cylindrical bone 20a. The suture 38a has a pair of limbs or sections 72a and 74a which are connected with a suture anchor 50a. The suture anchor 50a has the same construction as the suture anchor 50 of FIG. 2.

In accordance with a feature of this embodiment of the invention, a suture retainer 92 is used in place of the suture anchor 52 of FIG. 2. The suture retainer 92 has a spherical configuration. A cylindrical passage 94 extends through the center of the spherical suture retainer 92. The sections 72a and 74a of the suture 38a extend around the spherical outer side surface of the suture retainer 92. Thus, a loop is formed in each of the sections 72a and 74a around portions of the suture retainer 92.

If desired, the suture retainer 92 could have a different configuration. For example, the suture retainer 92 could have an oval or elliptical configuration. Although the passage 94 has a linear central axis, the passage could have a nonlinear central axis. If desired, a plurality of passages having the same or different configurations could be provided in the suture retainer 92.

After the suture 38a has been inserted through the suture retainer 92, in the manner illustrated schematically in FIG. 3, the suture retainer 92 is moved along the sections 72a and 74a of the suture 38a toward the bone 20a. The suture retainer 92 is formed as one piece of a polymeric material having a relatively low coefficient friction. Therefore, the two sections 72a and 74a of the suture 30a can readily slide along the surfaces of the suture retainer 52a while the suture retainer moves toward the bone 20a.

A predetermined tension is maintained in the sections 72a and 74a of the suture 38a while the suture retainer 92 is pressed against the bone 20a. This results in the suture 38a being pulled tightly against the suture anchor 50a. The tension in the suture 38a is effective to press the suture anchor 50a and retainer 92 against opposite sides of the bone 20a with a predetermined force.

Once the suture retainer 92 has been moved along the suture 38a and is being pressed against the bone 20a with a predetermined force, the suture retainer is plastically deformed to grip the sections 72a and 74a of the suture 38a. An apparatus 98 for pressing the suture retainer 92 against the bone 20a includes a tubular cylindrical plunger 102 (FIG. 3) having a cylindrical central passage through which the sections 72a and 74a of the suture 38a extend. The plunger 102 is enclosed by a tubular cylindrical housing 106. The plunger 102 is pressed downward, relative to the housing 106 with a predetermined force, indicated by arrows 108 and 110 in FIG. 3. An annular transducer or load cell 114 provides an output indicative of the magnitude of the force 108 and 110 with which the suture retainer 92 is pressed against the bone 20a by the plunger 102.

While the sections 72a and 74a of the suture 38a are being tensioned with a predetermined force and while the plunger 102 is being pressed against the suture retainer 92 with a predetermined force, the suture retainer 92 is plastically deformed. To plastically deform the suture retainer 92, a plurality of force applying or clamp members 120 and 122 are pressed against the suture retainer 92 with a predetermined minimum force, indicated schematically by arrows 126 in FIG. 3. The force application members 120 and 122 may have an arcuate configuration to conform to the spherical configuration of the suture retainer 92 or may have a flat configuration. The force applied against the suture retainer 92 by the force applying members 120 and 122 is sufficient to cause plastic deformation of the material of the suture retainer.

The force 126 is applied against the suture retainer 92 while the suture retainer is at a temperature which is below the transition temperature of the biodegradable polymer which forms the suture retainer 92. Thus, the suture retainer 92 is at approximately the same temperature as the bone 20a when the force 126 is applied against the suture retainer. The force 126 causes the material of the suture retainer 92 to flow and grip the sections 72a and 74a of the suture 38a.

Upon disengagement of the force application members 120 and 122 from the suture retainer 92, the application of downward (as viewed in FIG. 3) force against the suture retainer 92 is interrupted. The upward tensioning of the sections 72a and 74a of the suture 38a is also interrupted. At this time, the plastically deformed suture retainer 92 securely grips the two sections 72a and 74a of the suture 38a to maintain the tension in the suture 38a. If desired, a knot may be formed between the sections 72a and 74a of the suture as additional protection against the suture working loose over an extended period of time.

The suture retainer 92 may be formed of many different materials. However, it is believed that it will be preferred to form the suture retainer 92 of a biodegradable polymer. One biodegradable polymer which may be utilized is polycaperlactone. Alternatively, the suture retainer 92 could be formed of polyethylene oxide terephthalate or polybutylene terephthalate. It is also contemplated that other biodegradable or bioerodible copolymers could be utilized.

Although it is preferred to form the suture retainer 92 of a biodegradable material, the suture retainer could be formed of a material which is not biodegradable. For example, the suture retainer 92 could be formed of an acetyl resin, such as "DELRIN" (trademark). Alternatively, the suture retainer 92 could be formed of para-dimethylamino-benzenediazo sodium sulfonate, such as "DEXON" (trademark). The construction of the suture retainer 92 and the manner in which is cooperates with the suture 38a is the same as is disclosed in U.S. patent application Ser. No. 08/905,084 filed Aug. 1, 1997 by Peter M. Bonutti et al. and entitled "Method and Apparatus for Securing a Suture".

The suture retainer 92 is plastically deformed to grip the limbs 72a and 74a of the suture 38a. However, the suture retainer 92 could be constructed so as to be mechanically actuated to grip the suture 38a. If desired, a combination of a mechanical gripping action and plastic deformation could be utilized by a retainer to grip the suture 38a.

Retaining Body Tissue Against Bone

Figure 4:
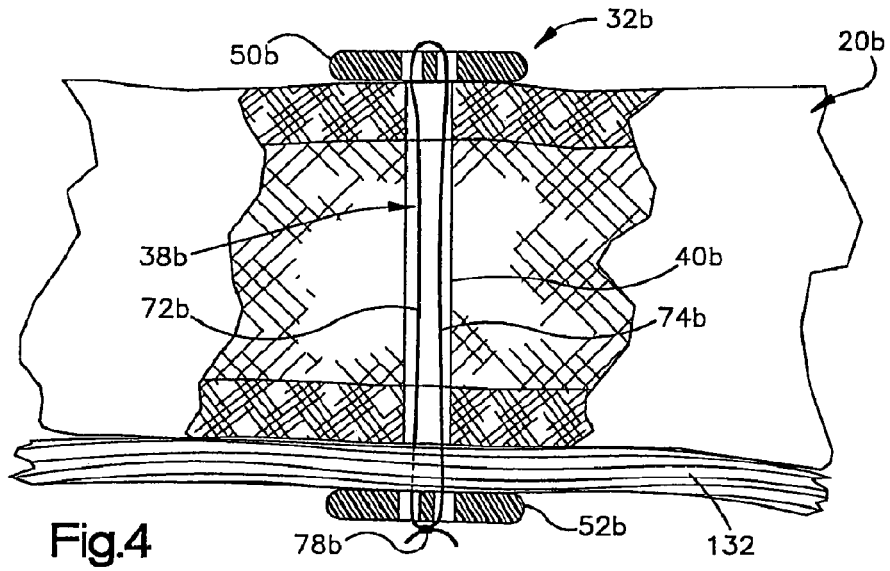
FIG. 4 is a schematic illustration, generally similar to FIGS. 2 and 3, illustrating the manner in which body tissue is connected with a bone using a suture and suture anchors.

In the embodiment of the invention illustrated in FIG. 2, a bone suture assembly 32 is utilized to press surfaces 28 and 30 of a fracture 26 together. In the embodiment of the invention illustrated in FIG. 4, the suture anchor assembly is utilized to hold body tissue against movement relative to a bone. Since the embodiment of the invention illustrated in FIG. 4 is generally similar to the embodiments of the invention illustrated in FIGS. 2 and 3, similar numerals will be utilized in association with similar components, the suffix letter "b" being associated with the numerals of FIG. 4 to avoid confusion.

A cylindrical passage 40b extends diametrically through a generally cylindrical bone 20b. A bone suture assembly 32b is utilized to retain body tissue 132 against movement relative to the bone 20b. The body tissue 132 may be a muscle, ligament, cartilage or other tissue which is to be held against movement relative to the bone 20b.

The bone suture assembly 32b includes a first suture anchor 50b and a second suture anchor 52b. A suture 38b extends through the passage 40b and interconnects the suture anchors 50b and 52b. Tension in the suture 38b presses the body tissue 132 against a side surface area on the bone 20b. The suture 38b has sections or limbs 72b and 74b which extends through openings in the suture anchors 50b and 52b in the manner previously explained. A knot 78b interconnects the sections 72b and 74b of the suture 38b to press the suture anchor 52b firmly against the body tissue 132. Although the illustrated suture has a pair of sections 72b and 74b, the suture could have a single section if desired.

The suture anchor assembly 32b is installed in association with the bone 20b and body tissue 132 in the same manner as previously explained in conjunction with the embodiment of the invention illustrated in FIG. 2. Thus, the passage 40 (FIG. 4) is formed in the bone 20b by drilling or other methods. The body tissue 132 may be offset to one side of the location where the passage 40b is formed during formation of the passage. This enables the passage 40b to be formed in the bone 20b without damaging the body tissue 132.

The suture anchor 50b is moved through the passage 40b with a longitudinal central axis of the suture anchor aligned with the longitudinal central axis of the passage 40b. When the suture anchor 50b emerges from the passage 40b, the anchor is pivoted to the orientation shown in FIG. 4. Alternatively, the anchor 50b may be mechanically expanded after emerging from the passage 40b. A cylindrical tubular member may be used to line the passage 40a during movement of the anchor 50b through the passage in the manner previously described in connection with the embodiment of FIG. 2.

After the anchor 50b has been moved to the position shown in FIG. 4, the body tissue 132 is positioned between the limbs 72b and 74b of the suture 38b. The limbs 72b and 74b of the suture 38b are then inserted through the openings in the suture anchor 52b. While a predetermined tension is maintained in the suture 38b, the knot 78b is tied between the limbs 72b and 74b of the suture. This results in the body tissue 132 being pressed against the bone 20b with a predetermined force. A button or other force distributing member may be provided between the suture anchor 52b and body tissue 132 if desired.

In the embodiment of the invention illustrated in FIG. 4, two suture anchors 50b and 52b are utilized to press the body tissue 132 against the bone 20b. However, a suture retainer could be substituted for one or more of the suture anchors 50b or 52b. For example, a suture retainer having the same construction and installed in the same manner as the suture retainer 92 of FIG. 3 could be substituted for the anchor 52b of FIG. 4. It should be understood that the suture retainer substituted for the anchor 52b of FIG. 4 could have any desired construction. Thus, a suture retainer having the construction of any one of the suture retainers disclosed in the aforementioned U.S. patent application Ser. No. 08/905,084 filed Aug. 1, 1997 by Peter M. Bonutti et al. and entitled "Method and Apparatus for Securing a Suture" could be utilized in place of the anchor 52b and/or the anchor 50b.

When a suture retainer is used in place of the anchor 52b, the suture retainer applies force against the body tissue 132 to press the body tissue against the bone 20b. If desired, a force distribution member could be provided between the suture retainer and the body tissue 132.

Although the passage 40b has been illustrated in FIG. 4 as having a linear configuration, the passage could have a nonlinear configuration if desired.

In the embodiment of the invention illustrated in FIG. 4, body tissue 132 is disposed adjacent to only one side of the bone 20b. However, if desired, body tissue could be disposed adjacent to opposite sides of the bone 20b. The body tissue could be connected with the anchor 50b in many different ways. For example, a separate length of suture could be connected with the body tissue and anchor 50b or with the suture 38b adjacent to the anchor 50b.

An alternative manner of connecting body tissue with the side of the bone adjacent to the anchor 50b would be to insert the body tissue between the limbs 72b and 74b of the suture 36b in the same manner as shown with the anchor 52b. If this is to be done, an end portion of the body tissue may be manually inserted between the limbs 72b and 74b of the suture 38b. If a central portion of the body tissue is to be disposed between the anchor 50b and the bone 20b, the connector section 76b of the suture could be cut. One of the limbs 72b or 74b of the suture would then be separated from the anchor 50b. The body tissue would be inserted between the limbs of the suture 38. The separated end of the suture would then be inserted through the anchor 50b and connected with the other limb of the suture 38b.

In the embodiment of the invention illustrated in FIG. 4, the body tissue 132 is pressed against a bone 20b which has not been fractured. However, it is contemplated that the bone suture assembly 32 could be utilized to perform the dual functions of pressing body tissue against a bone and of pressing opposite side surfaces of a fracture together. This would result in the body tissue being pressed against the bone 20b in the manner illustrated in FIG. 4 and in opposite side surfaces of a fracture being pressed together in the manner illustrated in FIG. 2 for the opposite side surfaces 28 and 30 of the fracture 26.

Nonlinear Suture Passage

In the embodiment of the invention illustrated in FIG. 2, the passage 40 through which the suture 38 extends has a linear configuration. In the embodiment of the invention illustrated in FIG. 5, the passage through which the suture extends has a nonlinear configuration. Since the embodiment of the invention illustrated in FIG. 5 is generally similar to the embodiment of the invention illustrated in FIGS. 2-4, similar numerals will be utilized to identify similar components, the suffix letter "c" being associated with the components of the embodiment of the invention illustrated in FIG. 5 to avoid confusion.

A bone 20c as a fracture 26c which divides the bone into two sections 22c and 24c. Opposite side surfaces 28c and 30c of the fracture 26c are pressed together by a bone suture assembly 32c. The bone suture assembly 32c includes a suture 38c which extends between first and second suture anchors 50c and 52c.

In accordance with a feature of this embodiment of the invention, the suture 38c is disposed in a passage 40c having a nonlinear configuration. Thus, the passage 40c includes a first section 140 which is skewed relative to a second section 142 of the passage 40c. A bend 144 is formed in the passage 40c at an intersection 146 of the first and second sections 140 and 142 of the passage 40c. The flexible suture 38c extends around the bend 144 along a nonlinear path between the suture anchors 50c and 52c. At the bend 144, the suture 38c applies force against the section 24c of the bone 20c urging the section 24c toward the left (as viewed in FIG. 5). This force presses the sections 22c and 24c of the bone 20c firmly together at the fracture 26c.

The suture anchors 50c and 52c have the same cylindrical construction as the suture anchors 50 and 52 in the embodiment of the invention illustrated in FIG. 2. A knot 78c (FIG. 5) is provided between limbs of the suture 38c to maintain a desired tension in the suture 38c. This tension pulls the suture anchors 50c and 52c toward each other. In addition, this tension presses the section 24c of the bone 20c firmly against the section 22c of the bone at the fracture 26c.

The first section 140 of the passage 40c is formed at an angle to and extends through a longitudinal central axis of the generally cylindrical bone 20c. The second section 142 of the passage 40c is formed in a direction perpendicular, i.e., along a radius, of the generally cylindrical bone 20c. The two sections 140 and 142 of the passage 40c terminate in the spongy cancellous bone tissue 44c.

When the suture assembly 32c is to be used to treat the fracture 26c in the bone 20c, the two sections 22c and 24c of the bone are pressed together at the fracture 26c to align the side surfaces 28c and 30c of the fracture. A drill or other hole forming apparatus is then used to form the first section 140 of the passage 40c. The drill or other hole forming apparatus is then used to form the second section 142 of the passage 40c.

When the second section 142 of the passage 40c intersects the first section 140 of the passage 40c, formation of the section 142 of the passage 40c is interrupted.

Once the nonlinear passage 40c has been formed in the two sections 22c and 24c of the bone 20c, a tubular cylindrical liner (not shown) is inserted into the passage 40c. The tubular cylindrical liner may be formed by two separate tubular members which are inserted at opposite ends of the passage 40c. Alternatively, the tubular cylindrical liner may be formed by a single flexible tubular member which is inserted into the section 140 of the passage 40c and then moved around the bend 144 into the section 142 of the passage 40c. It should be understood that the tubular cylindrical liner for the passage 40c could be omitted if desired.

The cylindrical anchor 50c, with the suture 38c connected thereto, is then positioned in axial alignment with the section 142 of the passage 40c. The leading end 58c of the anchor 50c is then moved into the lined section 142 of the passage 40c. A flexible pusher member applies force against the trailing end 60c of the anchor 50c and pushes the anchor around the bend 144 and through the section 140 of the passage 40c.

Alternatively, a flexible wire or other member could be inserted into the section 140 of the passage 40c. The wire would move around the bend 144 and extend outward from the section 142 of the passage. The wire would then be connected with the anchor 50c and suture 38c. The leading end 58c of the anchor 50c would then be inserted into the section 142 of the passage 40c. Tension on the wire would pull the anchor 50c around the bend 144 and out of the section 140 of the passage 40c.

Once the anchor 50c has been moved out of the passage 40c, the tubular liner for the passage may be withdrawn. If a one-piece tubular liner is used, it may be withdrawn from the open end of the section 142 of the passage 40c. If a two-piece liner is used, one of the pieces may be withdrawn from the open end of the passage section 140 and slit to clear the suture 38c. Alternatively, the slit could be formed in the piece of the liner before it is inserted into the passage section 140. The other piece of the liner would be withdrawn from the open end of the passage section 142. Alternatively, the tubular liner for the passage 40c may be left in place. Of course, the use of a tubular liner for the passage 40c may be omitted.

The suture 38c is then threaded through openings in the suture anchor 52c. The suture 38c is then tensioned and the second anchor 52c is pressed against the outer side surface of the bone 20c. While a predetermined tension force is maintained in the suture 38c, the knot 78c is tied.

In the illustrated embodiment of the invention, the two sections 140 and 142 of the passage 40c have a straight cylindrical configuration. However, it is contemplated that the sections 140 and 142 of the passage 40c could have a different configuration if desired. For example, the section 140 and/or 142 of the passage 40c could have a nonlinear central axis and could have a noncircular cross-sectional configuration if desired.

Body tissue, corresponding to the body tissue 132 of FIG. 4 could be disposed between the anchor 50c and/or 52c and the bone 20c. Although the suture 38c has been illustrated as having a pair of limbs or sections which extend between the anchors 50c and 52c, the suture 38c could have a single limb or section if desired. The anchor 50c could mechanically expand, by absorbing body liquid or under the influence of expansion springs, after the anchor has emerged from the passage 40c to prevent the anchor from being pulled back through the passage.

Nonlinear Passage

Second Embodiment

In the embodiment of the invention illustrated in FIG. 5, the bone suture assembly 32c associated with the nonlinear passage 40c includes a pair of suture anchors 50c and 52c. In the embodiment of the invention illustrated in FIG. 6, a suture retainer in substituted for one of the suture anchors in much the same manner as previously described in conjunction with the embodiment of the invention illustrated in FIG. 3. Since the embodiment of the invention illustrated in FIG. 6 is generally similar to the embodiment of the invention illustrated in FIGS. 2-5, similar numerals will be utilized to designate similar components, the suffix letter "d" being associated with the numerals of FIG. 6 in order to avoid confusion.

A bone 20d has a fracture 26d which divides the bone into two sections 22d and 24d. The fracture 26d has side surfaces 28d and 30d which are pressed together by a bone suture assembly 32d. The bone suture assembly 32d includes a suture 38d which extends through a nonlinear passage 40d having the same construction as the nonlinear passage 40c of FIG. 5.

In accordance with a feature of this embodiment of the invention, the bone suture assembly 32d includes a suture anchor 50d having the same construction as the suture anchor 50 of FIG. 2, and a suture retainer 92d having the same construction as the suture retainer 92 of FIG. 3. The suture anchor 50d and suture retainer 92d maintain a predetermined tension in the suture 38d. This results in the suture anchor 50d being firmly pressed against the section 24d of the bone 20d. The suture retainer 92d is firmly pressed against the section 22d of the bone 20d by the tension in the suture 38d.

Since the passage 40d has a nonlinear configuration, the suture 38d is effective to apply a force component to the section 24d of the bone 20d urging the section 24d of the bone toward the left (as viewed in FIG. 6). This results in the surface 30d of the fracture 26d being pressed firmly against the surface 28d of the fracture.

The suture retainer 92d is plastically deformed to grip the suture 38d in the same manner as previously described herein in conjunction with the suture retainer 92 of FIG. 3. However, the suture retainer 92d could be constructed so as to form a mechanical connection with the suture 38d. If desired, a suture retainer could be substituted for the anchor 50d.

Although both the suture retainer 92d and anchor 50d have been illustrated in FIG. 6 as being disposed in engagement with the bone 20d, a force distributing member could be provided between the anchor and/or suture retainer and the bone. It is contemplated that body tissue, similar to the body tissue 132 of FIG. 4, could be disposed between the anchor 50d and/or the suture retainer 92d and the bone 20d.

Tissue Tensioning with Bone Fragment Retaining

In the embodiment of the invention illustrated in FIG. 2, the fracture in a portion of a bone is treated. In the embodiment of the invention illustrated in FIGS. 7 and 8, a fracture results in a fragment of a bone being separated from a main portion of the bone. The bone fragment is connected with the main portion of the bone by muscle, tendon, ligament, cartilage or other fibrous body tissue. In the embodiment of the invention illustrated in FIGS. 7 and 8, the fibrous body tissue is tensioned as the bone fragment is positioned relative to the main portion of the bone. Since the embodiment of the invention illustrated in FIGS. 7 and 8 is generally similar to the embodiment of the invention illustrated in FIGS. 2-6, similar numerals will be utilized to designate similar components, the suffix "e" being associated with the numerals of FIGS. 7 and 8 in order to avoid confusion.

A bone fragment 154 is separate from a main bone 20e (FIG. 7). The fragment 154 is connected with the main bone 20e by fibrous body tissue 158, i.e., muscle, tendon, ligament, cartilage, etc. The fibrous body tissue 158 extends between the bone fragment 154 and a portion 160 of the main bone 20e. The bone fragment 154 has a side surface 28e with a configuration which matches the configuration of a side surface 30e of a fracture 26e which occurred in the main bone 20e.

In order to promote healing of the main bone 20e, a bone suture assembly 32e (FIG. 8) is utilized to pull the bone fragment 154 toward the main bone 20e. As this occurs, the fibrous body tissue 158 is tensioned and the side surface 28e on the bone fragment 154 is pressed against the side surface 30e on the main bone 20e. The bone fragment 154 is pressed firmly against the main bone 20e by the bone suture assembly 32e. Thus, the gap illustrated schematically in FIG. 8, between the side surfaces 28e and 30e of the fracture 26e, is eliminated and the side surfaces of the fracture are pressed firmly together by the bone suture assembly 32e. If desired, the bone fragment 154 may be manually pressed against the main bone 20e before the bone suture assembly is pulled tight.

The bone suture assembly 32e includes a suture 38e having limbs or sections 72e and 74e. The suture 38e extends through openings in a first suture anchor 50e. The suture then extends into a passage 40e formed in the bone fragment 154 and the main bone 20e.

The passage 40e includes a first section 140e which extends through the bone fragment 154. In addition, the passage 40e includes a second section 142e which extend through the main bone 20e. The limbs or section 72e and 74e of the suture 38e extends through a second anchor 52e.

During installation of the bone suture assembly 32e, the limbs 72e and 74e of the suture 38e are gripped by a force or tension measurement device 98e. The tension measurement device 98e includes a load cell which measures the amount of tension applied to the limbs 72e and 74e of the suture 38e.

As tension is applied to the limbs 72e and 74e of the suture 38e, the bone fragment 154 is pulled toward the right (as viewed in FIG. 8) to move the side surface 28e on the bone fragment into alignment with the side surface 30e on the main bone 20e. As this occurs, the fibrous body tissue 158 is stretched or tensioned. While a predetermined force is transmitted through the limbs 72e and 74e to the suture anchor 50e and the bone fragment 154 to firmly press the bone fragment against the main bone 20e, a knot 78e is tied to interconnect the limbs 72e and 74e. While the predetermined tension is maintained and the knot 78e tied, the second anchor 52e is firmly pressed against the side surface of the main bone 20e.

Although the passage 40e could have a linear configuration if desired, in the embodiment of the invention illustrated in FIG. 8, the passage 40e has a nonlinear configuration. Thus, the first section 140e of the passage 40e has a central axis which is skewed relative to a central axis of the second section 142e of the passage 40e. This enables the flexible suture 38e to apply force to the bone fragment 154 having components urging the bone fragment rightward (as viewed in FIG. 8) against the surface 30e on the main bone 20e and downward (as viewed in FIG. 8) to maintain the tension in the fibrous body tissue 158.

When the passage 40e is to be formed in the bone fragment 154 and main bone section 20e, a hole is drilled through the bone fragment 154 to form the first section 140e of the passage. The second portion 142e of the passage 40e is drilled in the main bone 20e. It should be understood that the passage 40e could be formed in many different ways other than drilling. For example, a cutting tool or laser could be used to form the passage 40e.

The second section 142e of the passage 40e has a longitudinal central axis which is skewed at an acute angle relative to the longitudinal central axis of the first section 140e of the passage in the bone fragment 154. Thus, the first portion 140e of the passage 40e in the bone fragment 154 has a central axis which is close to being perpendicular to a longitudinal central axis of the main bone 20e. The second portion 142e of the passage 40e has a longitudinal central axis which is angularly offset to a substantial arc relative to the longitudinal central axis of the main bone 20e.

The anchor 50e is moved through the first section 140e of the passage 40e and positioned in engagement with an outer side surface of the bone fragment. The free ends of the limbs 72e and 74e of the suture 38e are then moved rightward (as viewed in FIG. 8) through the second portion 142e of the passage 40e. The free ends of the suture 38e are then threaded through openings in the second anchor 52e.

After the suture 38e has been inserted through openings in the second anchor 52e, the force or tension measuring device 98e is utilized to pull the free ends of the suture 38e toward the right (as viewed in FIG. 8). This tension pulls the bone fragment 154 into engagement with the main bone 20e. The knot 78e is tied in the free ends of the suture 38e while the tension is maintained in the suture.

If desired, the bone suture assembly 32e could be positioned relative to the bone 20e and the bone fragment 154 by moving the anchor 50e first through the second section 142e of the passage disposed in the main bone 20e and then through the first section 140e of the passage disposed in the fragment 154. The free ends of the suture would then be inserted through the second anchor 52e. The suture 38e would be tensioned to pull the bone fragment 154 into place with the side surface 28e in aligned engagement with the surface 30e on the main bone 20e. The knot 78e would then be tied while maintaining the desired tension in the suture 38e.

It should be understood that the anchor 52e and knot 78e could be positioned adjacent to the bone fragment 154 and the anchor 50e positioned adjacent to the bone 20e. Although only a single bone suture assembly 32e has been illustrated in FIG. 8, multiple bone suture assemblies could be used to position the bone fragment 154 relative to the bone 20e.

In the embodiment of the invention illustrated in FIGS. 7 and 8, the bone suture assembly 32e includes a pair of anchors 50e and 52e. If desired, a suture retainer could be substituted for either or both of the anchors 50e and 52e. Thus, a suture retainer having a construction similar to the construction of the suture retainer 92 of FIG. 3 could be used in place of the second anchor 52e. It should be understood that the suture retainer 92 could have the same construction as any one of the suture retainers disclosed in the aforementioned U.S. patent application Ser. No. 08/905,084 filed Aug. 1, 1997 by Peter M. Bonutti et al. and entitled "Method and Apparatus for Securing a Suture".

In the embodiment of the invention illustrated in FIG. 8, the anchors 50e and 52e are placed in engagement with the bone of fragment 154 and main bone 20e. However, it is contemplated that the anchor 50e and/or 52e could be positioned in engagement with body tissue other than bone. For example, the anchor 50e could be positioned in engagement with a portion of the fibrous body tissue 158 to position the fibrous body tissue 158 relative to the bone fragment 154 and to more securely interconnect the fibrous body tissue and the bone fragment. If desired, body tissue could be positioned between the anchor 52e and the main bone 20e.

In FIG. 8, there is a single bone fragment 154. However, fractures may occur in such a manner as to have a plurality of bone fragments. A plurality of bone suture assemblies 32e could be utilized to interconnect the plurality of bone fragments and the main bone.

When a fracture occurs in such a manner as to form a plurality of bone fragments, it may be desired to use bone suture assemblies 32e in association with only the larger bone fragments. If desired, a bridge or cover member could extend across the bone fragments to position the bone fragments relative to each other. One or more bone suture assemblies 32e would extend through one or more of the larger bone fragments and through the bridge or cover member. Force applied against the bridge or cover member by an anchor or anchors in a bone suture assembly or assemblies 32e would urge the bridge or cover member toward the main bone 20e to position the smaller bone fragments relative to the larger bone fragments and main bone 20e and to press the bone fragments against each other and against the main bone.

One or more of the anchors 50e and 52e could be formed of body tissue or of material which absorbs body fluid and expands. Alternatively, one or more of the anchors 50e or 52e could be mechanically expanded to block movement into the passage 50e.

Bone Fragment Retention

In the embodiment of the invention illustrated in FIG. 2, the bone suture assembly 32 extends between diametrically opposite outer side surface areas on the bone 20. This results in the first suture anchor 50 being disposed against an outer side surface of the hard outer layer 42 of the bone 20 (FIG. 1) and the suture anchor 52 being disposed against the outer side surface of the hard outer layer 42 on the opposite side of the bone. In the embodiment of the invention illustrated in FIG. 9, one of the anchors is disposed within the bone and the other anchor is disposed outside of the bone. Since the embodiment of the invention illustrated in FIG. 9 is generally similar to the embodiment of the invention illustrated in FIGS. 2-8, similar numerals will be utilized to identify similar components, the suffix letter "f" being associated with the numerals of FIG. 9 in order to avoid confusion.

A bone 20f has a hard outer layer 42f which encloses spongy cancellous bone tissue 44f. A fragment 164 has broken away from the hard outer layer 42f. A bone suture assembly 32f is used to position and hold the fragment 164 in engagement with the bone 20f. The bone suture assembly 32f includes a first suture anchor 50f which is disposed in engagement with an inner side surface 166 of the outer layer 42f of bone. A second anchor 50f is disposed in engagement with an outer side surface 168 of the fragment 164. A suture 38f extends between the first and second anchors 50 and 52f. The suture 38f extends through a passage 40f which extends across a fracture 26f.

When the bone suture assembly 32f is used to position the fragment 164 against the outer layer 42f of the bone 20f, the fragment 164 is aligned with the outer layer 42f of the bone 20f. At this time, a side surface 172 on the fragment 164 is disposed in aligned engagement with a side surface 174 on the bone 20f. The two side surfaces 172 and 174 were formed by breaking away of the fragment 164 from the outer layer 42f of the bone.

Once the fragment 164 has been aligned with the bone 20f, the linear passage 40f is formed by drilling or other methods through the fragment 164 and the outer layer 42f of bone. A cylindrical tubular member (not shown) having a thin cylindrical side wall is then inserted through the passage 40f. The first anchor 50*f* is moved to an orientation in which a longitudinal central axis of the first anchor is aligned with a longitudinal central axis of the cylindrical tubular member.

The first anchor 50*f* is then moved through the cylindrical tubular member, across the fracture 26*f* and into the spongy cancellous bone tissue 44. A pusher member applies force against a trailing end of a first anchor 50*f* to push the anchor through the tubular member. When the leading end of the first anchor 50*f* emerges from the passage 40*f*, the longitudinal central axis of the first anchor is aligned with the longitudinal central axis of the passage 40*f*.

The first anchor 50*f* is then pivoted through 90 degrees to change its orientation to the orientation shown in FIG. 9. The tubular member is then withdrawn from the passage 40*f*. The free ends of the suture 38*f* are then inserted through openings in the anchor 52*f*. The suture is tensioned to press the anchor 50*f* against the inner side surface 166 on the outer layer 42*f* of the bone 20*f*. The second anchor 52*f* is pressed against the outer side surface 168 or the fragment 164 with a predetermined force by the tension in the suture 38*f*. A knot 78*f* is then tied in the free ends of the suture 38*f* to maintain the desired tension in the suture.

Although it is believed that it may be desired to remove the tubular member from the passage 40*f*, the tubular member could be left in the passage if desired. If the tubular member is to be left in the passage 40*f*, the tubular member may be formed of a biodegradable or bioerodible copolymer. Of course, the use of the tubular member could be eliminated if desired.

It should be understood that a suture retainer, having a construction similar to the construction of the suture retainer 92 of FIG. 3, could be used in place of the second anchor 52*f* if desired. Although the suture anchor 52*f* has been shown in FIG. 9 as being disposed in direct abutting engagement with the outer side surface 168 of the bone fragment 164, a layer of body tissue could be provided between the suture anchor 52*f* and the outer side surface 168 of the bone fragment 164 to hold the body tissue against movement relative to the bone 20*f*. If desired, a plurality of bone suture assemblies 32*f* could be utilized to hold the bone fragment 164.

Use of Plates with Bone Suture Assembly

In the embodiment of the invention illustrated in FIG. 2, the suture anchors 50 and 52 are disposed in abutting engagement with an outer side surface of a bone. In the embodiment of the invention illustrated in FIG. 10, a pair of bone plates and rigid fasteners are used in association with a bone suture assembly. Since the embodiment of the invention illustrated in FIG. 10 is generally similar to the embodiment of the invention illustrated in FIGS. 2-9, similar numerals will be utilized to designated similar components, the suffix "g" being associated with the numerals of FIG. 10 to avoid confusion.

A bone 20*g* has sections 22*g* and 24*g* which are separated by a fracture 26*g*. In accordance with a feature of this embodiment of the invention, a pair of plate members 184 and 186 are used in association with a bone suture assembly 32*g*. The plate members 184 and 186 may be formed of any desired biocompatible material. Thus, the plate members may be formed of metal or a polymeric material. If the plate members 184 and 186 are formed of polymeric material, biodegradable or bioerodible copolymers could be utilized.

In the illustrated embodiment of the invention, the plate members 184 and 186 are rigid and are shaped to engage the bone 20*g*. If desired, the plate members 184 and 186 could have sufficient flexibility to enable the plate members to be plastically deformed to the configuration of the bone 20*g* after having been positioned in engagement with the bone.

A first suture anchor 50*g* is pressed against the plate member 184 by tension in a suture 38*g*. The suture 38*g* extends through a passage 40*g* in the bone 20*g*. A second anchor 52*g* is pressed against the plate member 186 by the tension in the suture 38*g*. A knot 78*g* is provided in the suture 38*g*.

A pair of screws 190 and 192 extend diametrically through the bone 20*g* between the plate members 184 and 186. The screws 190 and 192 are engaged by nuts 196 and 198 which engage the plate member 184. The screws 190 and 192 and nuts 196 and 198 cooperate to press the plate members 184 and 186 against the bone 20*g*. If desired, bone suture assemblies having the same construction as the bone suture assembly 32*g* could be substituted for the screws 190 and 192 and nuts 196 and 198 so that the plates 184 and 186 would be held in position against the bone 20*g* by only the plurality of bone suture assemblies 32*g*.

The screws 190 and 192 and nuts 196 and 198 may be formed of any desired biocompatible material. Thus, the screws 190 and 192 and nuts 196 and 198 may be formed of metal or a polymeric material. If the screws 190 and 192 and nuts 196 and 198 are formed of polymeric material, biodegradable or bioerodible copolymers could be utilized.

In the illustrated embodiment of the invention, the screws 190 and 192 extend through the bone 20*g*. It is contemplated that shorter screws could be utilized if desired. These shorter screws would have relatively coarse bone engaging thread convolutions to hold the short screws and plate members 184 and 186 in place. The shorter screws would have a length which is less than diameter of the bone 20*g*.

In the illustrated embodiment of the invention, the bone suture assembly 32*g* extends through a linear passage 40*g*. If desired, the passage 40*g* could have a nonlinear configuration. If bone suture assemblies 32*g* are substituted for the screws 190 and 192 and nuts 196 and 198, some of the bone suture assemblies could extend through linear passages while other bone suture assemblies extend through nonlinear passages.

Installation Method

In the embodiment of the invention illustrated in FIG. 2, the passage 40 is formed in the bone 20 by any desired method. A thin walled cylindrical tubular member is then inserted into the passage and the first suture anchor 50 moved through the thin walled member. In the embodiment of the invention illustrated in FIGS. 11 and 12, a cannulated drill is used to drill a passage through a bone and to guide movement of the first anchor through the bone. Since the embodiment of the invention illustrated in FIGS. 11 and 12 is generally similar to the embodiments of the invention illustrated in FIGS. 2-10, similar numerals will be utilized to identify similar components, the suffix "h" being associated with the numerals in FIGS. 11 and 12 to avoid confusion.

A bone 20*h* has a fracture (not shown). When the fracture is to be treated with a bone suture assembly 32*h* (FIG. 12), a thin elongated cylindrical member or K-wire 204 is first inserted through the bone 20*h*. This may be done by rotating the thin elongated member 204 with a drill drive mechanism in the manner indicated by an arrow 206 in FIG. 11. The drill drive mechanism is provided with a passage which extends through a drive shaft for the mechanism. While the thin elongated member 204 is being rotated by the drill drive mechanism, the K-wire extends through the passage in the drill drive mechanism.

As the thin elongated member 204 is rotated by the drill drive mechanism, it is pressed against the bone 20*h*. As the thin elongated member 204 is rotated, in the manner indicated by the arrow 206 in FIG. 11, the thin elongated member is moved diametrically through the generally cylindrical bone 20h until the leading end of the thin elongated member 204 extends from the opposite side of the bone. Thus, the thin elongated member 204 is moved through the hard outer layer 42h (FIG. 12) at one side of the bone 20h, through the spongy or cancellous bone tissue 44h, and through the hard outer layer at the diametrically opposite side of the bone. When this has been done, the thin elongated member 204 will extend across the fracture in the bone.

The drill drive mechanism is then disengaged from the thin elongated member 204. A cannulated drill 210 is moved axially along the thin elongated member until the leading end portion 212 of the drill 210 engages the bone 20h (FIG. 11). The drill 210 is then gripped by the drill drive mechanism.

While the thin elongated member 204 remains stationary, the drill 210 is rotated about the thin elongated member in the manner indicated by an arrow 214 in FIG. 11. As the drill 210 is rotated about the stationary thin elongated member 204, the drill is moved axially into the bone 20h. As this occurs, the leading end 212 of the drill enlarges the hole or passage formed in the bone 20h by the thin elongated member 204. The drill 210 is moved along the thin elongated member 204 until the drill extends diametrically across the bone 20h. This movement of the drill 210 is guided by engagement of the thin elongated member 204 with a side wall of a cylindrical passage 218 which extends axially through the drill 210. Movement of the drill 210 through the bone 20h forms a passage 40h which extends through a fracture in the bone.

Once the drill 210 has been moved diametrically through the generally cylindrical bone 20h (FIG. 12), the thin elongated member 204 is withdrawn from the drill. This leaves an open cylindrical passage 218 extending through the drill 210 and across the bone 20h. The passage 218 has a diameter which is just slightly greater than the diameter of a cylindrical first anchor 50h of the bone suture assembly 32h. The cylindrical first anchor 50h is axially aligned with the passage 218 in the drill 210, in the manner shown in FIG. 12. At this time, the suture 38h has been inserted through openings in the first anchor 50h and suture limbs or sections 72h and 74h extend away from the first anchor 50h, in the manner indicated schematically in FIG. 12.

A cylindrical pusher member 222 is axially aligned with the first anchor 50h and the passage 218 through the drill 210. The pusher member 222 is utilized to push the first anchor 50h through the drill 210 to the far side of the bone 20h.

As the first suture anchor 50h emerges from the passage 28 in the drill 210, the anchor is pivoted through ninety degrees. This pivotal movement changes the orientation of the anchor 50h from an orientation in which the longitudinal central axis of the anchor 50h is aligned with the longitudinal central axis of the passage 218 and drill 210 to an orientation in which a longitudinal central axis of the cylindrical anchor 50h extends perpendicular to the longitudinal central axis of the passage and drill. The manner in which the anchor 50h is pivoted is the same as is described in the aforementioned U.S. Pat. Nos. 5,527,343 and 5,534,012.

The pusher member 222 is then withdrawn from the drill 10 and the drill is withdrawn from the passage formed through the bone 20h. As this occurs, the suture 38h is tensioned to hold the anchor 50h in place against the bone 20h. The drill 210 is then disengaged from the suture 38h. The free limbs 72 and 74 of the suture 38h are then inserted through a second anchor corresponding to the anchor 52 in FIG. 2. While a predetermined tension is maintained in the suture 38h, the suture is tied to hold the second suture anchor, corresponding to the suture anchor 52 in FIG. 2, against the bone 20h on a side of the bone opposite from the anchor 50h.

In the foregoing description, the drill 210 has been a rigid drill which has been used to form a linear passage to the bone 20h. However, it is contemplated that a flexible drill could be utilized to drill a passage through the bone. If this was done, the drill could be guided in such a manner as to form a nonlinear passage in the bone.

The foregoing description of how the passage 40h is formed has been in conjunction with a bone 20h having a fracture similar to the fracture 26 of FIG. 2. However, it is contemplated that the thin elongated member 204 and drill 210 could be used to form a passage in a bone which has not been fractured (FIG. 4). The thin elongated member 204 and 210 could be used to form a passage which extends only part way through a bone (FIG. 9).

In the description of the embodiments of the invention illustrated in FIGS. 1-12, the suture 38 (FIG. 2) has a pair of limbs or sections 72 and 74. It is contemplated that the suture 38 could have only a single limb which would be connected at one end with the first anchor 50 and at the opposite end with the second anchor 52. This single limb could either be tied off at the second anchor 52 or gripped by a suture retainer, similar to the suture retainer 92 of FIG. 3.

In the embodiments of the invention illustrated in FIGS. 1-12, the suture 38 has been formed separately from the first suture anchor 50. It is contemplated that the first suture anchor 50 could be formed as one piece with the suture 38. For example, the suture and anchor could be formed as one piece in a manner similar to that disclosed in U.S. Pat. No. 4,669,473 or in U.S. Pat. No. 4,741,330.

The anchors 50 and 52 in the embodiment of FIGS. 2-12 could have any one of many different constructions. For example, the anchors could expand by absorbing body fluid. The anchor 50, which is moved through a passage 40 in the embodiments of FIGS. 2-12, could mechanically expand upon exiting from the passage.

Positioning of Tubular Member

Figure 13:
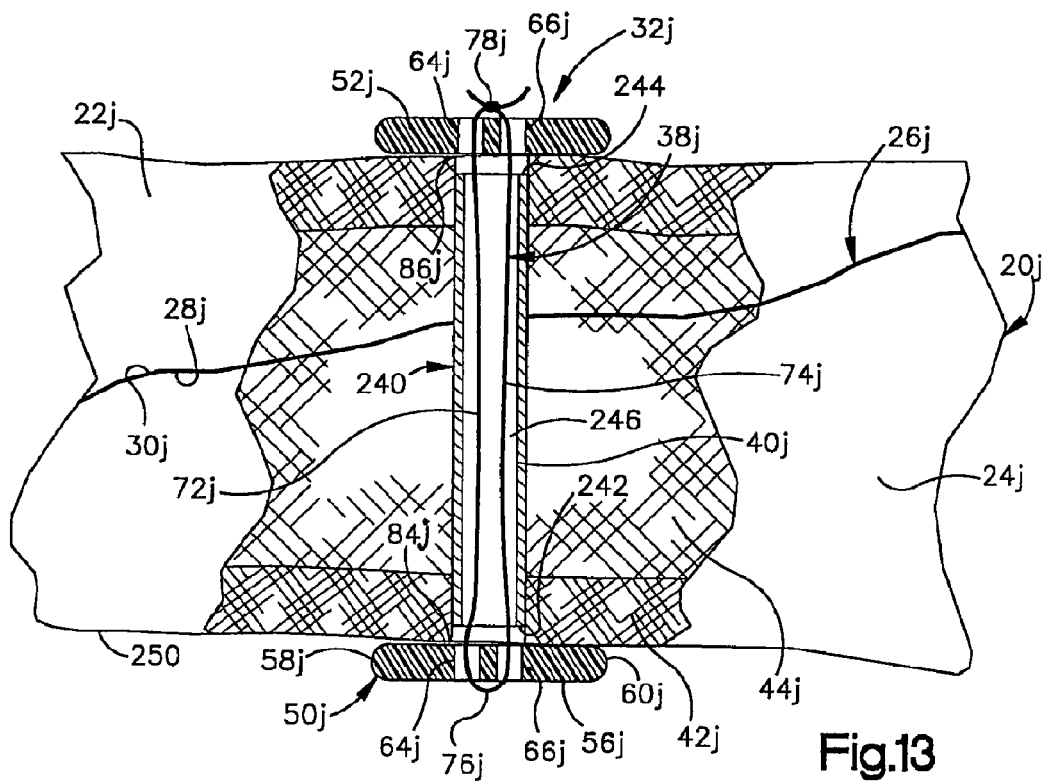
FIG. 13 is a schematic illustration, generally similar to FIG. 2, illustrating the manner in which a tubular member is positioned in a passage in the bone.

In the embodiment of the invention illustrated in FIG. 13, a tubular member is positioned in the passage which extends through the bone. Since the embodiment of the invention illustrated in FIG. 13 is generally similar to the embodiments of the invention illustrated in FIGS. 1-12, similar numerals will be utilized to designate similar components, the suffix letter "j" being associated with the numerals of FIG. 13 to avoid confusion.

A bone 20j which has been fractured is illustrated in FIG. 1. The bone 20j is divided into two sections 22j and 24j by a fracture 26j. Opposite side surfaces 28j and 30j of the fracture 26j are pressed together by bone securing assemblies 32j.

It should be understood that the bone securing assemblies 32j may be utilized in the treatment of any one of many different types of fractures. The fractures may or may not result in the formation of one or more bone fragments. In FIG. 13, the bone securing assembly 32j has been illustrated as interconnecting sections 22j and 24j of a complete bone fracture of the spiral type. However, the bone securing assemblies 32j could be utilized to connect a fragment of a bone to the main portion of the bone from which the fragment was broken off.

The bone securing assembly 32j (FIG. 13) includes a force transmitting member 38j which extends across the fracture 26j. The force transmitting member 38j may be any one of many different types of force transmitting members. The force transmitting member 38j may be formed of human or animal body tissue. However, it is presently preferred to use a suture as the force transmitting member 38j. Therefore, the force transmitting member 38j will be referred to herein as a suture.

The suture 38j, that is, the force transmitting member, is disposed in a straight cylindrical passage 40j which extends diametrically across a generally cylindrical portion of the bone 20j. The passage 40j extends through hard compact tissue of an outer layer 42j of the bone and through spongy or cancellous bone tissue 44j which is enclosed by the hard outer layer. Although the passage 40j has a linear configuration, the passage could have a nonlinear configuration if desired.

The suture 38j extends between a first suture anchor 50j disposed on one side of the fracture 26j and a second suture anchor 52j disposed on the opposite side of the fracture. Tension is maintained in the suture 38j to press the suture anchors 50j and 52j against opposite sides of the bone 20l with a predetermined force. This force presses the side surfaces 28j and 30j of the fracture 26j firmly together to promote healing of the fracture. If desired, buttons or other force distributing members could be provided between the anchors 50j and 52j and the bone 20j. Body tissue could be disposed between the anchors 50j and 52j and the bone 20j.

The suture 38j and/or suture anchors 50j and 52j may be formed of any desired natural or artificial material. For example, the suture 38j may be formed of either a polymeric material or a metal. The suture 38j may be biodegradable. Any known suture material may be utilized to form the suture 38j.

The suture anchors 50j and 52j have the same construction. However, the anchor 50j could have a construction which is different than the construction of the anchor 52j. The anchor 50j has a cylindrical outer side surface 56j which extends between smooth rounded end portions 58l and 60j. A pair of parallel cylindrical openings 64j and 66j extend diametrically through the anchor 50j. The anchor 50j is free of sharp corners or projections to avoid cutting or abrading of body tissue disposed adjacent to the anchor.

The suture anchor 50j is made of a biocompatible material. Suitable materials include stainless steel or titanium, cobalt chrome and other biocompatible metals. Polymeric material may also be used, suitable polymeric materials includes polyethylene, polypropylene, and biodegradable material such as PLA and PGA. It is believed that it may be preferred to form the suture anchors 50j and 52j from biodegradable or bioerodible copolymers. If desired, the anchor 50j could be formed of body material or hydrophilic materials.

It is contemplated that the anchor 50j may have any desired configuration. For example, the anchor 50j could have any one of the configurations disclosed in U.S. Pat. No. 5,522,846 issued Jun. 4, 1996 and entitled "Suture Anchor". Alternatively, the suture anchor 50j could have the configuration disclosed in U.S. Pat. No. 5,534,012 issued Jul. 9, 1996 and entitled "Method and Apparatus for Anchoring a Suture".

The cross-sectional size of the anchor 50j may be such as to enable the anchor to be moved through the passage 40j. However, the anchor 50j could have a size and configuration which would prevent movement of the anchor 50j through the passage 40j. For example, the anchors 50j and 52j could have the same construction as the retainer 92 of FIG. 3.

The length of the anchor 50j is such as to enable it to span an opening at an end of the passage 40j and transmit force from the suture 38j to a substantial area on the outer layer 42j of the bone 20j. The length of the anchor 50j may be approximately three times the diameter of the anchor. It is believed that it will be preferred to form the anchor 50j in such a manner as to eliminate any sharp corners or projections.

In the illustrated embodiment of the invention, the anchor 50j has a cylindrical configuration. This particular anchor has an axial length of about two millimeters and a diameter of about one millimeter. The openings 64j and 66j have a diameter of about one-half millimeter.

It should be understood that the foregoing dimensions have been set forth herein for purposes of clarity of description and it is contemplated that the size of the anchor 50j may vary as a function of the size of the bone being treated. Thus, relatively small anchors may be used in association with treatment of small bones in a wrist, hand, foot or ankle of a patient. Relatively large anchors may be used in association with treatment of larger bones in an arm, shoulder, leg or hip of a patient. It should be understood that the bone securing assembly 32j may be used in conjunction with many different bones other than the specific bones previously mentioned.

Only a single anchor 50j or 52j has been shown at opposite ends of the passage 40j. It is contemplated that a plurality of anchors could be provided at each end of the passage 40j. For example, a pair of separate or interconnected anchors could be provided in a manner similar to that disclosed in the aforementioned U.S. Pat. No. 5,534,012.

In the embodiment of the invention illustrated in FIG. 13, the suture 38j has a pair of limbs or sections 72j and 74j which extend through the openings 64j and 66j in the suture anchors 50j and 52j. A connector section 76j interconnects the two limbs 72j and 74j of the suture 38j and engages a portion of the anchor 50j. A knot 78j is formed in the opposite ends of the limbs 72j and 74j to interconnect the two limbs of the suture 38j.

When the knot 78j is formed, a predetermined tension is present in the limbs 72j and 74j of the suture 38j. This results in the suture anchors 50j and 52j being pressed firmly against the bone 20j with a predetermined force. This predetermined force is maintained during and after tying of the knot 78j.

When the bone securing assembly 32j is to be used to treat the fracture 26j in the bone 20j, the two sections 22j and 24j of the bone are pressed together at the fracture 26j to align the side surfaces 28j and 30j of the fracture. A drill is then used to form the passage 40j which extends diametrically through the generally cylindrical bone 20j. Of course, the passage 40j could be formed by the use of a tool other than a drill. If desired, the passage 40j could have a noncircular cross-sectional configuration.

Once the passage 40j has been formed in the two sections 22j and 24j of the bone 20j, a tubular cylindrical member 240 is inserted into the passage 40j and extends diametrically through the bone 20j. The leading end 242 of the tubular cylindrical member 240 is aligned with a circular outlet 84j from the passage 40j. The opposite or trailing end 244 of the tubular member is aligned with a circular inlet 86j to the passage 40j. The tubular member 240 has a thin cylindrical wall which engages the sections 22j and 24j of the bone 20l. A cylindrical inner side surface of the tubular member 240 defines a cylindrical passage having a diameter which is only slightly less than the diameter of the passage 40j.

The leading end 242 of the tubular member 240 is disposed in the compact outer layer 42j of the bone 20j. Similarly, the trailing end 244 of the tubular member 240 is disposed in the compact outer layer 42j of the bone 20j. The tubular member 240 extends across the fracture 26j and stabilizes the two sections 22j and 24j of the bone 20j. Since the opposite end portions of the tubular member 240 are disposed in the compact outer layer 42j of the bone 20j, the tubular member is solidly supported and holds the two sections 22j and 24j of the bone 20j in alignment at the fracture 26j.

The opposite ends 242 and 244 of the tubular member 240 are axially spaced from a generally cylindrical outer side surface 250 on the bone 20j. This enables the anchors 50j and 52j to be pressed against the outer side surface 250 of the bone 20j. Therefore, tension forces in the suture 38j are transmitted through the anchors 50j and 52j to the bone 20j.

By inserting the tubular member 240 into the passage 40*j*, the portions of the passage disposed on opposite sides of the fracture 26*j* are maintained in alignment. The tubular member 240 may be flexible to enable the tubular member to be inserted into a nonlinear passage 40*j* through the bone 20*j*. The tubular member 240 may be formed of metal or a polymeric material. If the tubular member 240 is formed of a polymeric material, it may be preferred to form the tubular member from a biodegradable or bioerodible copolymer.

In accordance with one of the features of this embodiment of the invention, the tubular member 240 is formed of bone. By forming the tubular member 240 of bone, tissue growth into the tubular member is promoted. The tubular member 240 may be packed with bone or bone graft. The tubular member 240 may contain bone osteoinductive protein (BMP). Bone growth inducing materials containing apatite compositions with collagen and/or other materials may be utilized. The tubular member 240 may be formed of either human or animal bone.

It is contemplated that it may be preferred to form the tubular member 240 of freeze dried human bone obtained from a cadaver. The freeze dried bone will absorb body fluids. As this occurs, the tubular member 240 will expand and grip the two sections 22*j* and 24*j* of the bone 20*j*. The body fluids will be conducted into bone growth promoting materials contained in the tubular member 240. If desired, antibiotics and/or other medicants may be provided in the bone or bone graft with which the tubular member 240 is packed. Of course, the tubular member 240 may be formed of other materials, such as biodegradable materials, if desired.

The suture 38*j* is formed into a loop which extends through the openings 64*j* and 66*j* in the anchor 50*j*. At this time, the suture 38*j* has a length which is substantially greater than the length illustrated in FIG. 2. The cylindrical anchor 50*j*, with the suture 38*j* connected thereto, is then positioned in axial alignment with the tubular member 240 which extends through the passage 40*j*. Thus, the anchor 50*j* is moved to an orientation in which a longitudinal central axis of the anchor is coincident with the longitudinal central axis of the cylindrical passage 246 in the tubular member 240 which extends through the passage 40*j* in the bone 20*j*.

The leading end 58*j* of the anchor 50*j* is then moved into the cylindrical tubular member 240 which forms a liner for the passage 40*j*. A pusher member pushes the anchor 50*j* from an upper (as viewed in FIG. 13) end 244 of the tubular member 240 along the passage 246 in the tubular member 240 and the passage 40*j* in the bone 20 and through the outlet 84*j* from the passage. As the anchor 50*j* moves through the passages 40*j* and 246, the suture 38*j* is pulled through the passages by the anchor.

The orientation of the anchor 50*j* is then changed from an orientation in which the longitudinal central axis of the anchor 50*j* is aligned with the coincident longitudinal central axes of the passages 40*j* and 246 to an orientation in which the longitudinal central axis of the anchor 50*j* extends generally perpendicular to the longitudinal central axis of the passages 40*j* and 246, i.e., the orientation shown in FIG. 13. To pivot the anchor 50*j* to the orientation shown in FIG. 13, as the anchor emerges from the outlet 84, the suture 38*j* is tensioned. The combination of the tension in the suture 38*j* and force applied against the trailing end 60*j* of the anchor 50*j* by the pusher member causes the anchor to pivot about the trailing end 60*j* of the anchor. The pusher member is then withdrawn and the suture 38*j* tensioned to move the anchor to the position shown in FIG. 13 in a manner similar to that described in the aforementioned U.S. Pat. Nos. 5,527,343 and 5,534,012.

Although it is believed that it may be preferred to change the orientation of the anchor 50*j* after it has emerged from the passages 40*j* and 246, the anchor could be blocked from reentering the passage in other ways if desired. Thus, the anchor could expand after emerging from the passages 40*j* and 246. This could be accomplished by having spring biased arms held in a retracted position by engagement of spring biased arms with the inner side surface of the tubular cylindrical member 240 which lines the passage 40*j*. Upon emerging from the passages 40*j* and 246, the arms would move outward under the influence of spring forces and extend radially outward beyond the edge of the exit from the passage 40*j*. If desired, the anchor 50*j* could be constructed so as to expand in a manner similar to that disclosed in U.S. Pat. No. 5,397,331 and/or U.S. Pat. No. 4,409,974.

Rather than expanding under the influence of stored energy, such as spring force, the anchor 50*j* could expand by absorbing body fluids. Thus, the anchor 50*j* may be compressed when it moves through the passages 40*j* and 246 and will expand and absorb body fluids after emerging from the passages 40*j* and 246. It is contemplated that the anchor 50*j* could be constructed so as to expand in any one of the ways disclosed in U.S. patent application Ser. No. 08/699,553 filed Aug. 19, 1996 by Peter M. Bonutti and entitled "Suture Anchor".

Once the anchor 50*j* has been moved through the passage 246, the passage is packed with bone particles and/or bone graft. The bone particles and/or bone graft contains bone growth inducing materials. In addition, the bone particles and/or bone graft may contain medicinal substances along with osteoinductive protein.

The limbs 72*j* and 74*j* of the suture 38*j* are then threaded through openings 64*j* and 66*j* in the second suture anchor 52*j*. The limbs 72*j* and 74*j* of the suture 38*j* are tensioned and the second anchor 52*j* is pressed against the outer side surface 250 of the bone 20*j*. While a predetermined tension force is maintained in the limbs 72*j* and 74*j* of the suture 38*j*, the knot 78*j* is tied in the suture to interconnect the two suture anchors 50*j* and 52*j* with the suture 38*j*. The suture 38*j* is then trimmed to the desired length.

Once the knot 78*j* has been tied between the limbs 72*j* and 74*j* of the suture 38*j*, the tension in the suture 38*j* presses the side surfaces 28*j* and 30 of the fracture 26*j* together. This pressure between the side surfaces 28 and 30*j* of the fracture 26*j* is maintained by the suture 38 and suture anchors 50*j* and 52*j* until the fracture heals. It is believed that it may be preferred to form the suture 38*j* and suture anchors 50*j* and 52*j* of a biodegradable material which, after the fracture 26*j* has healed, will dissolve in the patient's body.

The cylindrical tubular member 240 which is inserted into the passage 40*j* through the bone 20*j* performs the dual functions of lining the inside of the passage 40*j* and maintaining the two sections 22*j* and 24*j* of the bone in alignment. The cylindrical tubular member 240 could have a slot formed in a side wall of the tubular member to facilitate insertion of the tubular member into the passage 40*j*. It is contemplated that the cylindrical tubular member 240 could be left in the passage 40*j* after the bone securing assembly 32*j* has been installed. If the slotted or unslotted cylindrical tubular member 240 is to be left in the passage 40*j*, the cylindrical tubular member 240 may be formed of a biodegradable or bioerodible copolymer. When the cylindrical tubular member remains in the passage 40*j*, the suture 38*j* extends through the tubular member.

Although only a knot 78*j* has been shown in FIG. 13 adjacent to the second anchor 52*j*, a suture retainer could be provided to further hold the limbs 72*j* and 74*j* of the suture

38j. If a suture retainer is to be used in association with the knot 78j, the suture retainer will be moved along the limbs of the suture 38j toward the knot before the limbs 72j and 74j of the suture are trimmed to the short length shown in FIG. 13. The suture retainer would then be plastically deformed to grip the limbs 72j and 74j of the suture 38j. Thereafter, the suture limbs 72j and 74j would be trimmed to a desired length.

Although it is preferred to use a suture as the force transmitting member 38j, it should be understood that the anchors 50j and 52j could be interconnected by other force transmitting members, such as a rod formed of bone. Although the anchors 50j and 52j have constructions which enable them to be used with a suture, the anchors could be constructed so as to be used with other types of force transmitting members. For example, the anchors 50j and 52j could have thread convolutions to engage thread convolutions on a force transmitting member formed by a rod.

In the embodiment of the invention illustrated in FIG. 13, the member 240 is tubular. However, it is contemplated that a solid member could be used to transmit force to bone on opposite sides of the fracture 26j. Thus, the member 240 could be a solid cylindrical member formed of bone. The cylindrical member may be formed of freeze dried bone.

When the member 240 is a solid member, the suture or other force transmitting member 38j is eliminated. The solid member formed of bone becomes the force transmitting member. Anchors, corresponding to the anchors 50j and 52j, are connected to opposite ends of the solid member 240 formed of bone. The anchors may have internal thread convolutions which engage external thread convolutions on the solid member 240 formed of bone. Of course, other known connectors could be utilized to connect anchors with opposite ends of the solid member 240 formed of bone.

Nonlinear Suture Passage—Tubular Member

Figure 14:
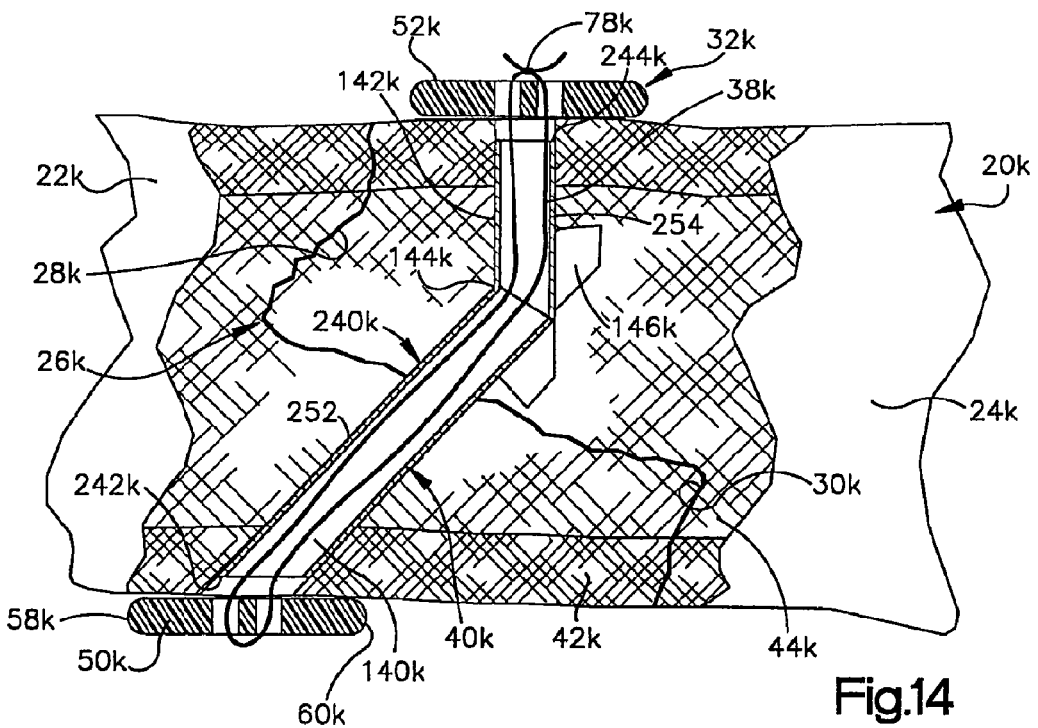
FIG. 14 is a schematic illustration, generally similar to FIG. 5, illustrating the manner in which tubular members are positioned in a nonlinear passage in a bone.

In the embodiment of the invention illustrated in FIG. 13, the passage 40j through which the suture 38j extends has a linear configuration. In the embodiment of the invention illustrated in FIG. 14, the passage through which the suture extends has a nonlinear configuration. Since the embodiment of the invention illustrated in FIG. 14 is generally similar to the embodiment of the invention illustrated in FIGS. 1-13, similar numerals will be utilized to identify similar components, the suffix letter "k" being associated with the components of the embodiment of the invention illustrated in FIG. 14 to avoid confusion.

A bone 20k as a fracture 26k which divides the bone into two sections 22k and 24k. Opposite side surfaces 28k and 30k of the fracture 26k are pressed together by a bone suture assembly 32k. The bone suture assembly 32k includes a suture 38k which extends between first and second suture anchors 50k and 52k.

The suture 38k is disposed in a passage 40k having a nonlinear configuration. Thus, the passage 40k includes a first section 140k which is skewed relative to a second section 142k of the passage 40k. A bend 144k is formed in the passage 40k at an intersection 146k of the first and second sections 140k and 142k of the passage 40k. The flexible suture 38k extends around the bend 144k along a nonlinear path between the suture anchors 50k and 52k. At the bend 144k, the suture 38k applies force against the section 24k of the bone 20k urging the section 24k toward the left (as viewed in FIG. 5). This force presses the sections 22k and 24k of the bone 20k firmly together at the fracture 26k.

The suture anchors 50k and 52k have the same cylindrical construction as the suture anchors 50, 52, 50j and 52j in the embodiment of the invention illustrated in FIGS. 2 and 13. A knot 78k (FIG. 14) is provided between limbs of the suture 38k to maintain a desired tension in the suture 38k. This tension pulls the suture anchors 50k and 52k toward each other. In addition, this tension presses the section 24k of the bone 20k firmly against the section 22k of the bone at the fracture 26k.

The first section 140k of the passage 40k is formed at an angle to and extends through a longitudinal central axis of the generally cylindrical bone 20k. The second section 142k of the passage 40k is formed in a direction perpendicular, i.e., along a radius, of the generally cylindrical bone 20k. The two sections 140k and 142k of the passage 40k terminate in the spongy cancellous bone tissue 44k.

When the suture assembly 32k is to be used to treat the fracture 26k in the bone 20k, the two sections 22k and 24k of the bone are pressed together at the fracture 26k to align the side surfaces 28k and 30k of the fracture. A drill or other hole forming apparatus is then used to form the first section 140k of the passage 40k. The drill or other hole forming apparatus is then used to form the second section 142k of the passage 40k. When the second section 142k of the passage 40k intersects the first section 140k of the passage 40k, formation of the section 142k of the passage 40k is interrupted.

Once the nonlinear passage 40k has been formed in the two sections 22k and 24k of the bone 20k, a tubular cylindrical liner 240k is inserted into the passage 40k. The tubular cylindrical liner 240k is formed by two separate cylindrical tubular members 252 and 254 which are inserted at opposite ends of the passage 40k. Alternatively, the tubular cylindrical liner 240k may be formed by a single flexible tubular member which is inserted into the section 140k of the passage 40k and then moved around the bend 144k into the section 142k of the passage 40k.

It is believed that it may be preferred to form the tubular members 252 and 254 of bone. The bone forming the tubular members 252 and 254 may be either human or animal bone. The tubular members 252 and 254 may be formed of freeze dried human bone.

The leading end 242k of the tubular member 252 is disposed in the compact outer layer 42k of the bone 20k. Similarly, the trailing end 244k of the tubular member 254 is disposed in the compact outer layer 42k of the bone 20k. The tubular member 252 extends across the fracture 26k and stabilizes the two sections 22k and 24k of the bone 20k. Since the end portions 242k and 244k of the tubular members 252 and 254 are disposed in the compact outer layer 42k of the bone 20k, the tubular members are solidly supported and hold the two sections 22k and 24k of the bone 20k in alignment at the fracture 26k.

The opposite ends 242k and 244k of the tubular members 252 and 254 are axially spaced from a generally cylindrical outer side surface 250k on the bone 20k. This enables the anchors 50k and 52k to be pressed against the outer side surface 250k of the bone 20k. Therefore, tension forces in the suture 38k are transmitted through the anchors 50k and 52k to the bone 20k.

The cylindrical anchor 50k, with the suture 38k connected thereto, is then positioned in axial alignment with the section 142k of the passage 40k. The leading end 58k of the anchor 50k is then moved into the section 142k of the passage 40k lined by the tubular member 254. A flexible pusher member applies force against the trailing end 60k of the anchor 50k and pushes the anchor around the bend 144k and through the section 140k of the passage 40k lined by the tubular member 252.

Alternatively, a flexible wire or other member could be inserted into the section 140k of the passage 40k. The wire would move around the bend 144k and extend outward from the section 142*k* of the passage. The wire would then be connected with the anchor 50*k* and suture 38*k*. The leading end 58*k* of the anchor 50*k* would then be inserted into the section 142*k* of the passage 40*k*. Tension on the wire would pull the anchor 50*k* around the bend 144*k* and out of the section 140*k* of the passage 40*k*.

The passages in the tubular members 252 and 254 may be packed with bone particles and/or bone graft. Bone osteoinductive protein (BMP) may be provided in the tubular members. Antibiotics and/or other medicants may be included along with collagen.

The suture 38*k* is then threaded through openings in the suture anchor 52*k*. The suture 38*k* is then tensioned and the second anchor 52*k* is pressed against the outer side surface of the bone 20*k*. While a predetermined tension force is maintained in the suture 38*k*, the knot 78*k* is tied.

In the illustrated embodiment of the invention, the two sections 140*k* and 142*k* of the passage 40*k* have a straight cylindrical configuration. However, it is contemplated that the sections 140*k* and 142*k* of the passage 40*k* could have a different configuration if desired. For example, the section 140*k* and/or 142*k* of the passage 40*k* could have a nonlinear central axis and could have a noncircular cross-sectional configuration if desired.

Body tissue, corresponding to the body tissue 132 of FIG. 4 could be disposed between the anchor 50*k* and/or 52*k* and the bone 20*k*. Although the suture 38*k* has been illustrated as having a pair of limbs or sections which extend between the anchors 50*k* and 52*k*, the suture 38*k* could have a single limb or section if desired. The anchor 50*c* could mechanically expand, by absorbing body liquid or under the influence of expansion springs, after the anchor has emerged from the passage 40*k* to prevent the anchor from being pulled back through the passage.

Retainer and Tubular Member

Figure 15:
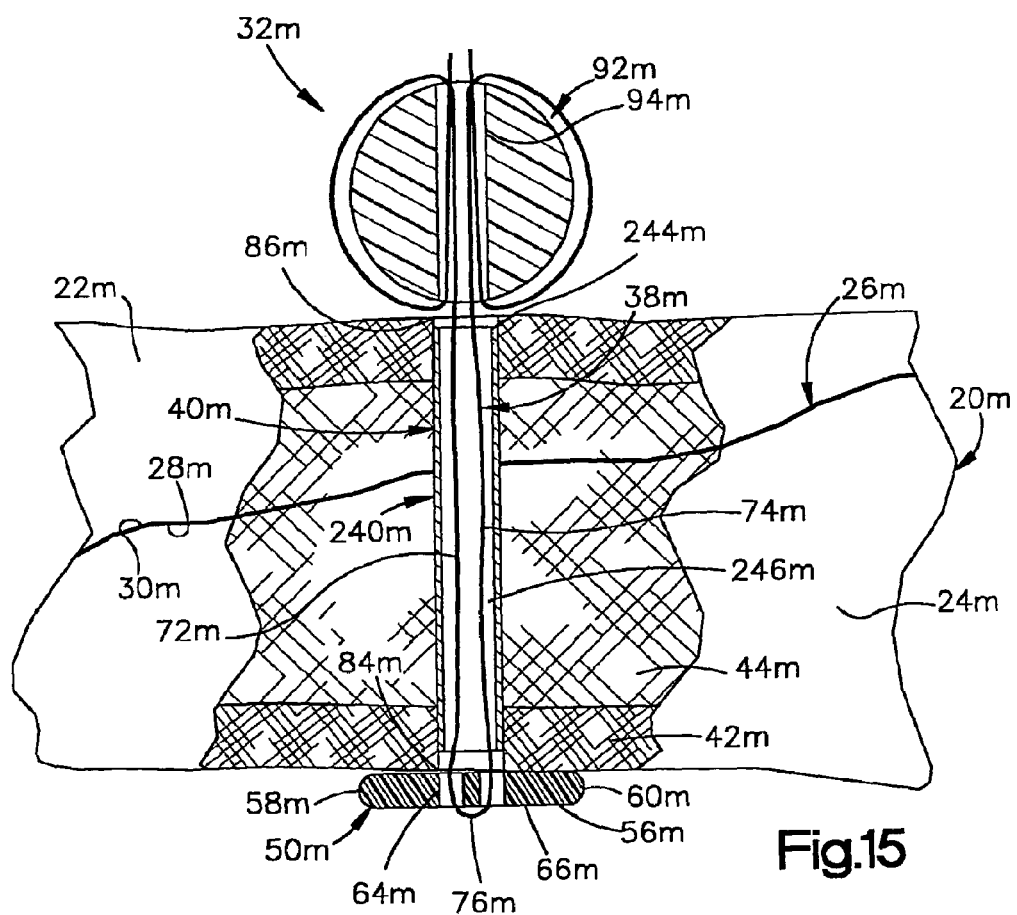
FIG. 15 is a schematic illustration, generally similar to FIG. 3, illustrating the manner in which a suture retainer is used with a tubular member which is positioned in a passage in a bone.

In the embodiment of the invention illustrated in FIG. 13, a pair of suture anchors 50*j* and 52*j* are connected with the suture 38*j* to maintain tension in the suture and pressure against opposite side surfaces 28*j* and 30*j* of the fracture 26*j*. In the embodiment of the invention illustrated in FIG. 15, a suture retainer is used in place of one of the suture anchors. Since the embodiment of the invention illustrated in FIG. 15 is generally similar to the embodiment of the invention illustrated in FIG. 13, similar numerals will be utilized to designate similar components, the suffix letter "m" being associated with the embodiment of the invention illustrated in FIG. 15 to avoid confusion.

A bone 20*m* has sections 22*m* and 24*m* which are separated by a fracture 26*m*. The fracture 26*m* has side surfaces 28*m* and 30*m* which are pressed together by a bone suture assembly 32*m*. A suture 38*m* extends through a cylindrical passage 40*m* which extends diametrically through the generally cylindrical bone 20*m*. The suture 38*m* has a pair of limbs or sections 72*m* and 74*m* which are connected with a suture anchor 50*m*. The suture anchor 50*m* has the same construction as the suture anchor 50 of FIG. 2.

Once the passage 40 has been formed in the two tubular sections 22*m* and 24*m* of the bone 20*m*, a tubular cylindrical member 240*m* is installed into the passage 40*m* and extends diametrically through the bone 20*m*. The leading end 242*m* of the cylindrical member 240*m* is aligned with a circular outlet 84*m* from the passage 40*m*. The opposite or trailing end 244*m* of the tubular member 240*m* is aligned with a circular inlet 86*m* to the passage 40*m*.

The tubular member 240*m* has a thin cylindrical wall which engages the sections 22*m* and 24*m* of the bone 20*m*. A cylindrical inner side surface of the tubular member 240*m* defines a cylindrical passage 246*m* having a diameter which is only slightly less than the diameter of the passage 40*m*. The tubular member 240*m* is formed of bone. Alternatively, the tubular member 240*m* could be formed of a biodegradable material.

The leading end 242*m* of the tubular member 240*m* is disposed in the compact outer layer 42*m* of the bone 20*m*. Similarly, the trailing end 244*m* of the tubular member 240*m* is disposed in the compact outer layer 42*m* of the bone 20*m*. The tubular member 240*m* extends across the fracture 26*m* and stabilizes the two sections 22*m* and 24*m* of the bone 20*m*. Since the opposite end portions of the tubular member 240*m* are disposed in the compact outer layer 42*m* of the bone 20*m*, the tubular member is solidly supported and holds the two sections 22*m* and 24*m* of the bone 20*m* in alignment at the fracture 26*m*.

The opposite ends 242*m* and 244*m* of the tubular member 240*m* are axially spaced from a generally cylindrical outer side surface 250*m* on the bone 20*m*. This enables the anchors 50*m* and 92*m* to be pressed against the outer side surface 250*m* of the bone 20*m*. Therefore, tension forces in the suture 38*m* are transmitted through the anchors 50*m* and 92*m* to the bone 20*m*.

The tubular member 240*m* is formed of freeze dried human bone. The tubular member 240*m* is packed with bone and/or bone graft. The tubular member 240*m* also contains bone osteoinductive protein (BMP). Suitable medicants may be provided in the tubular member 240*m*.

A suture retainer 92*m* is used in place of the suture anchor 52 of FIG. 2. The suture retainer 92*m* (FIG. 15) has a spherical configuration. A cylindrical passage 94*m* extends through the center of the spherical suture retainer 92*m*. The sections 72*m* and 74*m* of the suture 38*m* extend around the spherical outer side surface of the suture retainer 92*m*. Thus, a loop is formed in each of the sections 72*m* and 74*m* around portions of the suture retainer 92*m*.

If desired, the suture retainer 92*m* could have a different configuration. For example, the suture retainer 92*m* could have an oval or elliptical configuration. Although the passage 94*m* has a linear central axis, the passage could have a nonlinear central axis. If desired, a plurality of passages having the same or different configurations could be provided in the suture retainer 92*m*.

After the suture 38*m* has been inserted through the suture retainer 92*m*, the suture retainer 92*m* is moved along the sections 72*m* and 74*m* of the suture 38*m* toward the bone 20*m*. The suture retainer 92*m* is formed as one piece of a polymeric material having a relatively low coefficient friction. Therefore, the two sections 72*m* and 74*m* of the suture 30*m* can readily slide along the surfaces of the suture retainer 52*m* while the suture retainer moves toward the bone 20*m*.

A predetermined tension is maintained in the sections 72*m* and 74*m* of the suture 38*m* while the suture retainer 92*m* is pressed against the bone 20*m*. This results in the suture 38*m* being pulled tightly against the suture anchor 50*m*. The tension in the suture 38*m* is effective to press the suture anchor 50*m* and retainer 92*m* against opposite sides of the bone 20*m* with a predetermined force.

While the sections 72*m* and 74*m* of the suture 38*m* are being tensioned with a predetermined force, the suture retainer 92*m* is plastically deformed in the same manner as previously described in conjunction with the embodiment of the invention illustrated in FIG. 3. To plastically deform the suture retainer 92*m*, a plurality of force applying or clamp members are pressed against the suture retainer with a predetermined minimum force. The force applied against the suture retainer 92*m* by the force applying members is sufficient to cause plastic deformation of the material of the suture retainer.

The force is applied against the suture retainer 92*m* while the suture retainer is at a temperature which is below the transition temperature of the biodegradable polymer which forms the suture retainer 92*m*. Thus, the suture retainer 92*m* is at approximately the same temperature as the bone 20*m* when the force is applied against the suture retainer. The force causes the material of the suture retainer 92*m* to flow and grip the sections 72*m* and 74*m* of the suture 38*m*.

The suture retainer 92*m* may be formed of many different materials. However, it is believed that it will be preferred to form the suture retainer 92*m* of a biodegradable polymer. One biodegradable polymer which may be utilized is polycaperlactone. Alternatively, the suture retainer 92*m* could be formed of polyethylene oxide terephthalate or polybutylene terephthalate. It is also contemplated that other biodegradable or bioerodible copolymers could be utilized.

Although it is preferred to form the suture retainer 92*m* of a biodegradable material, the suture retainer could be formed of a material which is not biodegradable. For example, the suture retainer 92*m* could be formed of an acetyl resin, such as "DELRIN" (trademark). Alternatively, the suture retainer 92*m* could be formed of para-dimethylamino-benzenediaz-o sodium sulfonate, such as "DEXON" (trademark). The construction of the suture retainer 92*m* and the manner in which is cooperates with the suture 38*m* is the same as is disclosed in U.S. patent application Ser. No. 08/905,084 filed Aug. 1, 1997 by Peter M. Bonutti et al. and entitled "Method and Apparatus for Securing a Suture".

The suture retainer 92*m* is plastically deformed to grip the limbs 72*m* and 74*m* of the suture 38*m*. However, the suture retainer 92*m* could be constructed so as to be mechanically actuated to grip the suture 38*m*. If desired, a combination of a mechanical gripping action and plastic deformation could be utilized by a retainer to grip the suture 38*m*.

CONCLUSION

In view of the foregoing description, it is apparent that the present invention relates to a method of securing sections 22 and 24 of a fractured bone 20. Sections 22 and 24 of a fractured bone 20 are held against movement relative to each other by a force transmitting member, such as a suture 38, which extends through a passage 40 in the bone. The passage 40 in the bone may have a linear or nonlinear configuration. Tension is maintained in the force transmitting member 38 to press surfaces 28 and 30 on the fracture together by securing anchors 50 and 52 or suture retainers 92 to opposite ends of the force transmitting member 38. It is believed that a suture 38 may advantageously be used as the force transmitting member.

A tubular member 240 is positioned in a linear passage (FIGS. 13 and 15) or a nonlinear passage (FIG. 14) through the bone 20. The tubular member 240 extends into portions of the passage 40 on opposite sides of the fracture 26. End portions of the tubular member may be positioned in a compact outer layer 42 of the bone. The tubular member 240 may be formed of bone. The force transmitting member 38 may be formed of bone or other body tissue.

What is claimed is:

1. A fixation system for securing a portion of a body of a patient, the body portion including an anchor-receiving hole extending between a first surface and a second surface of the body portion, the anchor-receiving hole including a first entrance in the first surface of the body portion and a second entrance in the second surface of the body portion, the system comprising:

a plate having a bone contacting surface, a second surface opposite the bone contacting surface, and an opening extending between the bone contacting surface and the second surface of the plate, the opening having a central longitudinal axis and a maximum dimension transverse the central longitudinal axis of the opening, the plate being configured to be attached to the body portion with at least one fastener, the bone contacting surface, when the plate is attached to the body portion, being configured to contact the first surface of the body portion such that the opening is aligned with the first entrance of the anchor-receiving hole in the body portion;

an anchor having a first end, a second end, and a length therebetween, the anchor having a width transverse to the length, the anchor having a depth transverse to the width and the length, the length of the anchor being greater than the width of the anchor and greater than the maximum dimension of the opening of the plate, the width and the depth of the anchor being less than the maximum dimension of the opening of the plate thereby permitting the anchor to pass through the opening of the plate and into the anchor-receiving hole in the body portion, the anchor having at least one passage extending therethrough, the at least one passage having a central longitudinal axis transverse to the length of the anchor;

a securing member having a maximum dimension greater than the maximum dimension of the opening of the plate, the securing member having at least two apertures extending therethrough, the apertures each having a central longitudinal axis transverse to the maximum dimension of the securing member, the securing member being configured to be positioned adjacent to and extend across the opening of the plate; and an elongate member configured to be positioned through the anchor-receiving hole of the body portion, the at least one passage of the anchor, and the at least two apertures of the securing member to connect the anchor and the securing member.

2. The system of claim 1, further including a second plate positioned proximate the second surface of the body portion, wherein the elongate member is positioned through the second plate.

3. The system of claim 1, wherein the body portion includes bone.

4. The system of claim 1, wherein the plate is configured to be positioned between the securing member and the body portion.

5. The system of claim 1, wherein the elongate member comprises a polymeric material.

6. The system of claim 1, wherein the anchor comprises one of stainless steel and titanium.

7. The system of claim 1, wherein the securing member comprises one of stainless steel and titanium.

8. The system of claim 1, wherein the anchor is configured to be positioned adjacent to and extend across the second entrance of the anchor-receiving hole.

9. The system of claim 8, wherein tension in the elongate member serves in securing the position of the body portion between the anchor and the securing member.

10. The system of claim 8, wherein the at least one passage of the anchor includes a first passage and a second passage, and the elongate member is positioned through the first passage and the second passage.

11. The system of claim 8, wherein the anchor has a first surface and an opposite second surface, and the at least one passage extends between the first and second surfaces, the first surface of the anchor being configured to contact the second surface of the body portion.

12. The system of claim 11, wherein the second surface of the anchor is disposed at least in part in a first plane, the first plane, when the first surface of the anchor is contacted to the second surface of the body portion, being transverse to a central longitudinal axis of the anchor-receiving hole.

13. The system of claim 8, wherein the body portion is two bone pieces, the anchor-receiving hole extends through each of the two bone pieces, and the elongate member is configured to be tensioned with respect to the anchor and the securing member to clamp the two bone pieces in position with respect to one another.

14. The system of claim 8, wherein the elongated member is a suture.

15. The system of claim 14, wherein the suture is configured to be tensioned with respect to the anchor and the securing member, tension in the elongate member clamping the body portion and the plate between the anchor and the securing member.

16. A fixation system for securing a portion of a body of a patient, the body portion having an anchor-receiving hole extending from a first surface to a second surface of the body portion, the anchor-receiving hole having a first entrance in the first surface of the body portion and a second entrance in the second surface of the body portion, and the anchor-receiving hole having a central longitudinal axis and a maximum dimension transverse to the central longitudinal axis thereof, the system comprising:

a plate having a bone contacting surface, a second surface opposite the bone contacting surface, and an opening extending from the bone contacting surface to the second surface, the bone contacting surface being disposed at least in part in a first plane, the opening having a central longitudinal axis that is transverse to the first plane, the opening having a maximum dimension that is transverse to the central longitudinal axis of the opening, the bone contacting surface, when the plate is attached to the body portion, being configured to contact the first surface of the body portion such that the opening is aligned with the first entrance of the anchor-receiving hole in the body portion;

an anchor being configured to be positioned adjacent to and extend across the second entrance to the anchor-receiving hole, the anchor having a first end, a second end, a length between the first and second ends, a width transverse to and being less than the length, and a depth transverse to and being less than the width and the length, the length of the anchor being greater than the maximum dimension of the anchor-receiving hole and the maximum dimension of the opening of the plate, the width and the depth of the anchor being less than the maximum dimension of the anchor-receiving hole and the maximum dimension of the opening of the plate such that the anchor can pass through the opening of the plate and the anchor-receiving hole in the body portion, the anchor having at least one passage therethrough, the passage having a central longitudinal axis transverse to the length of the anchor;

a securing member configured to be positioned adjacent to and across the opening of the plate, the securing member having a maximum dimension greater than the maximum dimension of the opening of the plate, the securing member having at least two apertures extending therethrough, the apertures each having a central longitudinal axis transverse to the maximum dimension of the securing member; and an elongate member configured to extend through the anchor-receiving hole and be positioned through the at least one passage of the anchor and the at least two apertures of the securing member to connect the anchor and the securing member to one another.

17. The system of claim 16, wherein the anchor has a first surface and an opposite second surface, and the at least one passage extends between the first and second surfaces, the first surface of the anchor being configured to contact the second surface of the body portion.

18. The system of claim 17, wherein the second surface of the anchor is disposed at least in part in a first plane, the first plane, when the first surface of the anchor is contacted to the second surface of the body portion, being transverse to a central longitudinal axis of the anchor-receiving hole.

19. The system of claim 16, wherein the body portion is two bone pieces, the anchor-receiving hole extends through each of the two bone pieces, and the elongate member is configured to be tensioned with respect to the anchor and the securing member to clamp the two bone pieces in position with respect to one another.

20. The system of claim 16, wherein the elongated member is a suture, the suture being configured to be tensioned with respect to the anchor and the securing member, tension in the elongate member clamping the body portion and the plate between the anchor and the securing member.

* * * * *